US011723912B2

(12) United States Patent
Pulst et al.

(10) Patent No.: US 11,723,912 B2
(45) Date of Patent: Aug. 15, 2023

(54) STAUFEN1 AGENTS AND ASSOCIATED METHODS

(71) Applicant: University of Utah Research Foundation, Salt Lake City, UT (US)

(72) Inventors: Stefan M. Pulst, Sandy, UT (US); Daniel R. Scoles, Salt Lake City, UT (US); Sharan Paul, Salt Lake City, UT (US)

(73) Assignee: University of Utah Research Foundation, Salt Lake City, UT (US)

(*) Notice: Subject to any disclaimer, the term of this patent is extended or adjusted under 35 U.S.C. 154(b) by 0 days.

(21) Appl. No.: 16/467,945

(22) PCT Filed: Dec. 8, 2017

(86) PCT No.: PCT/US2017/065421
§ 371 (c)(1),
(2) Date: Jun. 7, 2019

(87) PCT Pub. No.: WO2018/107096
PCT Pub. Date: Jun. 14, 2018

(65) Prior Publication Data
US 2020/0069721 A1 Mar. 5, 2020

Related U.S. Application Data

(60) Provisional application No. 62/431,757, filed on Dec. 8, 2016.

(51) Int. Cl.
*C07H 21/02* (2006.01)
*C07H 21/04* (2006.01)
*A61K 31/713* (2006.01)
*A61K 45/06* (2006.01)
*C12N 15/113* (2010.01)
*A61P 25/28* (2006.01)

(52) U.S. Cl.
CPC ............ *A61K 31/713* (2013.01); *A61K 45/06* (2013.01); *A61P 25/28* (2018.01); *C12N 15/113* (2013.01); *C12N 2310/14* (2013.01)

(58) Field of Classification Search
CPC .......................... C12N 15/113; C12N 2310/11
See application file for complete search history.

(56) References Cited

U.S. PATENT DOCUMENTS

| 2004/0241845 | A1 | 12/2004 | Desgroseillers et al. |
| 2004/0259247 | A1 | 12/2004 | Tuschl et al. |
| 2013/0317087 | A1 | 11/2013 | Maquat et al. |
| 2014/0315981 | A1* | 10/2014 | Grinyo i Boira .. C12N 15/1138 514/44 A |

FOREIGN PATENT DOCUMENTS

| WO | WO 2003/074654 A2 | 9/2003 | |
| WO | WO 2006/039399 A2 * | 4/2006 | ........... C12N 15/113 |
| WO | WO 2009/143371 A2 | 11/2009 | |
| WO | WO 2012/109476 A2 | 8/2012 | |

OTHER PUBLICATIONS

Bondy-Chorney et al. (PLOS Genetics, 12(1): e1005827, Jan. 2016, pp. 1-22).*
Wang et al. (Oncology Reports, 32, 382-388, 2014).*
Vickers et al. (The Journal of Biological Chemistry, 278, 9, 2003, 7108-7118).*
Bondy-Chorney et al.; "Staufen1 Regulates Multiple Alternative Splicing Events either Positively or Negatively in DM1 Indicating Its Role as a Disease Modifier." PLoS Genet, Jan. 29, 2016; vol. 12, Issue 1; e1005827, pp. 1-22.
Hansen et al.; "Changes in Purkinje Cell Firing and Gene Expression Precede Behavioral Pathology in a Mouse Model of SCA2." Human Molecular Genetics; Oct. 28, 2012; vol. 22, Issue 2; pp. 271-283.
Laver et al.; "Genome-Wide Analysis of Staufen-Associated mRNAs Identifies Secondary Structures that Confer Target Specificity." Nucleic Acids Research; Oxford University Press; Aug. 13, 2013; vol. 41, Issue 20; pp. 9438-9460.
PCT Application No. PCT/US2017/065421 Filing date Dec. 8, 2017; Stefan M. Pulat International Search Report, dated Apr. 26, 2018, 15 Pages.
Paul et al.; "The Role of Staufen in Aberrant RNA Metabolism in SCA2 (P6.396)." Neurology; Apr. 4, 2016; vol. 86, Issue 16; p. 393.
Ravel-Chapuis et al.; "The RNA-Binding Protein Staufen1 is Increased in DM1 Skeletal Muscle and Promotes Alternative pre-MRNA Splicing" J Cell Biol, Mar. 19, 2012; vol. 196, Issue 6; pp. 699-712.
Kim et al.; "Staufen1-mediated mRNA decay induces Requiem mRNA decay through binding of Staufen1 to the Requiem 3' UTR." Nucleic Acids Research; vol. 42, No. 11; May 5, 2014; pp. 6999-7011.
Park et al.; "Staufen-mediated mRNA decay." Wiley Interdisciplinary Reviews: RNA; vol. 4, No. 4; May 16, 2013; pp. 423-435.
Paul et al.; "Staufen1 Link RNA stress granules and autophagy in a model of neurodegeneration." Nature Communications; vol. 9, No. 1; Sep. 7, 2018; 14 Pages.
Ramasamy et al.; "Zebrafish Staufen1 and Staufen2 are required for the survival and migration of primordial germ cells." Developmental Biology; Elsevier; vol. 292, No. 2; Mar. 2, 2006; p. 397.
Thomas et al.; "Mammalian Staufen 1 is recruited to stress granules and impairs their assembly." Journal of Cell Science; vol. 122, No. 4; Feb. 4, 2009; pp. 563-573.

(Continued)

*Primary Examiner* — Amy H Bowman
(74) *Attorney, Agent, or Firm* — Thorpe North & Western, LLP; David W. Osborne

(57) ABSTRACT

Methods of minimizing dysregulation of Staufen1-associated RNA metabolism can include introducing an amount of a Staufen1-regulating agent to a target cell sufficient to minimize the dysregulation. Therapeutic compositions for treating a neurodegenerative condition associated with Staufen1-induced dysregulation of RNA metabolism can include a therapeutically effective amount of a Staufen1-regulating agent and a pharmaceutically acceptable carrier.

7 Claims, 52 Drawing Sheets

Specification includes a Sequence Listing.

(56) References Cited

OTHER PUBLICATIONS

Gandelman, Mariana et al.; "Calcium derangement and STAU1-dependent ER stress in an in vitro model of SCA2 (P1.059)" Neurology, vol. 90, No. 15 Supplement; Apr. 9, 2018; 3 pages (XP055878654).
Scoles, Daniel R. et al.; "Antisense oligonucleotide therapy for spinocerebellar ataxia type 2" Nature, vol. 544, No. 7650; pp. 362-366; Apr. 1, 2017 (XP055607952, London ISSN: 0028-0836, DOI: 10.1038/nature22044).
Lee, Joshua et al.; "Antisense Therapy in Neurology" Journal of Personalized Medicine, vol. 3, No. 3, pp. 144-176; Aug. 2, 2013 (XP055163807; DOI: 10.3390/jpm3030144).
Evers, Melvin et al.; "Antisense oligonucleotides in therapy for neurodegenerative disorders" Advanced Drug Delivery Reviews, vol. 87, pp. 90-103; Jun. 1, 2015 (XP055266437, Amsterdam, NL; ISSN: 0169-409X, DOI: 10.1016/j.addr.2015.03.008).
Anderson, K N, et al.; "Expression profiling in spinal muscular atrophy reveals an RNA binding protein deficit" Neuromuscular Disorders, Elsevier Ltd, GB, vol. 14, No. 11, pp. 711-722, Nov. 1, 2004 (XP004598629, ISSN: 0960-8966, DOI: 10.1016/J.NMD.2004.08.009).
Paul, Sharan et al.; Staufen1 links RNA stress granules and autophagy in a model of neurodegeneration: Nature Communications, vol. 9, No. 1, 14 pages; Sep. 7, 2018 (XP055717462; DOI: 10.1038/s41467-018-06041-3).

* cited by examiner

SH-SY5Y cells

Western blot

N2a cells

Western blot

FIG. 14A (SEQ ID NO: 32)

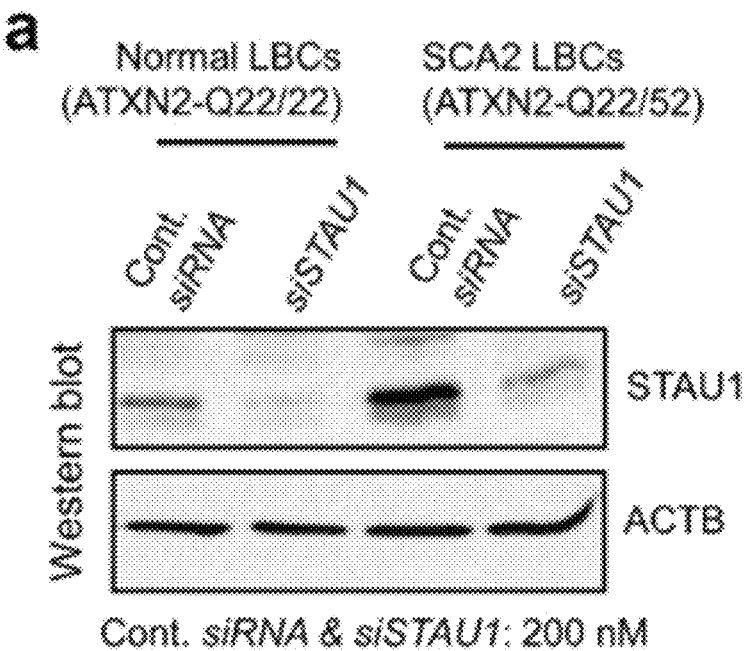
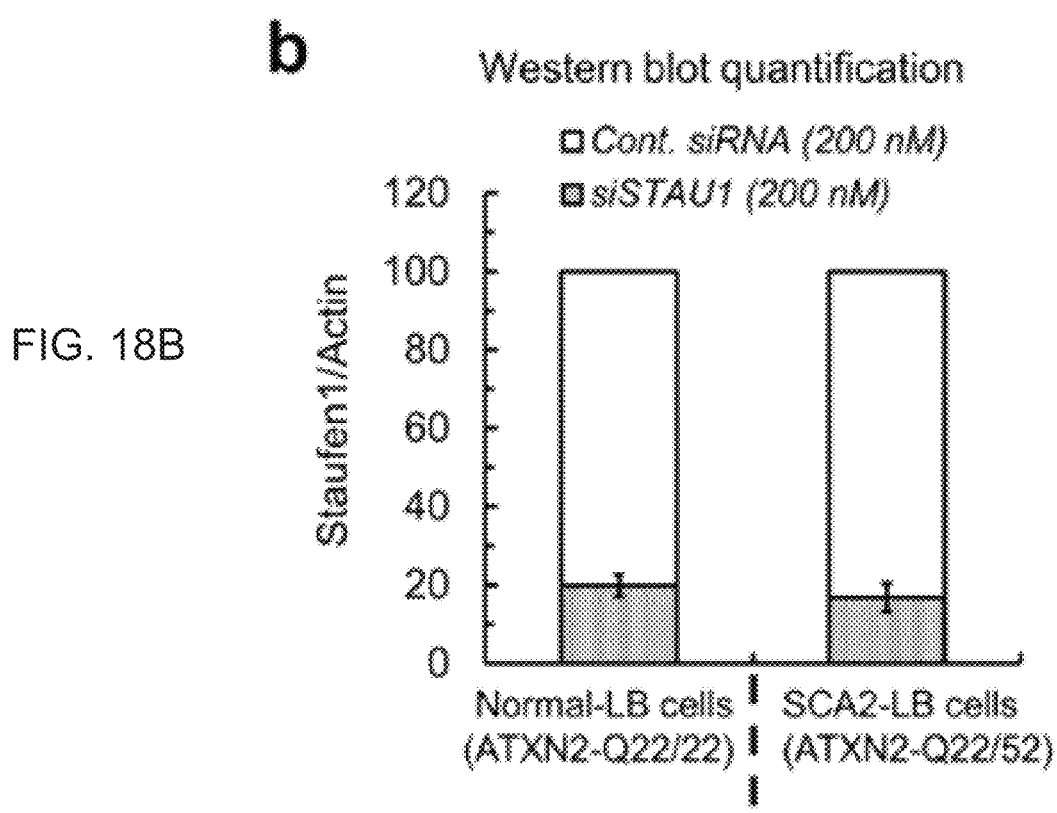
FIG. 18A
FIG. 18B

SEQUENCE LISTING

```
<160> NUMBER OF SEQ ID NOS: 31

<210> SEQ ID NO 1
<211> LENGTH: 20
<212> TYPE: DNA
<213> ORGANISM: Homo sapiens

<400> SEQUENCE: 1
tctcatgttg tagttatagg                                              20

<210> SEQ ID NO 2
<211> LENGTH: 20
<212> TYPE: DNA
<213> ORGANISM: Homo sapiens

<400> SEQUENCE: 2
ctggaaagat agtccagttg                                              20

<210> SEQ ID NO 3
<211> LENGTH: 21
<212> TYPE: RNA
<213> ORGANISM: Artificial Sequence
<220> FEATURE:
<223> OTHER INFORMATION: human siStau1
<220> FEATURE:
<221> NAME/KEY: misc_feature
<222> LOCATION: (20)..(21)
<223> OTHER INFORMATION: n is deoxythymidine

<400> SEQUENCE: 3
ccuauaacua caacaugagn n                                            21

<210> SEQ ID NO 4
<211> LENGTH: 19
<212> TYPE: RNA
<213> ORGANISM: Homo sapiens
```

```
<400> SEQUENCE: 4
gagccuuguu gauccuuaa                                              19

<210> SEQ ID NO 5
<211> LENGTH: 18
<212> TYPE: DNA
<213> ORGANISM: Homo sapiens

<400> SEQUENCE: 5
gggcccctca ccatgtcg                                               18

<210> SEQ ID NO 6
<211> LENGTH: 18
<212> TYPE: DNA
<213> ORGANISM: Homo sapiens

<400> SEQUENCE: 6
cgggcttgcg gacattgg                                               18

<210> SEQ ID NO 7
<211> LENGTH: 27
<212> TYPE: DNA
<213> ORGANISM: Homo sapiens

<400> SEQUENCE: 7
ccgcccggcg tgcgagccgg tgtatgg                                     27

<210> SEQ ID NO 8
<211> LENGTH: 27
<212> TYPE: DNA
<213> ORGANISM: Homo sapiens

<400> SEQUENCE: 8
gtagactgag gcagtccttt gttactg                                     27

<210> SEQ ID NO 9
<211> LENGTH: 19
<212> TYPE: DNA
<213> ORGANISM: Homo sapiens

<400> SEQUENCE: 9
acatcgctca gacaccatg                                              19

<210> SEQ ID NO 10
<211> LENGTH: 22
<212> TYPE: DNA
<213> ORGANISM: Homo sapiens

<400> SEQUENCE: 10
tgtagttgag gtcaatgaag gg                                          22

<210> SEQ ID NO 11
<211> LENGTH: 20
<212> TYPE: DNA
<213> ORGANISM: Homo sapiens

<400> SEQUENCE: 11
gaaaatctgg caccacacct                                             20

<210> SEQ ID NO 12
<211> LENGTH: 20
<212> TYPE: DNA
<213> ORGANISM: Homo sapiens
```

```
<400> SEQUENCE: 12
tagcacagcc tggatagcaa                                           20

<210> SEQ ID NO 13
<211> LENGTH: 20
<212> TYPE: DNA
<213> ORGANISM: Homo sapiens

<400> SEQUENCE: 13
tccttggttt caaagtcccg                                           20

<210> SEQ ID NO 14
<211> LENGTH: 20
<212> TYPE: DNA
<213> ORGANISM: Homo sapiens

<400> SEQUENCE: 14
attttcatcc ccagagccag                                           20

<210> SEQ ID NO 15
<211> LENGTH: 19
<212> TYPE: DNA
<213> ORGANISM: Homo sapiens

<400> SEQUENCE: 15
aaggacggag cacagaaac                                            19

<210> SEQ ID NO 16
<211> LENGTH: 18
<212> TYPE: DNA
<213> ORGANISM: Homo sapiens

<400> SEQUENCE: 16
gagtgagacc caggatgc                                             18

<210> SEQ ID NO 17
<211> LENGTH: 25
<212> TYPE: DNA
<213> ORGANISM: Homo sapiens

<400> SEQUENCE: 17
aagatatgga ctccagttat gcaaa                                     25

<210> SEQ ID NO 18
<211> LENGTH: 20
<212> TYPE: DNA
<213> ORGANISM: Homo sapiens

<400> SEQUENCE: 18
caaagcctca agttcctcat                                           20

<210> SEQ ID NO 19
<211> LENGTH: 20
<212> TYPE: DNA
<213> ORGANISM: Homo sapiens

<400> SEQUENCE: 19
ccgacccaca gatccctcta                                           20

<210> SEQ ID NO 20
<211> LENGTH: 20
<212> TYPE: DNA
```

<213> ORGANISM: Homo sapiens

<400> SEQUENCE: 20
gctgtcattg ggcagagagt                                                 20

<210> SEQ ID NO 21
<211> LENGTH: 20
<212> TYPE: DNA
<213> ORGANISM: Homo sapiens

<400> SEQUENCE: 21
gcacgtcttc ctgagaacca                                                 20

<210> SEQ ID NO 22
<211> LENGTH: 20
<212> TYPE: DNA
<213> ORGANISM: Homo sapiens

<400> SEQUENCE: 22
cactgagggc tgaaactcca                                                 20

<210> SEQ ID NO 23
<211> LENGTH: 20
<212> TYPE: DNA
<213> ORGANISM: Homo sapiens

<400> SEQUENCE: 23
gccagatcca gcatcgttgt                                                 20

<210> SEQ ID NO 24
<211> LENGTH: 20
<212> TYPE: DNA
<213> ORGANISM: Homo sapiens

<400> SEQUENCE: 24
ctctggctct tggtggtctg                                                 20

<210> SEQ ID NO 25
<211> LENGTH: 19
<212> TYPE: DNA
<213> ORGANISM: Homo sapiens

<400> SEQUENCE: 25
cgaacctcag ggcaagatg                                                  19

<210> SEQ ID NO 26
<211> LENGTH: 22
<212> TYPE: DNA
<213> ORGANISM: Homo sapiens

<400> SEQUENCE: 26
tttcctcatt ccggctcttt ag                                              22

<210> SEQ ID NO 27
<211> LENGTH: 22
<212> TYPE: DNA
<213> ORGANISM: Homo sapiens

<400> SEQUENCE: 27
agtacatgct ccttacagaa cg                                              22

<210> SEQ ID NO 28
<211> LENGTH: 20

```
<212> TYPE: DNA
<213> ORGANISM: Homo sapiens

<400> SEQUENCE: 28
tgatgcccaa cctttacctg                                              20

<210> SEQ ID NO 29
<211> LENGTH: 22
<212> TYPE: DNA
<213> ORGANISM: Homo sapiens

<400> SEQUENCE: 29
cgtcgacaac ggctccggca tg                                           22

<210> SEQ ID NO 30
<211> LENGTH: 23
<212> TYPE: DNA
<213> ORGANISM: Homo sapiens

<400> SEQUENCE: 30
gggcctcgtc acccacatag gag                                          23

<210> SEQ ID NO 31
<211> LENGTH: 21
<212> TYPE: RNA
<213> ORGANISM: Artificial Sequence
<220> FEATURE:
<223> OTHER INFORMATION: mouse siStau1
<220> FEATURE:
<221> NAME/KEY: misc_feature
<222> LOCATION: (20)..(21)
<223> OTHER INFORMATION: n is deoxythymidine

<400> SEQUENCE: 31
caacuguacu accuuuccan n                                            21
```

STAUFEN1 AGENTS AND ASSOCIATED METHODS

PRIORITY DATA

This application claims the benefit of U.S. Provisional Patent Application Ser. No. 62/431,757, filed on Dec. 8, 2016, which is incorporated herein by reference.

GOVERNMENT INTEREST

This invention was made with government support under grant number NS033123 awarded by the National Institutes of Health. The government has certain rights in the invention.

SEQUENCE LISTING

This application contains a sequence listing which is incorporated herein by reference in ASCII format named Sequence_Listing.txt, created Feb. 13, 2023, and is 5 KB in size. The sequences contained in the sequence listing are found throughout the originally filed application.

BACKGROUND

Neurodegenerative diseases occur when nerve cells in the brain or peripheral nervous system lose function over time and ultimately die. Further, nerve cells generally don't reproduce or replace themselves. The risk of being affected by a neurodegenerative disease increases with age. Although treatments may help relieve some of the physical or mental symptoms associated with neurodegenerative diseases, there is currently no cure. Non-limiting examples of neurodegenerative diseases include peripheral neuropathy, Alzheimer's disease (AD), Parkinson's disease (PD), Huntington's disease (HD), spinocerebellar ataxia (SCA), prion disease, motor neuron disease (MND), amyotrophic lateral sclerosis (ALS), multiple sclerosis (MS), and spinal muscular atrophy (SMA) among others.

BRIEF DESCRIPTION OF THE DRAWINGS

For a fuller understanding of the nature and advantage of the present invention, reference is made to the following detailed description of preferred embodiments and in connection with the accompanying drawings, in which:

FIG. 14A is a schematic where single guide RNA (sgRNA) sequence (green), the PAM sequence (NGG) (red) and Cas9 cleavage site (red arrowhead) are shown. Cas9 cleaves the DNA at the target site with the help of sgRNA guidance. The left and right arms of the target donor insert CAG58 repeats into the ATXN2 locus through HDR. RT-PCR screening for ATXN2-CAG22/58 [ATXN2-Q22/58] Knockin-positive clones using the indicated primers. SH-SY5Y cells were co-transfected with linearized donor vector and single guide RNA pgRNA-Cas9 vector. Puromycin selected cells were titrated in 96-well plates at 1 cell/well, and then expanded and maintained for PCR screening to identify knock-in positive cells.

FIG. 18A is a western blot analysis where Normal (ATXN2-Q22/22) and SCA2 (ATXN2-Q22/52) LBCs were electroporated with STAU1 RNAi and Staufen1 levels were determined by western blotting after 4 days post-electroporation.

FIG. 18B is a graph of the quantification of the blot in FIG. 18A.

DESCRIPTION OF EMBODIMENTS

Figure 1A:
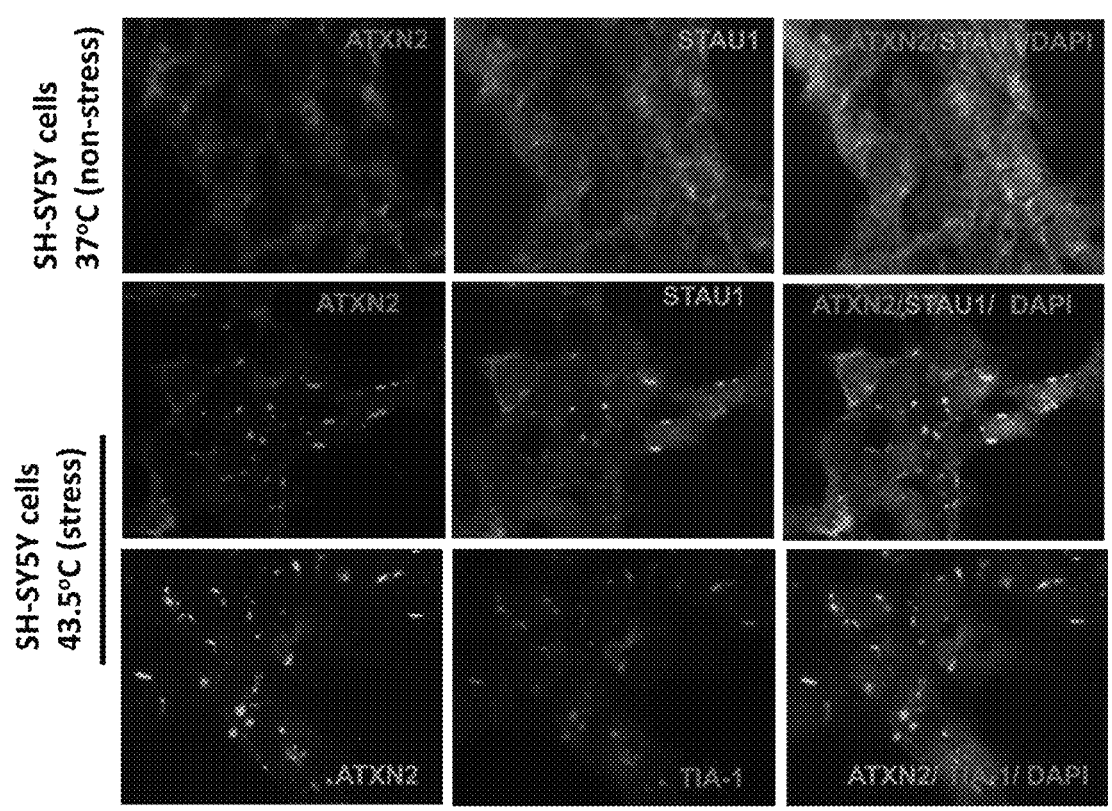
FIG. 1A presents images where ATXN2 and Staufen1 co-localize in stress granules under stress condition. SH-SY5Y cells were treated with heat shock at 43.5° C. for 1 hr. Fixed cells were immunostained with ATXN2, Staufen1 and TIA-1 (stress granule marker) antibodies. Representative cells showing co-localization of endogenous ATXN2 (red) and Staufen1 (green) or ATXN2 (green) and TIA-1(red) as aggregates by merge images (yellow signals). ATXN2 and Staufen1 co-localizations are not seen under non-stress (37° C.) condition.

Although the following detailed description contains many specifics for the purpose of illustration, a person of ordinary skill in the art will appreciate that many variations and alterations to the following details can be made and are considered to be included herein. Accordingly, the following embodiments are set forth without any loss of generality to, and without imposing limitations upon, any claims set forth. It is also to be understood that the terminology used herein is for the purpose of describing particular embodiments only, and is not intended to be limiting. Unless defined otherwise, all technical and scientific terms used herein have the same meaning as commonly understood by one of ordinary skill in the art to which this disclosure belongs.

As used in this written description, the singular forms "a," "an" and "the" include express support for plural referents unless the context clearly dictates otherwise. Thus, for example, reference to "a polymer" can include a plurality of such polymers.

As used herein, "subject" refers to a mammal that can benefit from treatment with a Staufen1-regulating agent. A benefit can be obtained if the subject has a disease or condition, or is at risk of developing a disease or condition for which a Staufen1-regulating agent is a therapeutically effective treatment or preventative measure. In some aspects, such subject may be a human.

As used herein, the terms "treat," "treatment," or "treating" when used in conjunction with the administration of a Staufen1-regulating agent, such as an siRNA or anti-sense oligonucleotide (ASO) that targets the STAU1 gene, including compositions and dosage forms thereof, refers to administration to subjects who are either asymptomatic or symptomatic. In other words, "treat," "treatment," or "treating" can be to reduce, ameliorate or eliminate symptoms associated with a condition present in a subject, or can be prophylactic, (i.e. to prevent or reduce the occurrence of the symptoms in a subject). Such prophylactic treatment can also be referred to as prevention of the condition. Treatment outcomes can be expected or unexpected. In one specific aspect, a treatment outcome can be a delay in occurrence or onset of a disease or conditions or the signs or symptoms thereof. In another aspect, a treatment can be reducing, ameliorating, eliminating, or otherwise providing a subject with relief from (i.e. relieving) the condition with which they are afflicted, or providing relief from signs or symptoms of the condition.

As used herein a "therapeutic agent" refers to an agent that can have a beneficial or positive effect on a subject when administered to the subject in an appropriate or effective amount.

As used herein, the terms "inhibit" or "inhibiting" are used to refer to a variety of inhibition techniques. For example, the terms "inhibit" or "inhibiting" can refer to pre- and/or post-transcriptional inhibition. With respect to pre-transcription inhibition, "inhibit" or "inhibiting" can refer to preventing or reducing transcription of a gene, inducing altered transcription of a gene, and/or reducing a rate of transcription of a gene, whether permanent, semi-permanent, or transient. Thus, in some examples, "inhibit" or "inhibiting" can refer to permanent changes to the DNA, whereas in other examples no permanent change to the DNA is made. With respect to post-transcriptional inhibition, "inhibit" or "inhibiting" can refer to preventing or reducing translation of a genetic sequence to a protein, inducing an altered translation of a genetic sequence to an altered protein (e.g. as misfolded protein, etc.), and/or reducing a rate of translation of a genetic sequence to a protein, whether permanent, semi-permanent, or transient. In some specific examples, "inhibit" or "inhibiting" can refer to pre-transcriptional inhibition. In other specific examples, "inhibit" or "inhibiting" can refer to post-transcriptional inhibition. Of course, the type of inhibition can depend on the specific type(s) of inhibitor(s) or therapeutic agent(s) employed. Thus, "inhibit" or "inhibiting" can include any decrease in expression of a gene as compared to native expression, whether pre- or post-transcriptional, partial or complete.

As used herein, the terms "formulation" and "composition" are used interchangeably and refer to a mixture of two or more compounds, elements, or molecules. In some aspects the terms "formulation" and "composition" may be used to refer to a mixture of one or more active agents with a carrier or other excipients. Compositions can take nearly any physical state, including solid, liquid (i.e. solution), or gas. Furthermore, the term "dosage form" can include one or more formulation(s) or composition(s) provided in a format for administration to a subject.

The phrase "effective amount," "therapeutically effective amount," or "therapeutically effective rate(s)" of an active ingredient refers to a non-toxic, but sufficient amount or delivery rates of the active ingredient or therapeutic agent, to achieve therapeutic results in treating a disease or condition for which the drug is being delivered. It is understood that various biological factors may affect the ability of a substance to perform its intended task. Therefore, an "effective amount," "therapeutically effective amount," or "therapeutically effective rate(s)" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a subjective decision. The determination of a therapeutically effective amount or delivery rate is well within the ordinary skill in the art of pharmaceutical sciences and medicine. See, for example, Meiner and Tonascia, "Clinical Trials: Design, Conduct, and Analysis," Monographs in Epidemiology and Biostatistics, Vol. 8 (1986).

As used herein, a "dosing regimen" or "regimen" such as "treatment dosing regimen," or a "prophylactic dosing regimen," refers to how, when, how much, and for how long a dose of a composition can or should be administered to a subject in order to achieve an intended treatment or effect.

As used herein, "carrier," and "pharmaceutically acceptable carrier" may be used interchangeably, and refer to any liquid, gel, salve, solvent, liquid, diluent, fluid ointment base, liposome, micelle, giant micelle, or the like, or any other suitable carrier that is suitable for delivery of a therapeutic agent to and/or into a target cell (e.g. a nerve cell) and for use in contact with a subject or the subject's tissue without causing adverse physiological responses, and which does not interact with the other components of the composition in a deleterious manner.

In this application, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term, like "comprising" or "including," in this written description it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. Unless otherwise stated, use of the term "about" in accordance with a specific number or numerical range should also be understood to provide support for such numerical terms or range without the term "about". For example, for the sake of convenience and brevity, a numerical range of "about 50 milligrams to about 80 milligrams" should also be understood to provide support for the range of "50 milligrams to 80 milligrams." Furthermore, it is to be understood that in this written description support for actual numerical values is provided even when the term "about" is used therewith. For example, the recitation of "about" 30 should be construed as not only providing support for values a little above and a little below 30, but also for the actual numerical value of 30 as well.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

Reference in this application may be made to compositions, systems, or methods that provide "improved" or "enhanced" performance. It is to be understood that unless otherwise stated, such "improvement" or "enhancement" is a measure of a benefit obtained based on a comparison to compositions, systems or methods in the prior art. Furthermore, it is to be understood that the degree of improved or enhanced performance may vary between disclosed embodiments and that no equality or consistency in the amount, degree, or realization of improvement or enhancement is to be assumed as universally applicable.

Reference throughout this specification to "an example" means that a particular feature, structure, or characteristic described in connection with the example is included in at least one embodiment. Thus, appearances of the phrases "in an example" in various places throughout this specification are not necessarily all referring to the same embodiment.

Example Embodiments

An initial overview of invention embodiments is provided below and specific embodiments are then described in further detail. This initial summary is intended to aid readers in understanding the technological concepts more quickly, but is not intended to identify key or essential features thereof, nor is it intended to limit the scope of the claimed subject matter.

Autosomal dominant cerebellar ataxias (ADCAs) are a heterogeneous group of neurodegenerative disorders characterized by progressive degeneration of the cerebellum, brain stem, and spinal cord. Degeneration occurs at the cellular level and in certain subtypes results in cellular death. Cellular death or dysfunction can interfere with the line of communication from the central nervous system to target muscles in the body.

Clinically, ADCA has been divided into three types (ADCA types I, II, and III), which are further divided into various sub-types. Each of these types and sub-types can cause a variety of deleterious effects. Type I ADCA, sub-type 1 conditions are typically characterized by CAG nucleotide repeats in the DNA, which code for polyglutamine. These polyglutamine segments can cause degenerative effects on the protein level. As non-limiting examples, ADCA Type I, sub-type 1 can include SCA1, SCA2, SCA3, SCA17, and DRPLA, among others. However, many neurodegenerative disorders can be associated with other trinucleotide repeat expansions, or other genetic repeat expansions, besides CAG nucleotide repeats.

As one illustrative example of a neurodegenerative disorder, spinocerebellar ataxia type 2 (SCA2) is an autosomal dominant cerebellar ataxia characterized by progressive degeneration of cerebellar Purkinje cells (PCs), and selective loss of neurons within the brainstem and spinal cord. As described above, the genetic defect in SCA2 is expansion of CAG repeats (code for polyglutamine) in exon 1 of ATXN2 gene. Mutant ataxin-2 (ATXN2) protein with excessive polyglutamine acquires gain of function and shows aggregation in the SCA2 brain. ATXN2 aggregates and degeneration of cerebellar PCs, and altered RNA expressions are pathological consequences of expanded CAG repeat expression in SCA2 cells.

ATXN2 is widely expressed in the mammalian nervous system. ATXN2 is involved in regulation of the EGF receptor, inositol 1,4,5-triphosphate receptor (IP3R), and has role in translational regulation as well as embryonic development. ATXN2 interacts with multiple RNA binding proteins, including RNA splicing factor A2BP1/Fox1, polyA binding protein 1 (PABP1), DDX6, and Tar DNA binding protein-43 (TDP-43) demonstrating its unique role in RNA metabolism. Furthermore, ATXN2 is a constituent protein of subcellular components, like stress granules (SGs) and P-bodies, supporting its function in sequestering mRNAs and regulating protein translation during stress.

Further, double-stranded RNA-binding proteins Staufen1 (STAU1) and staufen-2 (STAU2) can be recruited to cytoplasmic inclusions in brain oligodendrocytes and other cultured cells and modulate SGs dynamics. Staufen1 can perform a number of RNA-related functions such as mRNA transport and degradation as well as being a protein localized to RNA granules under cellular stress. Although Staufen1 can be associated with mRNA transport in both oocytes and somatic cells in vertebrates, Staufen1 is a multifunctional protein involved in regulating RNA metabolism in various cell types. Furthermore, Staufen1 can regulate the translational efficiency of a population of mRNAs via 5'UTR and the stability of transcripts through 3'UTR, a mechanism referred as Staufen-mediated RNA decay (SMD).

It is noted that RNA metabolism, including translation, transport, storage, and degradation, have assumed important roles in cellular function both in health and disease. Stress granules play an important role in RNA metabolism as they can regulate translation in times of cellular stress, and RNA granules can regulate mRNA transport and local expression control. SGs are composed of mRNA, ribosomal RNAs, and non-coding RNAs as well as a specific complement of proteins that can vary from cell to cell.

With this in mind, ATXN2 can interact with multiple RNA binding proteins, including PABP1, A2BP1/Fox1, DDX6 and TDP-43, suggesting a unique role for ATXN2 in RNA metabolism. Further, Staufen1 is a RNA-dependent interactor for ATXN2. Although the strength of protein-protein interaction does not appear to differ for wild-type and mutant ATXN2, in the presence of mutant ATXN2, steady-state Staufen1 levels can be greatly increased in SCA2 patient-derived cells. Thus, as will be described in further detail herein infra, in some cases, the expansion of the polyglutamine regions in the mutant ATXN2 protein, or other proteins having a polynucleotide expansion, can facilitate increased levels of Staufen1 in SCA2 patient-derived cells. Further still, increased levels of Staufen1 in nerve cells can play an important role in the deleterious effects of ADCA (e.g. ADCA type I, sub-type 1, etc.) and other neurodegenerative disorders.

Accordingly, the present disclosure describes compositions and methods for normalizing or controlling Staufen1 levels or activity in a target cell (e.g. a nerve cell). As one non-limiting example, a method of minimizing dysregulation of Staufen1-associated RNA metabolism is described. The method can include introducing an amount of a Staufen1-regulating agent to a target cell sufficient to minimize the dysregulation.

A method of controlling Staufen1 activity is also described. The method can include introducing an amount of a Staufen1-regulating agent to a target cell sufficient to reduce Staufen1 activity as compared to Staufen1 activity prior to or without introducing the Staufen1-regulating agent.

Further, a method of controlling Staufen1 accumulation in a target cell is described. The method can include introducing an amount of a Staufen1 regulating agent to a target cell sufficient to reduce a concentration of Staufen1 in the target cell as compared to the concentration in the target cell prior to or without introducing the Staufen1-regulating agent.

Further still, a method of treating a neurodegenerative condition associated with Staufen1-induced dysregulation of RNA metabolism is described. The method can include administering a therapeutically effective amount of a Staufen1-regulating agent to a target cell of a subject.

A therapeutic agent or composition for treating a neurodegenerative condition associated with Staufen1-induced dysregulation of RNA metabolism is also described. The therapeutic agent can be a Staufen1-regulating agent. The therapeutic composition can include a therapeutically effective amount of a Staufen1-regulating agent and a pharmaceutically acceptable carrier.

In the present disclosure, it is noted that when discussing the various methods, the therapeutic agent, and the therapeutic composition, each of these discussions can be considered applicable to each of these examples, whether or not they are explicitly discussed in the context of that example. Thus, for example, in discussing details about a method per se, such discussion also refers to the other methods described herein, the therapeutic agent, the therapeutic composition, therapeutic dosage amounts and forms, and vice versa.

In further detail, the present disclosure describes methods of minimizing dysregulation of Staufen1-associated RNA metabolism. As described above, Staufen1 can perform a number of RNA-related functions, such as mRNA transport and degradation, for example. Thus, in some cases, having elevated Staufen1 levels in a target cell can lead to dysregulation of Staufen1-associated RNA metabolism. Further, in some examples, elevated levels of Staufen1 in a target cell can lead to undesired and accelerated degradation of various cellular components. Accordingly, the methods can include introducing a sufficient amount of a Staufen1-regulating agent to a target cell to minimize Staufen1-associated dysregulation of RNA metabolism.

A variety of Staufen1-regulating agents can be employed in the methods recited herein. It is noted that when discussing Staufen1-regulating agents per se, it is to be understood that a Staufen1-regulating agent can act or function to regulate Staufen1 without directly interacting with Staufen1. For example, in some cases a Staufen1-regulating agent can be an agent that acts upstream from Staufen1 to regulate Staufen1. As one non-limiting example, in some cases, a Staufen1-regulating agent can be a therapeutic agent that inhibits expression of mutant ATXN2. In this way, the staufen1-regulating agent can facilitate regulation of Staufen1 without directly interacting with Staufen1 protein or STAU1 gene, but rather with cellular components or genes which have a direct or indirect impact on Staufen1 protein, including its properties, or behavior, such as lifespan, residence time, binding availability, stability, cellular accumulation, etc. Thus, in some examples, an effective Staufen1-regulating agent can also include an gene therapy agent, such as for modifying a mutant allele to a wild-type allele to facilitate regulation of Staufen1.

As non-limiting examples, in some cases, the Staufen1-regulating agent can be or include a Staufen1-inhibiting agent. A Staufen1-inhibiting agent can include any agent that fully or partially inhibits the transcription or translation of Staufen1 in the target cell. In some additional examples, the Staufen1-regulating agent can be or include a Staufen1-inactivating agent. A Staufen1-inactivating agent can include any agent that binds to, degrades, etc. the Staufen1 protein so as to reduce or eliminate its RNA metabolism (e.g. RNA transportation, RNA degradation, etc.) function in the target cell. In some examples, the Staufen1-regulating agent can be or include a mutant ATXN2-inhibiting agent (or inhibiting agent for another mutant gene having excessive nucleotide repeats). A mutant ATXN2-inhibiting agent can be any agent that inhibits the transcription or translation of mutant ATXN2 (e.g. ATXN2 having 32 or more polyglutamine repeats) in the target cell. In some examples, the ATXN2-inhibiting agent can be or include an agent that can partially or fully silence transcription or translation of ATXN2. In some additional examples, the ATXN2-inhibiting agent can be or include an agent that can edit the mutant ATXN2 gene to modify the mutant allele to a wild-type sequence (e.g. to include from about 21 to about 31, from about 21 to about 25, or from about 22 to about 23 polyglutamine repeats, rather than 32 or more). As will be recognized by one skilled in the art, other neurodegenerative diseases can be affected by excessive polynucleotide repeats on genes other than ATXN2 where the normal number of repeats can vary from the ranges listed above. In such cases, the mutant gene can be edited to include a polynucleotide repeat within the wild-type range. In some examples, the Staufen1-regulating agent can be or include a mutant ATXN2-inactivating agent. The mutant ATXN2-inactivating agent can include any agent that binds to, degrades, or otherwise inactivates the mutant ATXN2 protein (or another mutant protein having excessive nucleotide repeats) or prevents or reduces interaction of the mutant ATXN2 protein with Staufen1 in a manner that minimizes excessive accumulation of Staufen1 in the target cell. In some examples, the Staufen1-regulating agent can reduce or block Staufen1 interaction with mRNAs, which can result in altered mRNA expression or abundance. In some examples, the Staufen1-regulating agent can be a mechanistic target of rapamycin (mTOR)-inhibiting agent. An mTOR-inhibiting agent can be any agent that inhibits the transcription or translation of mTOR in the target cell. In some further examples, the Staufen1-regulating agent can be an mTOR-inactivating agent. An mTOR inactivating agent can be any agent that can bind to, degrade, etc. mTOR protein to prevent or minimize its interaction with Staufen1 protein. Thus, there are a variety of Staufen1-regulating agents that can be employed to perform one or more of these functions. Non-limiting examples of Staufen1-regulating agents can include siRNAs, miRNAs, antisense oligonucleotides (with chemistries including phosphorothioate base pair linkages, 2'-methoxyethyl, 2'-O-methyl, 2'-fluoro, 2'-(3-hydroxy)-propyl, locked nucleic acid (LNA), peptide nucleic acid (PNA), cyclohexene nucleic acid (CeNA), hexitol nucleic acids (HNA), morpholino, in combinations including mixed, chimeric or gapmer), ribozymes, peptide nucleic acids, morpholinos, small molecules, the like, or combinations thereof.

In some specific examples, the Staufen1-regulating agent can be an antisense oligonucleotide (ASO). In some aspects, the ASO can include one or more suitable modifications, such as sulfur for oxygen substitutions (e.g. introduction of phosphorothioate linkages), 2'-OH modifications, 2'-O-methyl modifications, 2'-fluoro modifications, 2'-O-methoxyethyl modifications, locked nucleic acid (LNA) modifications, bridged nucleic acid (BNA) modifications, peptide nucleic acid (PNA) modifications, morpholino modifications, hexitol nucleic acid (HNAs) modifications, introduction of central phosphodiester or phosphorothioate residues (e.g. to form a "gapmer"), the like, or combinations thereof. In some non-limiting examples, the ASO can include a nucleotide sequence of 5'-TCTCATGTTGTAGT-TATAGG-3' (SEQ ID NO: 1), 5tCTGGAAAGA-TAGTCCAGTTG-3' (SEQ ID NO: 2), or a combination thereof. In some additional examples, the ASO can include a nucleotide sequence that is at least 95% homologous to SEQ ID NO: 1, or a segment thereof having at least 13, 15, 17, or 19 consecutive nucleotides of SEQ ID NO: 1. In some other examples, the ASO can include a nucleotide sequence that is at least 90% homologous to SEQ ID NO: 1, or a segment thereof having at least 13, 15, 17, or 19 consecutive nucleotides of SEQ ID NO: 1. In yet other examples, the ASO can include a nucleotide sequence that is at least 85% homologous to SEQ ID NO: 1, or a segment thereof having at least 13, 15, 17, or 19 consecutive nucleotides of SEQ ID NO: 1. In some further examples, the ASO can include a nucleotide sequence that is at least 95% homologous to SEQ ID NO: 2, or a segment thereof having at least 13, 15, 17, or 19 consecutive nucleotides of SEQ ID NO: 2. In some other examples, the ASO can include a nucleotide sequence that is at least 90% homologous to SEQ ID NO: 2, or a segment thereof having at least 13, 15, 17, or 19 consecutive nucleotides of SEQ ID NO: 2. In yet other examples, the ASO can include a nucleotide sequence that is at least 85% homologous to SEQ ID NO: 2, or a segment thereof having at least 13, 15, 17, or 19 consecutive nucleotides of SEQ ID NO: 2.

In some additional specific examples, the Staufen1-regulating agent can be a small interfering RNA (siRNA). In some examples, the siRNA can include one or more suitable modifications, such as a 2'-sugar modification, an altered ring structure, a nucleobase modification, the like, or a combination thereof. It is further noted that the siRNA can include any suitable 3' nucleotide overhangs. In some specific examples, the siRNA can include a nucleotide sequence of 5'-CCUAUAACUACAACAUGAGdTdT-3' (SEQ ID NO: 3), 5'-GAGCCUUGUUGAUCCUUAA-3' (SEQ ID NO: 4), etc. on the guide/antisense strand. In some further examples, the siRNA can include a nucleotide sequence that is at least 95% homologous to SEQ ID NO: 3, or a segment thereof having at least 13, 15, 17, or 19 consecutive nucleotides of SEQ ID NO: 3 on the guide/antisense strand. In some other examples, the siRNA can include a nucleotide sequence that is at least 90% homologous to SEQ ID NO: 3, or a segment thereof having at least 13, 15, 17, or 19 consecutive nucleotides of SEQ ID NO: 3 on the guide/antisense strand. In still other examples, the siRNA can include a nucleotide sequence that is at least 85% homologous to SEQ ID NO: 3, or a segment thereof having at least 13, 15, 17, or 19 consecutive nucleotides of SEQ ID NO: 3 on the guide/antisense strand. In some further examples, the siRNA can include a nucleotide sequence that is at least 95% homologous to SEQ ID NO: 4, or a segment thereof having at least 13, 15, 17, or 19 consecutive nucleotides of SEQ ID NO: 4 on the guide/antisense strand. In some other examples, the siRNA can include a nucleotide sequence that is at least 90% homologous to SEQ ID NO: 4, or a segment thereof having at least 13, 15, 17, or 19 consecutive nucleotides of SEQ ID NO: 4 on the guide/antisense strand. In still other examples, the siRNA can include a nucleotide sequence that is at least 85% homologous to SEQ ID NO: 4, or a segment thereof having at least 13, 15, 17, or 19 consecutive nucleotides of SEQ ID NO: 4 on the guide/antisense strand.

In some examples, the Staufen1-regulating agent can be a gene therapy agent that does not directly interact with Staufen1 protein or STAU1 gene (e.g. a mutant ATXN2-inhibiting agent, for example). In such examples, the Staufen1-regulating agent can be used for gene therapy (e.g. homologous recombination, CRISPR/Cas9 gene editing, etc.) to permanently alter the DNA to prevent expression of mutant ATXN2 (or other similar gene including excessive CAG repeats or other polynucleotide repeats). In some specific examples, CRISPR/Cas9 systems can be employed. For example, by delivering a Cas9 nuclease complexed with a synthetic guide RNA into a target cell, the cell's genome can be cut at a desired location, allowing existing genes to be removed and/or altered genes to be added. Thus, in some examples, a CRISPR/Cas9 system can be administered to an individual having a neurodegenerative disorder to remove or edit the mutant ATXN2 gene and replace it with the wild-type version of the gene.

The Staufen1-regulating agent can be introduced to the target cell in a variety of ways. In some examples, the Staufen1-regulating agent can be introduced to the target cell as a "free" Staufen1-regulating agent that is not bound to or carried by a delivery vector or vehicle. However, as will be recognized by one skilled in the art, there are a number of challenges to in vivo delivery of certain types of therapeutic agents. As such, in other examples, the Staufen1-regulating agent can be introduced to the target cell via a delivery vector or vehicle. For example, in some cases, the Staufen1-regulating agent can be bound to or carried by a cell targeting agent that targets a specific cell surface receptor to facilitate introduction to the target cell. Such cell targeting agents can include aptamers, antibodies/fragments, polypeptides (e.g. polypeptides derived from phage display libraries), N-acetylgalactosamine, vitamins, small organic molecules, the like, or a combination thereof. In some examples, the Staufen1-regulating agent can be bound to or carried by a cell penetration agent to facilitate transmembrane permeation of the Staufen1-regulating agent at the target cell. Such cell penetration agents can include polycationic peptides (e.g. polycationic peptides rich in argine and/or lysine, other cell penetrating peptides, etc.), polymers (e.g. PEGylated polycations, polyethyleneimine (PEI), cationic block co-polymers, etc.), dendrimers (e.g. octaguanidine dendrimers, PEI-based dendrimers, etc.), lipids (e.g. cationic lipids, cholesterol, etc.), lysosomal carriers, liposomes, micelles, quantum dots, nanoparticles, the like, or a combination thereof. In still other examples, the Staufen1-regulating agent can be introduced to the target cell via a viral vector. Non-limiting examples of viral vectors that can be employed can include retrovirus, lentivirus, cytomegalovirus, adenovirus, adeno-associated virus, or a combination thereof. In some further examples, a viral vector can be used for long-term expression of the Staufen1-regulating agent in the target cell. Thus, in some examples, the Staufen1-regulating agent can be introduced to a target cell via a viral vector. In other examples, the Staufen1-regulating agent can be introduced to a target cell via a non-viral vector. In still other examples, the Staufen1-regulating agent can be introduced to the target cell without a delivery vector or vehicle. In some further examples, any suitable combination thereof can be employed.

The amount of Staufen1-regulating agent introduced to a target cell can depend on a variety of factors, such as the particular Staufen1-regulating agent being employed, the type and severity of the condition, the dosing regimen, the type of delivery vector (where employed), etc., as will be appreciated by one skilled in the art. Thus, it can be more effective to describe the amount of Staufen1-regulating agent introduced to a target cell by the effect of the amount on the target cell. For example, an effective amount of Staufen1-regulating agent can restore/increase PCP2 mRNA levels in the target cell, CALB1 mRNA levels in the target cell, other mRNAs in the target cell that are metabolized via Staufen1-associated metabolism, or a combination thereof as compared to the levels of these mRNAs prior to or without introducing the Staufen1-regulating agent. In some examples, a level of one or more of these mRNAs can includes by at least 10%, 20%, 30%, 40% or more via introduction of the Staufen1-regulating agent as compared to the level prior to or without introduction of the Staufen1-regulating agent. In some examples, the amount of Staufen1-regulating agent introduced to the target cell can reduce the amount of Staufen1 present in the target cell as compared to the amount of Staufen1 present in the target cell prior to or without introduction of the Staufen1-regulating agent. In some specific examples, the amount of Staufen1 present in the target cell can be reduced by at least 30%, 40%, 50%, 60%, or 70% as compared to Staufen1 levels prior to or without introduction of the Staufen1-regulating agent. In still other examples, where the Staufen1-regulating agent is a mutant ATXN2-inhibiting agent, the amount of Staufen1-regulating agent can reduce a mutant ATXN2 level (or a level of another protein including an elongated polyglutamine tract or similar expansion tract) in the target cell as compared to the mutant ATXN2 level prior to or without administration of the Staufen1-regulating agent. In some specific examples, the amount of mutant ATXN2 (or other protein including an elongated polyglutamine tract or similar expansion tract) present in the target cell can be reduced by at least 30%, 40%, 50%, 60%, or 70% as compared to mutant ATXN2 levels prior to or without introduction of the Staufen1-regulating agent.

The method of controlling, regulating, or normalizing Staufen1 activity in a target cell can include introducing an amount of a Staufen1-regulating agent to a target cell sufficient to reduce Staufen1 activity as compared to Staufen1 activity prior to or without introducing the Staufen1-regulating agent. It is noted that, in this particular method, it is not necessary to reduce the amount of Staufen1 present in the target cell to control, normalize, or minimize Staufen1 activity in the target cell. However, this is also one mechanism of accomplishing reduced Staufen1 activity in the target cell. In other examples, (e.g. via a mutant ATXN2-inactivating agent or mutant ATXN2-inhibiting agent, for example) Staufen1 activity can be reduced by reducing the mutant ATXN2 (or other protein including an elongated polyglutamine tract or similar expansion tract) present in the target cell. This can be accomplished by a number of methods, such as inhibiting expression of the mutant ATXN2 gene (or other protein including an elongated polyglutamine tract or similar expansion tract), editing the mutant ATXN2 gene (or other protein including an elongated polyglutamine tract or similar expansion tract) to a wild-type sequence, the like, or a combination thereof. In still other examples, the activity of Staufen1 can be reduced by introducing a Staufen1-regulating agent that can bind to, degrade, etc. Staufen1 to inactivate or otherwise interfere with the metabolic function of Staufen1 in the target cell. In still other examples, the Staufen1-regulating agent can bind to, degrade, etc. mutant ATXN2 (or other protein including an elongated polyglutamine tract or similar expansion tract) to minimize aggregation of Staufen1 thereto, stabilization of Staufen1, the like, or a combination thereof. In some additional examples, the Staufen1-regulating agent can reduce or block Staufen1 interaction with mRNAs, which can result in altered mRNA expression or abundance.

The same types of Staufen1-regulating agents described herein supra can also be employed in the method of controlling Staufen1 activity in a target cell. Additionally, the same methods of introducing the Staufen1-regulating agent to the target cell as described herein supra can likewise be used in the method of controlling Staufen1 activity. Further, the same or similar amounts as described herein supra may be employed in the method of controlling Staufen1 activity, depending on the particular patient, type and severity of the condition, dosing regimen, Staufen1-regulating agent being employed, etc.

The method of controlling Staufen1 accumulation in a target cell can include introducing an amount of a Staufen1-regulating agent to a target cell sufficient to reduce a concentration of Staufen1 in the target cell as compared to the concentration in the target cell prior to or without introducing the Staufen1-regulating agent. In this particular method, the amount of accumulation of Staufen1 in the target cell can be controlled, normalized, or minimized in a variety of ways. In some examples, the accumulation of Staufen1 in the target cell can be controlled by inhibiting Staufen1 expression. In some additional examples, controlling Staufen1 accumulation can be accomplished by reducing the mutant ATXN2 (or other protein including an elongated polyglutamine tract or similar expansion tract) present in the target cell, such as by inhibiting expression of the mutant ATXN2 gene (or other protein including an elongated polyglutamine tract or similar expansion tract), editing the mutant ATXN2 gene (or other protein including an elongated polyglutamine tract or similar expansion tract) to a wild-type sequence, the like, or a combination thereof. In other examples, controlling Staufen1 accumulation can be accomplished by binding to, degrading, etc. mutant ATXN2 (or other protein including an elongated polyglutamine tract or similar expansion tract) to minimize aggregation of Staufen1 thereto, stabilization of Staufen1, the like, or a combination thereof.

The same types of Staufen1-regulating agents described herein supra can also be employed in the method of controlling Staufen1 accumulation in a target cell. Additionally, the same methods of introducing the Staufen1-regulating agent to the target cell as described herein supra can likewise be used in the method of controlling Staufen1 accumulation in a target cell. Further, the same or similar amounts as described herein supra may be employed in the method of controlling Staufen1 accumulation in a target cell, depending on the particular patient, type and severity of the condition, dosing regimen, Staufen1-regulating agent being employed, etc.

The method of treating a neurodegenerative condition associated with Staufen1-induced dysregulation of RNA metabolism can include administering a therapeutically effective amount of a Staufen1-regulating agent to a subject. It is noted that there are a number of neurodegenerative conditions that can be treated via administration of a therapeutically effective amount of a Staufen1-regulating agent. Non-limiting examples can include spinocerebellar ataxia type 1, spinocerebellar ataxia type 2, spinocerebellar ataxia type 3 (Machado-Joseph disease), spinocerebellar ataxia type 6, spinocerebellar ataxia type 7, spinocerebellar ataxia type 8, spinocerebellar ataxia type 17, Huntington's disease, amyotrophic lateral sclerosis, Alzheimer's disease, frontotemporal dementia, Fragile X syndrome, Mytonic dystrophy, the like, or a combination thereof.

The Staufen1-regulating agent can be administered in a number of ways. Non-limiting examples can include administration via injection (e.g. intravenous, intrathecal, etc.), oral/enteral administration, transmucosal administration, transdermal administration, implantation, or a combination thereof.

Depending on the mode of administration, the particular Staufen1-regulating agent(s) being employed, the type and severity of the condition, the amount of Staufen1-regulating agent being administered, etc., administration can be performed at a variety of frequencies. In some examples, it can be advantageous to administer the Staufen1-regulating agent one or more times per day (e.g. one, two, three, or four times per day). In other examples, it can be advantageous to administer the Staufen1-regulating agent from once every two days to once every seven days, from once per week to once every two weeks, from once every two weeks to once every six weeks, from once every month to once every 12 months, from once every six months to once every 18 months, or a combination thereof.

The amount of Staufen1-regulating agent administered can likewise vary depending on the particular subject being treated, the particular Staufen1-regulating agent(s) being employed, the type and severity of the condition, mode of administration, etc. In some examples, the therapeutically effective amount or dose can be an amount from about 0.001 µg per kg of body weight to about 100 g per kg of body weight. In some additional examples, the therapeutically effective amount or dose can be an amount from about 0.001 µg per kg of body weight to about 0.1 µg per kg of body weight. In other examples, the therapeutically effective amount or dose can be from about 0.1 µg per kg of body weight to about 10 mg per kg of body weight. In still other examples, the therapeutically effective amount or dose can be from about 1 mg per kg of body weight to about 50 mg per kg of body weight. In additional examples, the therapeutically effective amount or dose can be from about 50 mg per kg body weight to about 500 mg per kg body weight. In further examples, the therapeutically effective amount or dose can be from about 500 mg per kg body weight to about 1000 mg per kg body weight. In still further examples, the therapeutically effective amount or dose can be from about 1000 mg per kg body weight to about 10 g per kg body weight. In additional examples, the therapeutically effective amount or dose can be from about 10 g per kg body weight to about 100 g per kg body weight. In some specific examples, the therapeutically effective amount or dose can be an amount from about 0.1 mg to about 1 mg, from about 1 mg to about 15 mg, from about 15 mg to about 50 mg, from about 50 mg to about 100 mg, or from about 100 mg to about 1000 mg. It is noted that these amounts are based on the Staufen1-regulating agent itself and does not account for any ligands, delivery vectors, etc.

In some examples, where the Staufen1-regulating agent is administered via a viral vector, the therapeutically effective amount can be from about $1\times10^1$ to about $1\times10^{20}$ viral particles. In other examples, the therapeutically effective amount can include from about $1\times10^5$ to about $1\times10^{10}$ viral particles. In other examples, the therapeutically effective amount can include from about $1\times10^7$ to about $1\times10^{12}$ viral particles. In yet other examples, the therapeutically effective amount can include from about $1\times10^9$ to about $1\times10^{15}$ viral particles. In further examples, the therapeutically effective amount can include from about $1\times10^{14}$ to about $1\times10^{20}$ viral particles.

The therapeutically effective amount of the Staufen1-regulating agent can depend on the mode of administration, the subject being treated, the type and severity of the condition, the particular Staufen1-regulating agent(s) being employed, etc. In some examples, the therapeutically effective amount of Staufen1-regulating agent can be an amount sufficient to increase PCP2 mRNA levels in the target cell, CALB1 mRNA levels in the target cell, other mRNAs in the target cell that are metabolized via Staufen1-associated metabolism, or a combination thereof as compared to the levels of these mRNAs prior to or without introducing the Staufen1-regulating agent. In some examples, the therapeutically effective amount can be an amount sufficient to increase one or more of these mRNAs by at least 10%, 20%, 30%, 40%, 50%, 60%, 70%, 80%, 90%, or more as compared to the level prior to or without administration of the Staufen1-regulating agent. In some examples, the therapeutically effective amount of the Staufen1-regulating agent can be an amount sufficient to reduce the amount of Staufen1 present in the target cell as compared to the amount of Staufen1 present in the target cell prior to or without administration of the Staufen1-regulating agent. In some specific examples, the therapeutically effective amount can be an amount sufficient to reduce Staufen1 in the target cell by at least 30%, 40%, 50%, 60%, or 70% as compared to Staufen1 levels prior to or without administration of the Staufen1-regulating agent. In still other examples, the therapeutically effective amount of the Staufen1-regulating agent can be an amount sufficient to reduce a mutant ATXN2 level (or a level of another protein including an elongated polyglutamine tract or similar expansion tract) in the target cell as compared to the mutant ATXN2 level prior to or without administration of the Staufen1-regulating agent. In some specific examples, the therapeutically effective amount can be an amount sufficient to reduce mutant ATXN2 (or other protein including an elongated polyglutamine tract or similar expansion tract) in the target cell by at least 30%, 40%, 50%, 60%, or 70% as compared to mutant ATXN2 levels prior to or without administration of the Staufen1-regulating agent (e.g. where the staufen1-regulating agent is a mutant ATXN2-inhibiting agent, for example). Additionally, in some further examples, the therapeutically effective amount can be an amount sufficient to minimize further depletion of motor performance of the subject, restore a portion of previously depleted motor performance, or both.

A therapeutic agent, such as a Staufen1-regulating agent for treating a neurodegenerative condition associated with Staufen1-induced dysregulation of RNA metabolism can include those described elsewhere herein. A therapeutic composition for treating a neurodegenerative condition associated with Staufen1-induced dysregulation of RNA metabolism can include a therapeutically effective amount of Staufen1-regulating agent and a pharmaceutically acceptable carrier. Again, the Staufen1-regulating agent in the therapeutic composition can include those described elsewhere herein.

The therapeutically effective amount of the Staufen1-regulating agent can depend on the mode of administration, the subject being treated, the type and severity of the condition, the particular Staufen1-regulating agent(s) being employed, etc. In some examples, the therapeutically effective amount of Staufen1-regulating agent can be an amount sufficient to increase PCP2 mRNA levels in the target cell, CALB1 mRNA levels in the target cell, other mRNAs in the target cell that are metabolized via Staufen1-associated metabolism, or a combination thereof when administered in an effective dosing regimen as compared to the levels of these mRNAs prior to or without administration of the Staufen1-regulating agent. In some examples, the therapeutically effective amount can be an amount sufficient to increase one or more of these mRNAs by at least 10%, 20%, 30%, 40%, or more when administered in an effective dosing regimen as compared to the level prior to or without administration of the Staufen1-regulating agent. In some examples, the therapeutically effective amount of the Staufen1-regulating agent can be an amount sufficient to reduce the amount of Staufen1 present in the target cell when administered in an effective dosing regimen as compared to the amount of Staufen1 present in the target cell prior to or without administration of the Staufen1-regulating agent. In some specific examples, the therapeutically effective amount can be an amount sufficient to reduce Staufen1 in the target cell by at least 30%, 40%, 50%, 60%, or 70% when administered in an effective dosing regimen as compared to Staufen1 levels prior to or without administration of the Staufen1-regulating agent. In still other examples, the therapeutically effective amount of the Staufen1-regulating agent can be an amount sufficient to reduce a mutant ATXN2 level (or a level of another protein including an elongated polyglutamine tract or similar expansion tract) in the target cell when administered in an effective dosing regimen as compared to the mutant ATXN2 level prior to or without administration of the Staufen1-regulating agent. In some specific examples, the therapeutically effective amount can be an amount sufficient to reduce ATXN2 (or other protein including an elongated polyglutamine tract or similar expansion tract) in the target cell by at least 30%, 40%, 50%, 60%, or 70% when administered in an effective dosing regimen as compared to ATXN2 levels prior to or without administration of the Staufen1-regulating agent.

In some specific examples, the therapeutically effective amount can be an amount from about 1 picomolar (pM) to about 100 millimolar (mM). In some other examples, the therapeutically effective amount can be an amount from about 1 pM to about 100 pM. In still other examples, the therapeutically effective amount can be an amount from about 50 pM to about 500 pM. In yet other examples, the therapeutically effective amount can be an amount from about 300 pM to about 1000 pM. In additional examples, the therapeutically effective amount can be an amount from about 1 nanomolar (nM) to about 50 nM. In still additional examples, the therapeutically effective amount can be from about 10 nM to about 500 nM. In further examples, the therapeutically effective amount can be an amount from about 400 nM to about 1 mM. In still further examples, the therapeutically effective amount can be an amount from about 700 nM to about 10 mM.

In some other specific examples, the therapeutically effective amount can be from about 0.001 µg of Staufen1-regulating agent per gram (g) of therapeutic composition (µg/g) to about 200 mg of Staufen1-regulating agent per gram of therapeutic composition (mg/g). In other examples, the therapeutically effective amount can be from about 0.01 µg/g to about 1 µg/g Staufen1-regulating agent in the therapeutic composition. In some other examples, the therapeutically effective amount can be from about 0.1 µg/g to about 10 µg/g Staufen1-regulating agent in the therapeutic composition. In yet other examples, the therapeutically effective amount can be from about 1 µg/g to about 100 µg/g Staufen1-regulating agent in the therapeutic composition. In still other examples, the therapeutically effective amount can be from about 10 µg/g to about 1 mg/g Staufen1-regulating agent in the therapeutic composition. In some additional examples, the therapeutically effective amount can be from about 100 µg/g to about 10 mg/g Staufen1-regulating agent in the therapeutic composition. In some further examples, the therapeutically effective amount can be from about 1 mg/g to about 100 mg/g Staufen1-regulating agent in the therapeutic composition. It is again noted that the therapeutically effective amounts disclosed herein are generally based on the amount of Staufen1-regulating agent itself without any associated ligands, delivery vehicles, etc., unless otherwise specified.

In some additional specific examples, where the Staufen1-regulating agent is carried by a viral vector, the therapeutically effective amount can include from about $1 \times 10^5$ to about $1 \times 10^{15}$ viral particles per gram of therapeutic composition. In some examples, the therapeutically effective amount can include from about $1 \times 10^5$ to about $1 \times 10^7$ viral particles per gram of therapeutic composition. In some additional examples, the therapeutically effective amount can include from about $1 \times 10^7$ to about $1 \times 10^9$ viral particles per gram of therapeutic composition. In some other examples, the therapeutically effective amount can include from about $1 \times 10^9$ to about $1 \times 10^{11}$ viral particles per gram of therapeutic composition. In yet other examples, the therapeutically effective amount can include from about $1 \times 10^{11}$ to about $1 \times 10^{13}$ viral particles per gram of therapeutic composition. In still other examples, the therapeutically effective amount can include from about $1 \times 10^{13}$ to about $1 \times 10^{15}$ viral particles per gram of therapeutic composition.

The pharmaceutically acceptable carrier can be formulated for a variety of modes of administration. For example, the pharmaceutically acceptable carrier can be formulated to administer the Staufen1-regulating agent via injection (e.g. intravenous, intrathecal, etc.), oral/enteral administration, transdermal administration, transmucosal administration, inhalation, implantation, or the like.

In some examples, the pharmaceutically acceptable carrier can be formulated to provide a therapeutic composition for administration via injection, such as intramuscular injection, intravenous injection, subcutaneous injection, intradermal injection, intrathecal injection, or the like. In such examples, the pharmaceutically acceptable carrier can include a variety of components, such as water, a solubilizing agent, a dispersing agent, a tonicity agent, a pH adjuster, a buffering agent, a preservative, a chelating agent, a bulking agent, the like, or a combination thereof.

In some examples, an injectable therapeutic composition can include a solubilizing or dispersing agent. Non-limiting examples of solubilizing or dispersing agents can include polyoxyethylene sorbitan monooleates, lecithin, polyoxyethylene polyoxypropylene co-polymers, propylene glycol, glycerin, ethanol, polyethylene glycols, sorbitol, dimethylacetamide, polyethoxylated castor oils, n-lactamide, cyclodextrins, caboxymethyl cellulose, acacia, gelatin, methyl cellulose, polyvinyl pyrrolidone, the like, or combinations thereof.

In some examples, an injectable therapeutic composition can include a tonicity agent. Non-limiting examples of tonicity agents can include sodium chloride, potassium chloride, calcium chloride, magnesium chloride, mannitol, sorbitol, dextrose, glycerin, propylene glycol, ethanol, trehalose, phosphate-buffered saline (PBS), Dulbecco's PBS, Alsever's solution, Tris-buffered saline (TBS), water, balanced salt solutions (BSS), such as Hank's BSS, Earle's BSS, Grey's BSS, Puck's BSS, Simm's BSS, Tyrode's BSS, and BSS Plus, the like, or combinations thereof. The tonicity agent can be used to provide an appropriate tonicity of the therapeutic composition. In one aspect, the tonicity of the therapeutic composition can be from about 250 to about 350 milliosmoles/liter (mOsm/L). In another aspect, the tonicity of the therapeutic composition can be from about 277 to about 310 mOsm/L.

In some examples, an injectable therapeutic composition can include a pH adjuster or buffering agent. Non-limiting examples of pH adjusters or buffering agents can include a number of acids, bases, and combinations thereof, such as hydrochloric acid, phosphoric acid, citric acid, sodium hydroxide, potassium hydroxide, calcium hydroxide, acetate buffers, citrate buffers, tartrate buffers, phosphate buffers, triethanolamine (TRIS) buffers, the like, or combinations thereof. Typically, the pH of the therapeutic composition can be from about 5 to about 9, or from about 6 to about 8. However, other suitable pHs can also be desirable.

In some examples, an injectable therapeutic composition can include a preservative. Non-limiting examples of preservatives can include ascorbic acid, acetylcysteine, bisulfite, metabisulfite, monothioglycerol, phenol, meta-cresol, benzyl alcohol, methyl paraben, propyl paraben, butyl paraben, benzalkonium chloride, benzethonium chloride, butylated hydroxyl toluene, myristyl gamma-picolimium chloride, 2-phenoxyethanol, phenyl mercuric nitrate, chlorobutanol, thimerosal, tocopherols, the like, or combinations thereof.

In some examples, an injectable therapeutic composition can include a chelating agent. Non-limiting examples of chelating agents can include ethylenediaminetetra acetic acid, calcium, calcium disodium, versetamide, calteridol, diethylenetriaminepenta acetic acid, the like, or combinations thereof.

In some examples, an injectable therapeutic composition can include a bulking agent. Non-limiting examples of bulking agents can include sucrose, lactose, trehalose, mannitol, sorbitol, glucose, rafinose, glycine, histidine, polyvinyl pyrrolidone, the like, or combinations thereof.

In yet other examples, the pharmaceutically acceptable carrier can be formulated to provide a therapeutic composition for enteral administration, such as via solid oral dosage forms or liquid oral dosage forms. In the case of solid oral dosage forms, the pharmaceutically acceptable carrier can include a variety of components suitable for forming a capsule, tablet, or the like. In the case of a liquid dosage form, the pharmaceutically acceptable carrier can include a variety of components suitable for forming a dispersion, a suspension, a syrup, an elixir, or the like.

In some specific examples, the therapeutic composition can be formulated as a tablet. In such examples, the therapeutic composition can typically include a binder. Non-limiting examples of binders can include lactose, calcium phosphate, sucrose, corn starch, microcrystalline cellulose, gelatin, polyethylene glycol (PEG), polyvinyl pyrrolidone (PVP), hydroxypropyl cellulose, hydroxyethylcellulose, carboxymethyl cellulose (CMC), the like, or combinations thereof.

Where the therapeutic composition is formulated as a tablet, in some examples the therapeutic composition can also include a disintegrant. Non-limiting examples of disintegrants can include crosslinked PVP, crosslinked CMC, modified starch, sodium starch glycolate, the like, or combinations thereof.

In some examples, the tablet can also include a filler. Non-limiting examples of fillers can include lactose, dicalcium phosphate, sucrose, microcrystalline cellulose, the like, or combinations thereof.

In some further examples, the tablet can include a coating. Such coatings can be formed with a variety of materials, such as hydroxypropyl methylcellulose (HPMC), shellac, zein, various polysaccharides, various enterics, the like, or combinations thereof.

In some examples, the tablet can include a variety of other ingredients, such as anti-adherents (e.g. magnesium stearate, for example), colorants, glidants (e.g. fumed silica, talc, magnesium carbonate, for example), lubricants (e.g. talc, silica, magnesium stearate, stearic acid, for example) preservatives, desiccants, and/or other suitable tablet excipients, as desired.

In some other examples, the therapeutic composition can be formulated as a capsule. In such examples, the capsule itself can typically include gelatin, hypromellose, HPMC, CMC, the like, or combinations thereof. A variety of excipients can also be included within the capsule, such as binders, disintegrants, fillers, glidants, preservatives, coatings, the like, or combinations thereof, such as those listed above with respect to tablets, for example, or other suitable variations.

In some examples, the therapeutic composition can be formulated as a liquid oral dosage form. A liquid oral dosage form can include a variety of excipients, such as a liquid vehicle, a solubilizing agent, a thickener or dispersant, a preservative, a tonicity agent, a pH adjuster or buffering agent, a sweetener, the like, or a combination thereof. Non-limiting examples of liquid vehicles can include water, ethanol, glycerol, propylene glycol, the like, or combinations thereof. Non-limiting examples of solubilizing agents can include banzalkonium chloride, benzethonium chloride, cetylpyridinium chloride, docusate sodium, nonoxynol-9, octoxynol, polyoxyethylene polyoxypropylene co-polymers, polyoxyl castor oils, polyoxyl hydrogenated castor oils, polyoxyl oleyl ethers, polyoxyl cetylstearyl ethers, polyoxyl stearates, polysorbates, sodium lauryl sulfate, sorbitan monolaurate, sorbitan monooleate, sorbitan monopalmitate, sorbitan monostearate, tyloxapol, the like, or combinations thereof. Non-limiting examples of thickeners or dispersants can include sodium alginate, methylcellulose, hydroxyethylcellulose, hydroxypropylcellulose, HPMC, CMC, microcrystalline cellulose, tragacanth, xanthangum, bentonite, carrageenan, guar gum, colloidal silicon dioxide, the like, or combinations thereof. The preservative, tonicity agent, pH adjuster or buffering agent can typically be any of those described above with respect to the injectable formulations or other suitable preservative, tonicity agent, pH adjuster or buffering agent. Sweeteners can include natural and/or artificial sweeteners, such as sucrose, glucose, fructose, *stevia*, erythritol, xylitol, aspartame, sucralose, neotame, acesulfame potassium, saccharin, advantame, sorbitol, the like, or combinations thereof, for example.

In yet other examples, the pharmaceutically acceptable carrier can be formulated to provide a therapeutic composition for transdermal or transmucosal administration, such as via the skin, the nasal cavity, the like, or a combination thereof. Where the therapeutic composition is formulated for transdermal or transmucosal administration, the pharmaceutically acceptable carrier can include a variety of components suitable for forming a suspension, dispersion, lotion, cream, ointment, gel, foam, patch, powder, paste, sponge, the like, or a combination thereof. Non-limiting examples can include a solubilizer, an emulsifier, a dispersant, a thickener, an emollient, a pH adjuster, a tonicity agent, a preservative, an adhesive, a penetration enhancer, the like, or a combination thereof. Non-limiting examples of solubilizers and/or emulsifiers can include water, ethanol, propylene glycol, ethylene glycol, glycerin, polyethylene glycol, banzalkonium chloride, benzethonium chloride, cetylpyridinium chloride, docusate sodium, nonoxynol-9, octoxynol, polyoxyethylene polyoxypropylene co-polymers, polyoxyl castor oils, polyoxyl hydrogenated castor oils, polyoxyl oleyl ethers, polyoxyl cetylstearyl ethers, polyoxyl stearates, polysorbates, sodium lauryl sulfate, sorbitan monolaurate, sorbitan monooleate, sorbitan monopalmitate, sorbitan monostearate, tyloxapol, the like, or combinations thereof. In some examples, the solubilizer can also include a hydrocarbon or fatty substance, such as petrolatum, microcrystalline wax, paraffin wax, mineral oil, ceresi, coconut oil, bees wax, olive oil, lanolin, peanut oil, spermaceti wax, sesame oil, almond oil, hydrogenated castor oils, cotton seed oil, soybean oil, corn oil, hydrogenated sulfated castor oils, cetyl alcohol, stearyl alcohol, oleyl alcohol, lauryl alcohol, myristyl alcohol, stearic acid, oleic acid, palmitic acid, lauraic acid, ethyl oleate, isopropyl myristicate, the like, or combinations thereof. In some examples, the solubilizer can include a silicon, such as poly dimethylsiloxanes, methicones, dimethylpropylsiloxanes, methyl phenyl polysiloxanes, steryl esters of dimethyl polysiloxanes, ethoxylated dimethicones, ethoxylated methicones, the like, or combinations thereof.

In some additional examples, the therapeutic composition can include a dispersant and/or thickening agent, such as polyacrylic acids (e.g. Carbopols, for example), gelatin, pectin, tragacanth, methyl cellulose, hydroxylethylcellulose, hydroxypropylcellulose, HPMC, CMC, alginate, starch, polyvinyl alcohol, polyvinyl pyrrolidone, co-polymers of polyoxyethylene and polyoxypropylene, polyethylene glycol, the like, or combinations thereof.

In some examples, the therapeutic composition can include an emollient, such as aloe vera, lanolin, urea, petrolatum, shea butter, cocoa butter, mineral oil, paraffin, beeswax, squalene, jojoba oil, coconut oil, sesame oil, almond oil, cetyl alcohol, stearyl alcohol, olive oil, oleic acid, triethylhexanoin, glycerol, sorbitol, propylene glycol, cyclomethicone, dimethicone, the like, or combinations thereof.

In some examples, the therapeutic composition can include an adhesive, such as acrylic adhesives, polyisobutylene adhesives, silicon adhesives, hydrogel adhesives, the like, or combinations thereof.

In some examples, the therapeutic composition can include a penetration enhancer, such as ethanol, propylene glycol, oleic acid and other fatty acids, azone, terpenes, terpenoids, bile acids, isopropyl myristate and other fatty esters, dimethyl sulphoxides, N-methyl-2-pyrrolidone and other pyrrolidones, the like, or combinations thereof.

The pH adjusters, tonicity agents, and preservatives in the topical, transdermal, or transmucosal therapeutic composition can generally include those pH adjusters and buffering agents, tonicity agents, and preservative agents listed above, or any other suitable pH adjusters, buffering agent, tonicity agent, or preservative for a particular formulation and/or use thereof. In some examples, the therapeutic composition can also include fumed silica, mica, talc, titanium dioxide, kaolin, aluminum glycinate, ethylenediaminetetraacetic acid, fragrances, colorants, other components as described above, the like, or combinations thereof.

In some additional examples, the pharmaceutically acceptable carrier can be formulated for administration via inhalation. In some examples, such formulations can include a propellant, such as hydrofluoralkanes, such as HFA134a, HFA227, or other suitable propellant. In yet other examples, the therapeutic composition can be formulated for administration via nebulization. In either case, the therapeutic composition can also include a variety of solubilizing agents, such as those described above. In other examples, the therapeutic composition can be formulated as a dry powder aerosol. In some examples, the therapeutic composition can include a particulate carrier and/or other particulate excipients, such as lactose, mannitol, other crystalline sugars, fumed silica, magnesium stearate, amino acids, the like, or combinations thereof.

In still additional examples, the pharmaceutically acceptable carrier can be formulated as a biodegradable matrix for implantation into a subject. Specific non-limiting examples of suitable matrix materials can include biodegradable polymers such as PLGA (different ratios of lactic to glycolide content and end groups such as acid or ester termination), PVA, PEG, PLA, PGA, HPMC, hydroxypropylcellulose, sodium carboxymethylcellulose, croscarmellose sodium, polycaprolactone, hyaluronic acid, albumin, sodium chloride block copolymers thereof, and the like. Specific copolymers such as polylactic-polyglycolic acid block copolymers (PLGA), polyglycolic acid-polyvinyl alcohol block copolymers (PGA/PVA), hydroxypropylmethylcellulose (HPMC), polycaprolactone-polyethylene glycol block copolymers, croscarmellose, and the like can be particularly effective. In one aspect, the active agent matrix can be a PLGA having about 45-80% PLA and 55-20% PGA such as about 65% PLA and 35% PGA.

In some examples, the biodegradable matrix can be configured to biodegrade over a period of from about 1 week to about 2 weeks. In yet other examples, the biodegradable matrix can be configured to biodegrade over a period of from about 2 weeks to about 4 weeks. In still other examples, the biodegradable matrix can be configured to biodegrade over a period of from about 4 weeks to about 6 weeks or longer.

In some examples, the therapeutic composition can include a therapeutic agent (e.g. a supplementary therapeutic agent) in addition to the Staufen1-regulating agent. Non-limiting examples can include a dopaminergic agent, a cholinesterase inhibitor, an antipsychotic agent, an analgesic, an anti-inflammatory agent, an inducer of autophagy (e.g. sirolimus, everolimus, tacrolimus, etc.), the like, or a combination thereof.

EXAMPLES

Example 1—Co-Localization of ATXN2 and Staufen1 in SCA2 Fibroblasts and their Physical Interaction An association of Staufen1 and SGs in brain oligodendrocytes and other cultured cells has been described. Because ATXN2 is a component of SGs, it was investigated whether ATXN2 and Staufen1 co-localized under stress condition. SH-SY5Y cells were stressed by heat-shock and the cellular localization of ATXN2 and Staufen1 were studied. Under physiologic condition, ATXN2 and Staufen immunostaining demonstrated that both ATXN2 and Staufen1 are distributed throughout the cytoplasm in SH-SY5Y cells (FIG. 1A). However, when cells were exposed to heat-shock, co-localization of ATXN2 and Staufen1 was observed in distinct cytoplasmic foci resembling SGs (FIG. 1A). Additional co-localization studies were performed using TIA-1 antibodies, a protein marker for SGs. ATXN2 and TIA-1 did co-localize in SGs in cells upon heat-shock treatment (FIG. 1A). Thus, both ATXN2 and Staufen1 were co-localized to SGs under stress conditions (heat-shock).

Figure 1B:
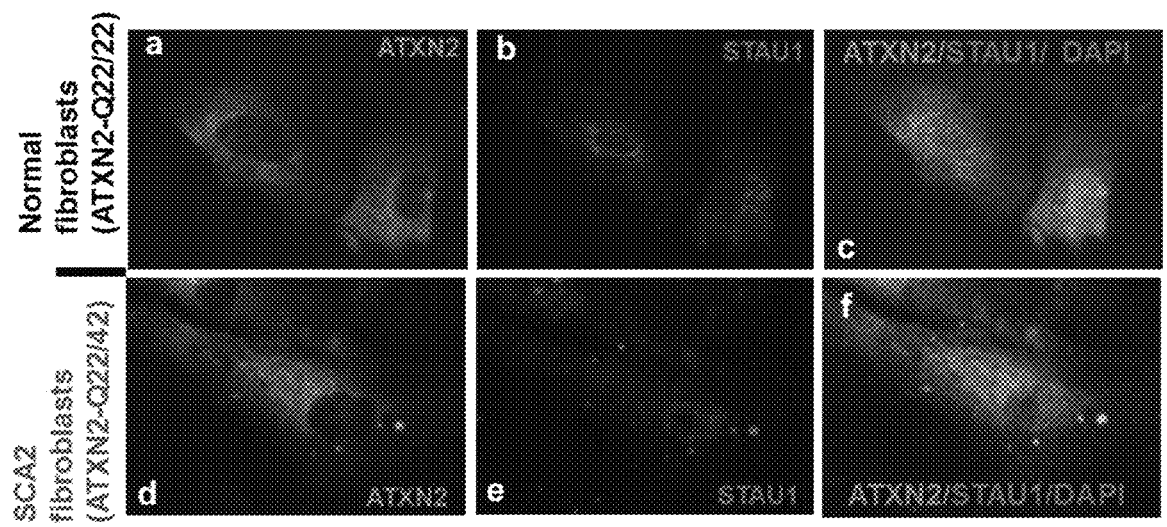
FIG. 1B presents images showing co-localization of ATXN2 and Staufen1 in stress-granule-like aggregates in SCA2-derived skin fibroblasts. Normal and SCA2 fibroblasts were immunostained with anti-ATXN2 (green) and anti-Staufen1 (red) antibodies. Aggregation of ATXN2 (green) and Staufen1 (red) signals are seen in the cytoplasm of SCA2 fibroblasts. Merged images of green and red signals are observed as yellow signals demonstrate that ATXN2 co-localizes with Staufen1.
Figure 1C:
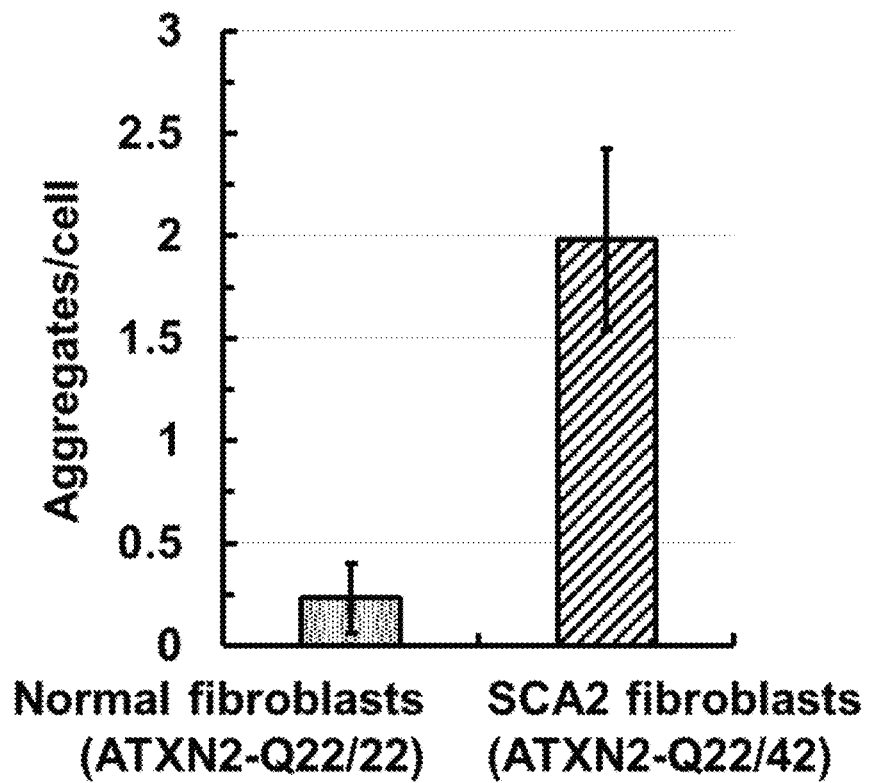
FIG. 1C is a graph of the number of aggregates per cell in normal vs. SCA2 fibroblasts.
Figure 1D:
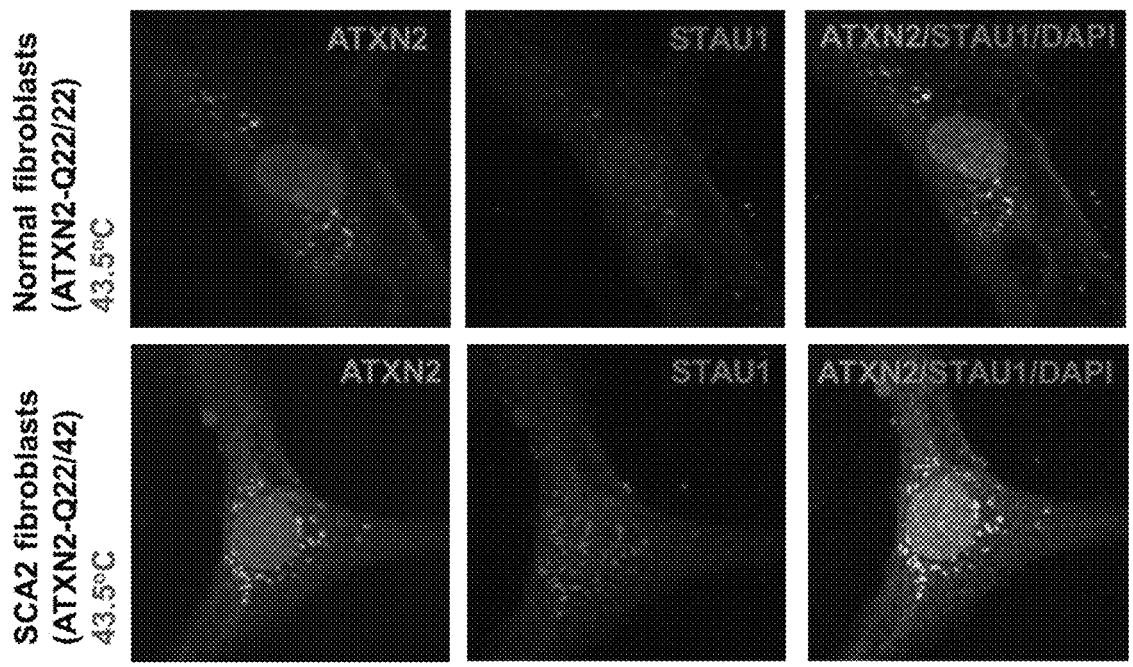
FIG. 1D presents images showing the increment of granules in SCA2 fibroblast under stress condition. Normal and SCA2 fibroblasts were immunostained with ATXN2 and Staufen1 antibodies after heat shock at 43.5° C. for 1 hr. Representative cells showing granules of endogenous ATXN2 (red) and Staufen1 (green) as aggregates by merge images (yellow signals). Nuclei were stained with DAPI.
Figure 1E:
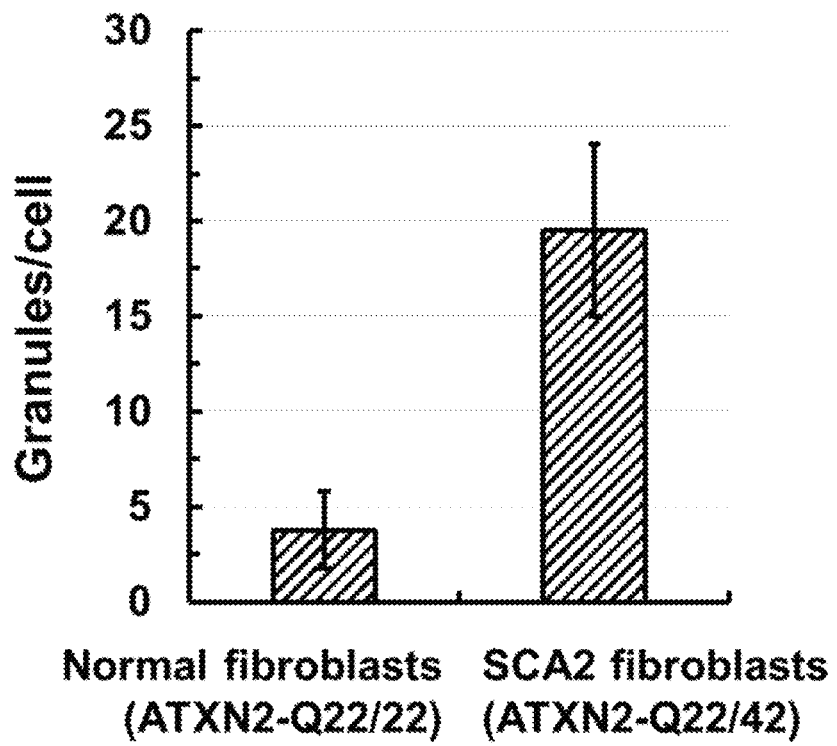
FIG. 1E is a graph of the number of granules per cell in normal vs. SCA2 fibroblasts.

As ATXN2 aggregations are evident in SCA2 brain, the recruitment of Staufen1 in SCA2 fibroblasts under normal and stress conditions was investigated. When normal (ATXN2-Q22/22) and SCA2 fibroblasts (ATXN2-Q22/42) were stained with ATXN2 and Staufen1 antibodies, stress-granule-like aggregates were seen in SCA2 fibroblasts with the co-localization of mutant ATXN2 and Staufen1 but not in normal fibroblasts. By ImageJ, the average area per aggregate was found to be about 15% higher for SCA2 cells over wild type cells (FIGS. 1B-1C). Interestingly, increased number of granules co-localizing ATXN2 and Staufen1 were seen in normal and SCA2 fibroblasts under stress conditions but granule numbers were more pronounced in SCA2 cells (FIGS. 1D and 1E).

Figure 1F:
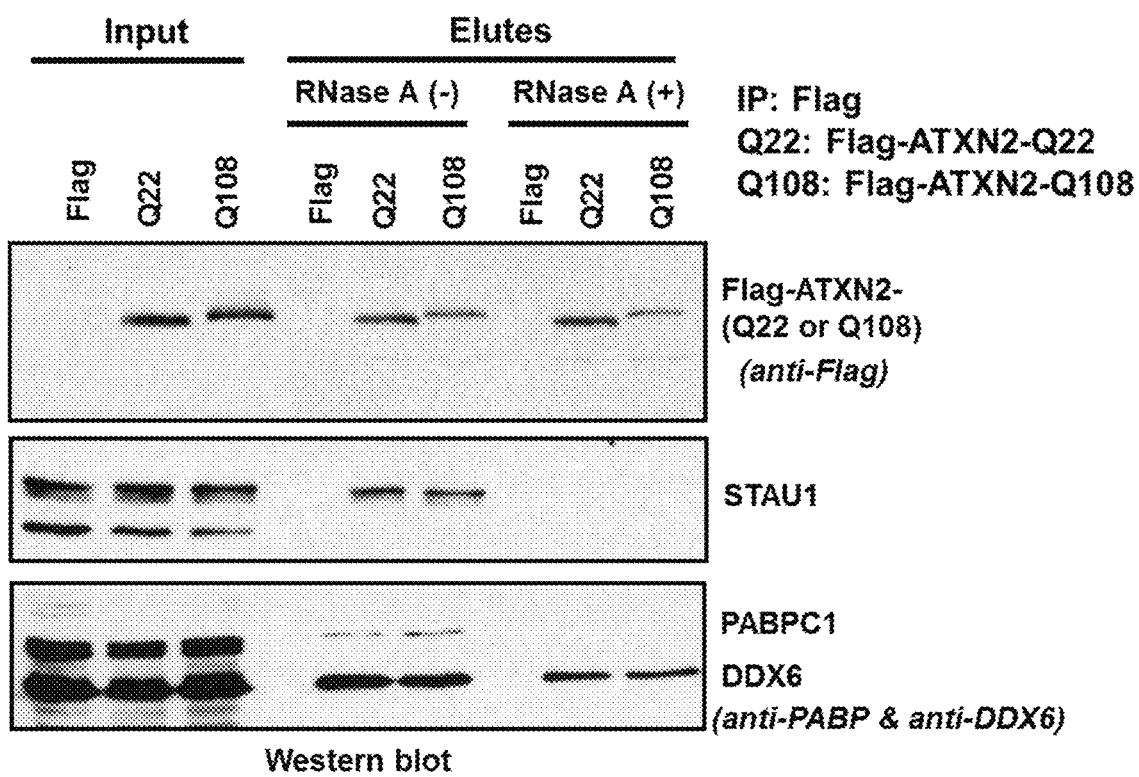
FIG. 1F presents representative blots of three independent experiments showing that Staufen1 interacts with ATXN2 in vivo. Non-RNase or RNase treated SH-SY5Y whole cell extracts expressing Flag-tagged ATXN2-(Q22 or Q108) were subjected to immunoprecipitation with Flag mAb beads. Bound protein complexes were eluted by Flag peptide competition and analyzed by western blot. Staufen1 shows RNA-dependent interaction with wild-type and mutant ATXN2. The immunoprecipitates also show co-IP of DDX6 and PABPC1, both ATXN2 interactors.

Co-localization of ATXN2 and Staufen1 in SG-like aggregates in SCA2 cells predicts physical interaction between these two proteins in vivo. To test this idea, protein immunoprecipitation (IP) experiments were performed in cultured SH-SY5Y cells overexpressing Flag-tagged ATXN2 containing -Q22 or -Q108 repeats. Whole cell extracts (with or without RNase A treatment) were subjected to immunoprecipitation with Flag mAb beads and eluted bound protein complexes were analyzed by western blot. Western blot analyses of the eluted proteins showed expression of Flag-ATXN2 proteins and RNA-dependent interaction of endogenous Staufen1 with Flag-ATXN2-Q22 or Flag-ATXN2-Q108 (FIG. 1F). The immunoprecipitates also showed co-IP of PABPC1 (RNA-dependent) and DDX6 (both RNA- and non-RNA-dependent), which can interact with ATXN2 in vivo. Furthermore, the IP products were analyzed by tandem mass spectrometry and confirmed the authenticity of interaction between ATXN2 and Staufen1. Together these data indicate the physical interaction and co-localization of ATXN2 and Staufen1 in stress-granule-like aggregates in SCA2 cells.

Example 2—Staufen1 Expression in Mouse Cerebellum

Figure 2A:
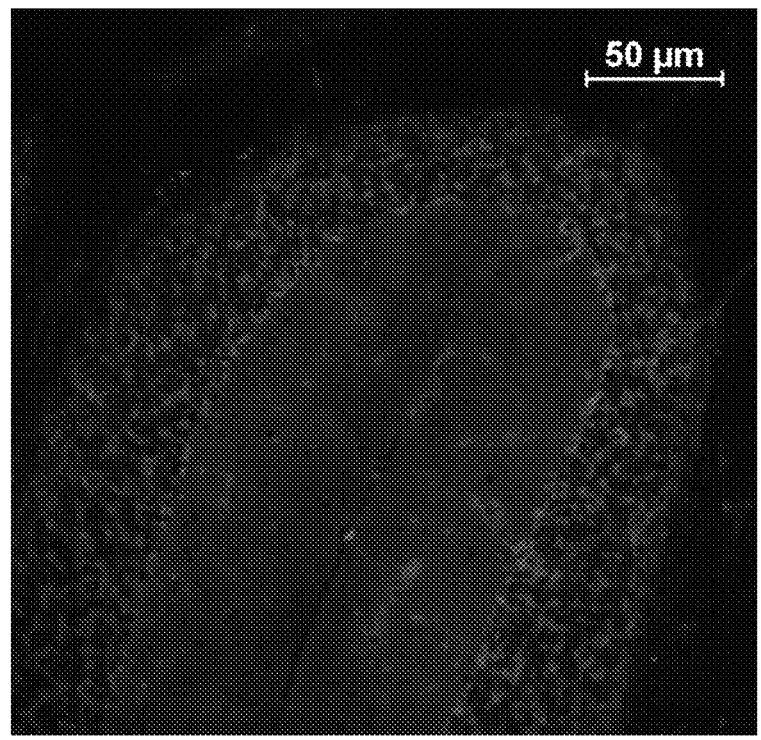
FIG. 2A is a representative micrograph of Staufen1 antibody immunostaining of cerebellum of wild-type mouse at 6 weeks of age. Expression of Staufen1 in cerebellum is observed (20× magnification).
Figure 2B:
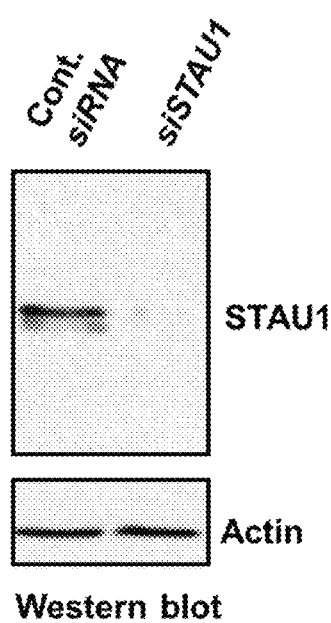
FIG. 2B is a representative blot of silencing achieved for Staufen1. Staufen1 antibody demonstrates specificity to human and mouse endogenous Staufen1. Human SH-SY5Y cells or mouse N2a neuroblastoma cells were transfected with control siRNAs or siRNAs directed against human or mouse Staufen1. For human siStaufen1, SH-SY5Y cells were harvested at 4 days post-transfection. Protein extracts were analyzed by western blot to measure the silencing achieved for Staufen1. Blots were re-probed for β-Actin as an internal loading control. The blot represents one of three independent experiments.
Figure 2C:
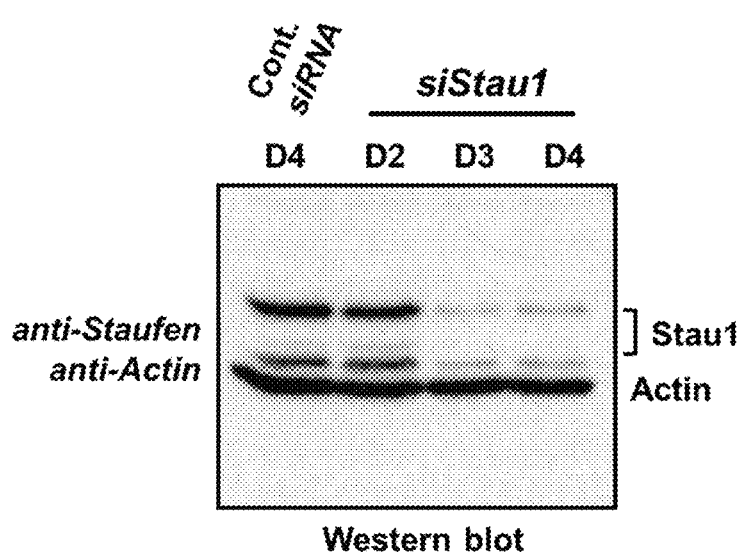
FIG. 2C is a representative blot of silencing achieved for Staufen1. Staufen1 antibody demonstrates specificity to human and mouse endogenous Staufen1. Human SH-SY5Y cells or mouse N2a neuroblastoma cells were transfected with control siRNAs or siRNAs directed against human or mouse Staufen1. For mouse siStaufen1, N2a cells were harvested at 4 days post-transfection. Protein extracts were analyzed by western blot to measure the silencing achieved for Staufen1. Blots were re-probed for β-Actin as an internal loading control. The blot represents one of three independent experiments.

As cerebellar degeneration is prominent in SCA2, the expression of Staufen1 in cerebellar sections in wild-type mice was examined. Immunostaining with anti-Staufen antibody revealed expression of Staufen1 in cerebellum (FIG. 2A). Consistent with this finding, the Human Protein Atlas shows widespread expression of Staufen1 with significant expression level in the cerebellum. The specificity of anti-Staufen antibody was confirmed by measuring endogenous Staufen1 levels in western blot analyses using cell extracts of human SH-SY5Y cells or mouse N2a neuroblastoma cells treated with siRNAs directed against human or mouse Staufen1 (FIGS. 2B and 2C).

Example 3—Steady-State Staufen1 Levels are Increased in SCA2 Patient Cell Lines and BAC-SCA2 Mouse Cerebella Because Staufen1 interacts with ATXN2 and forms aggregates with mutant ATXN2 in SCA2 fibroblasts, steady-state levels of Staufen1 in SCA2-fibroblasts and -lymphoblastoid B (LB) cells were measured. The cells used were (a) four normal skin fibroblasts with Q22 repeats, (b) five SCA2 skin fibroblasts with Q35, Q35, Q35, Q42 and Q45 repeats, (c) two normal LB cells with Q22 repeats, and (d) three SCA2-LB cells with Q40, Q46, Q52 repeats in the ATXN2 gene. Whole cell extracts were prepared from harvested cells by using Laemmli SDS-PAGE sample buffer and analyzed by western blot to measure Staufen1 steady-state levels.

Figure 3A:
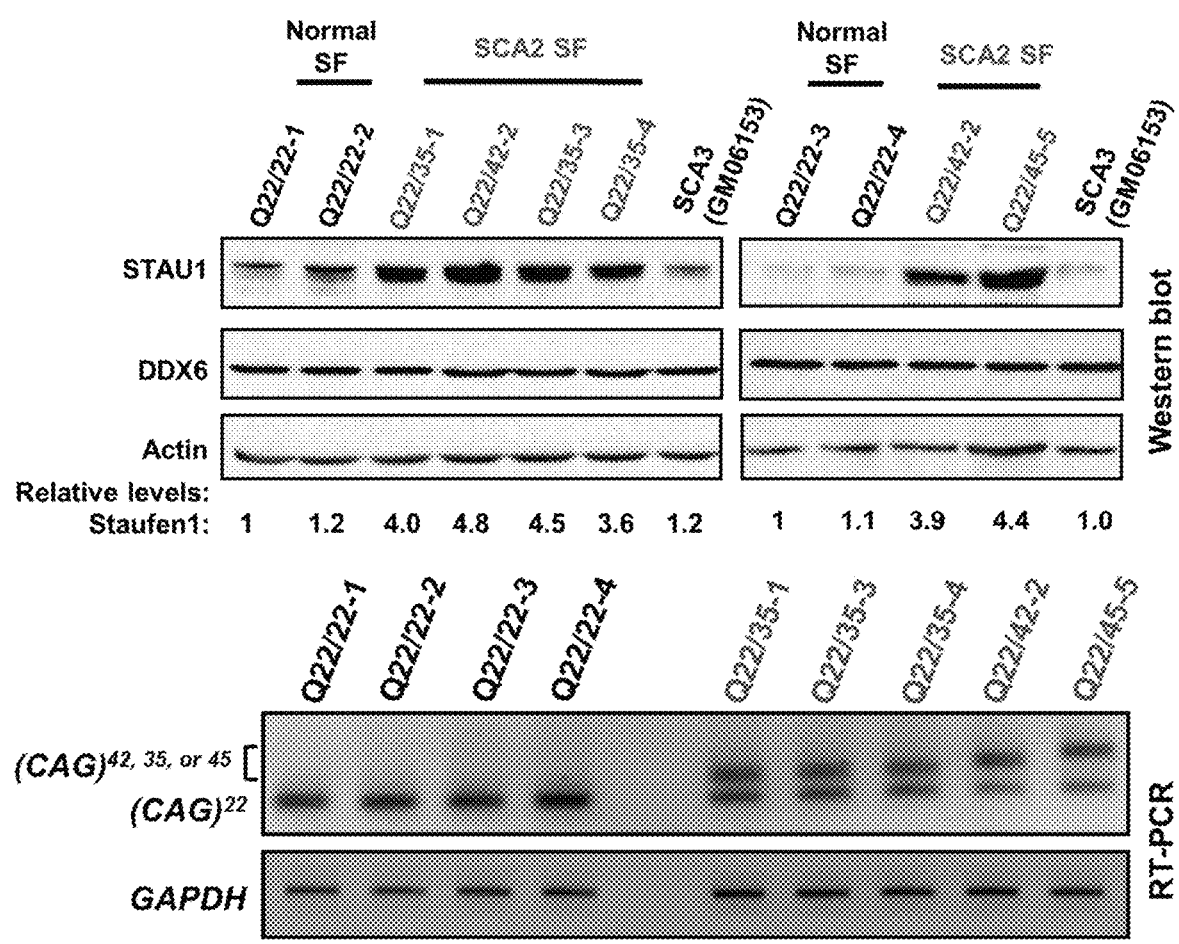
FIG. 3A depicts a Western blot analysis of SCA2 patient-derived skin fibroblasts.
Figure 3B:
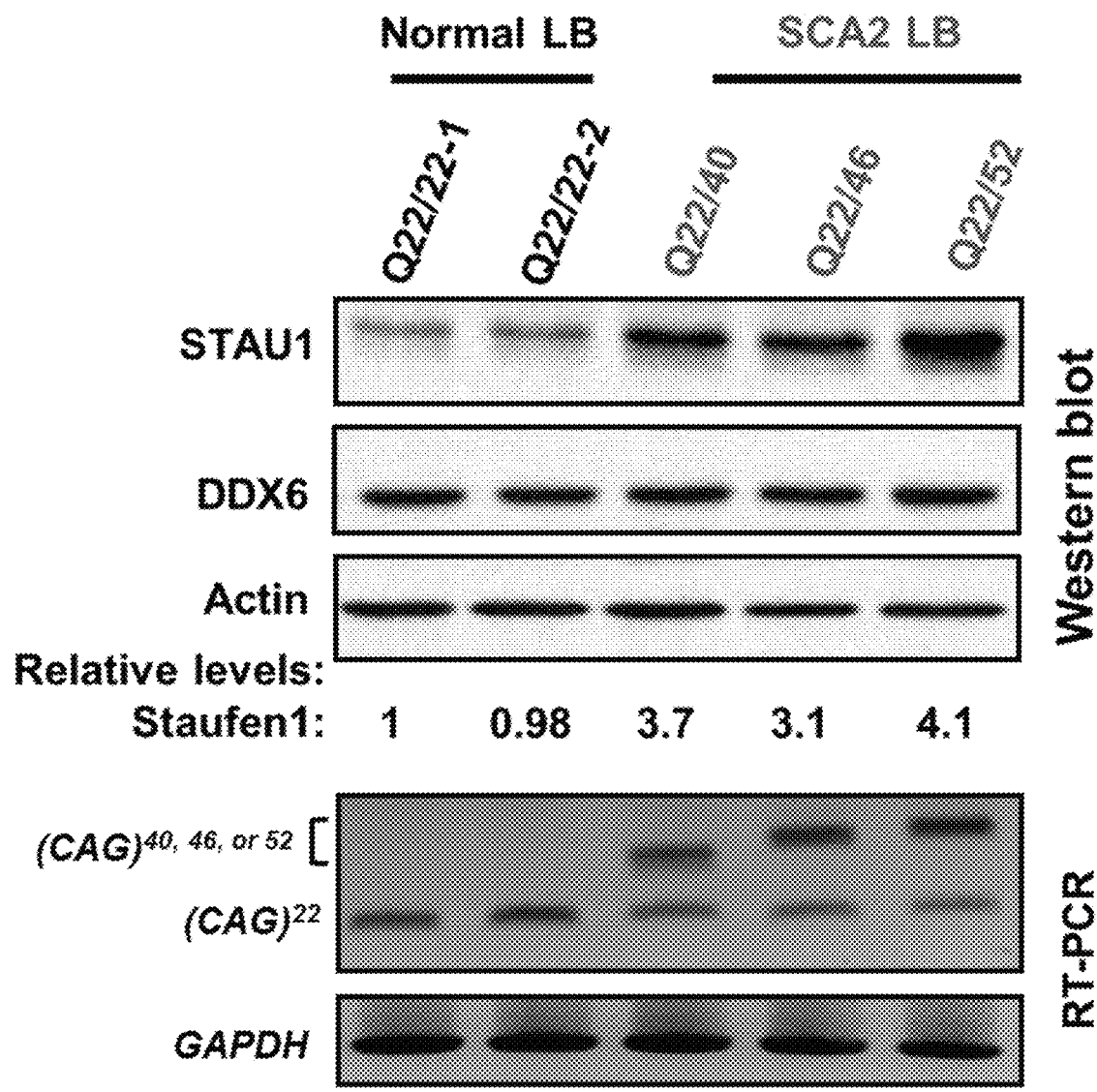
FIG. 3B depicts a Western blot analysis of lymphoblastoid B (LB) cell extracts.
Figure 3C:
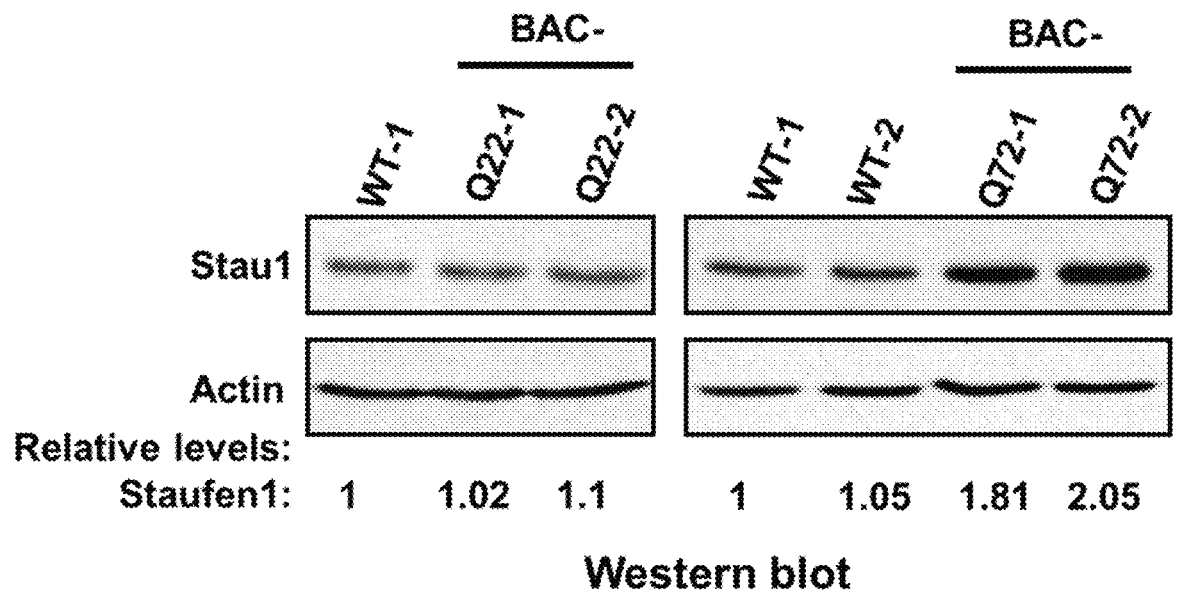
FIG. 3C depicts a Western blot analysis of BAC-Q72 cerebellar extracts (24 weeks of age).
Figure 3D:
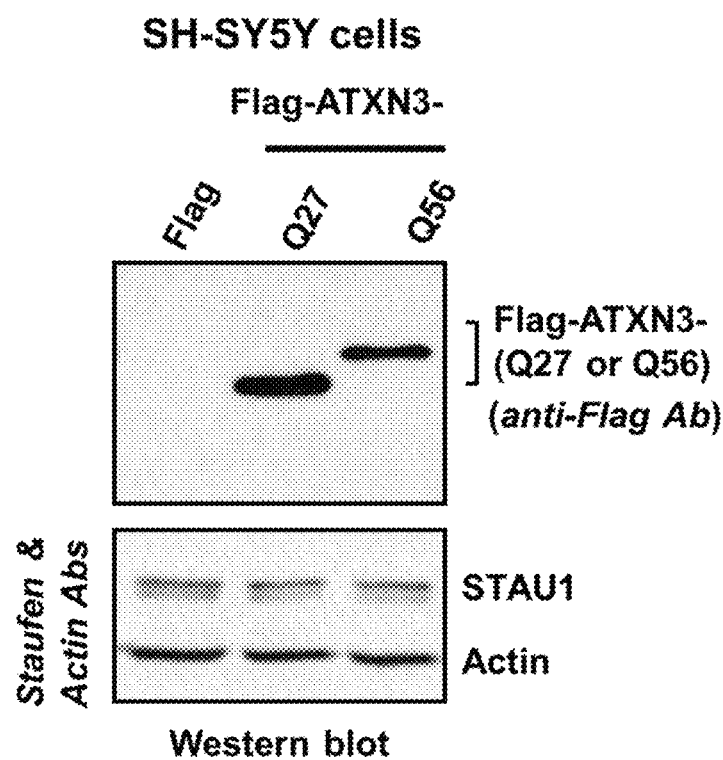
FIG. 3D depicts a Western blot analysis where overexpression of Flag tagged-ATXN3-Q56 in SH-SY5Y cells shows unaltered Staufen1 level compared with wild-type ATXN3.

Steady-state levels of 55-kD Staufen1 isoform were ~4.0, ~4.8, ~4.5, ~3.6 and ~4.9 fold elevated in five SCA2 fibroblasts when compared with four normal fibroblasts. Similarly, three SCA2-LB cells also demonstrated ~3.7, ~3.2 and ~4.1 fold increased level of Staufen1 when compared with two normal LB cells (FIGS. 3A-3B). The level of DDX6 protein, another ATXN2 interactor, was not significantly altered in SCA2-fibroblasts or -LB cells when compared with normal cells. To determine whether Staufen1 levels were affected specifically by the mutant ATXN2 in vivo, the relative levels of Staufen1 were measured by western blotting in cerebellar extracts from BAC-SCA2 mouse models at 24 weeks of age. An increase in abundance of Staufen1 in BAC-Q72 mice (~1.81 and ~2.01 fold) was observed, but the levels were unaltered in BAC-Q22 mice when compared with wild-type mice (FIG. 3C). Conversely, no significant alteration of Staufen1 levels was observed in SCA3 patient fibroblasts or SH-SY5Y cells expressing mutant ATXN3 (Flag-ATXN3-Q56) when compared with control (FIGS. 3A-3B and 3D). Together, these findings established that the level of Staufen1 was elevated in SCA2 disease. The Staufen1 elevation was consistent in the multiple cell lines and in vivo.

Figure 3E:
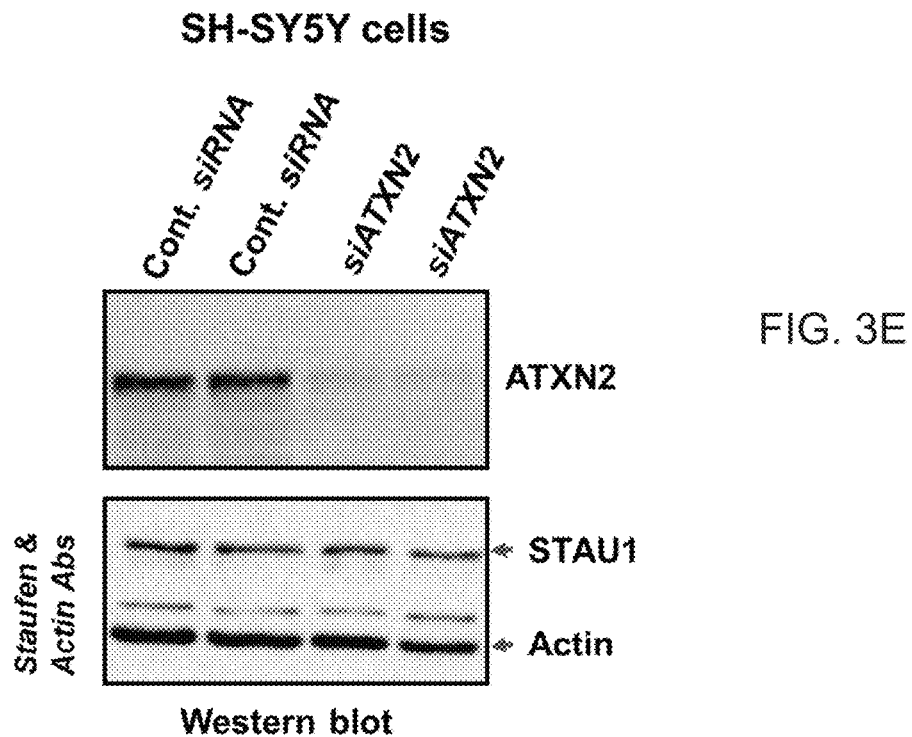
FIG. 3E depicts a Western blot analysis showing increased abundance of Staufen1 in SCA2 cells is unlinked to wild-type ATXN2 loss. SH-SY5Y cells were transfected with siATXN2 RNA and analyzed by western blotting at 4 days post-transfection. Reduced ATXN2 levels do not result in alteration of Staufen1 steady-state levels compared with control siRNA.
Figure 3F:
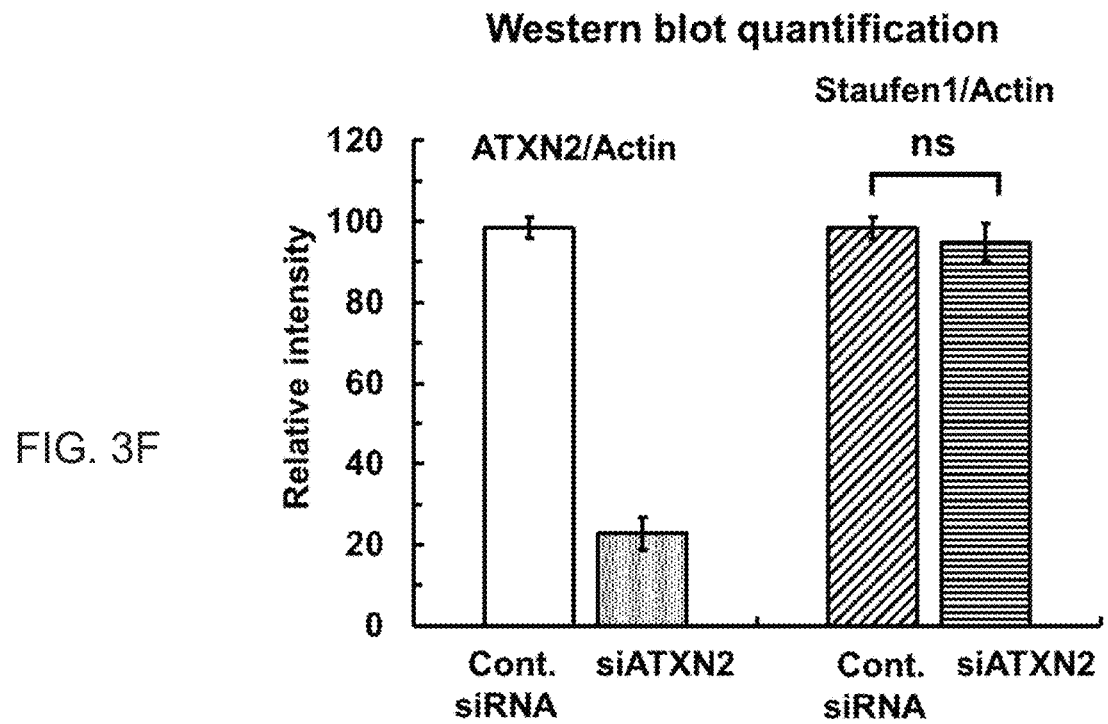
FIG. 3F is a graph of the quantification of abundances on western blots determined densitometrically.
Figure 3G:
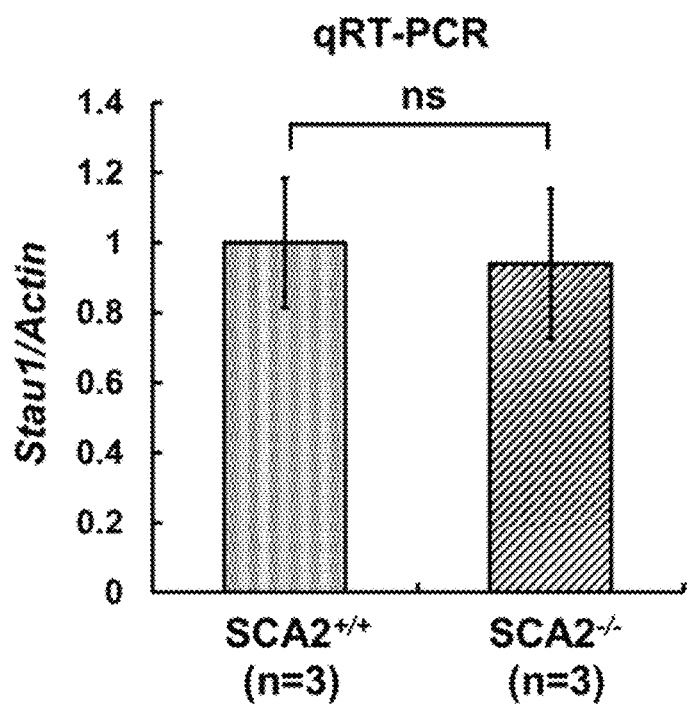
FIG. 3G is a graph of qPCR analyses of cerebellar RNAs showing unaltered Staufen1 transcript levels in SCA2$^{-/-}$ mouse cerebellum compared with SCA2$^{+/+}$ mouse (8 weeks of age).

Next, steady-state Staufen1 at protein and mRNA levels were measured in SH-SY5Y cells in which ATXN2 levels were reduced by siATXN2 and cerebella from Atxn2 knockout mice (8 weeks of age) by qPCR. In these experiments, Staufen1 steady-state protein and mRNA levels were not altered in SH-SY5Y cells with reduced ATXN2 levels or in Atxn2 knock-out mice (FIGS. 3E-3G). Thus, increased abundance of Staufen1 in SCA2 did not result from the functional loss of ataxin-2.

Figure 4A:
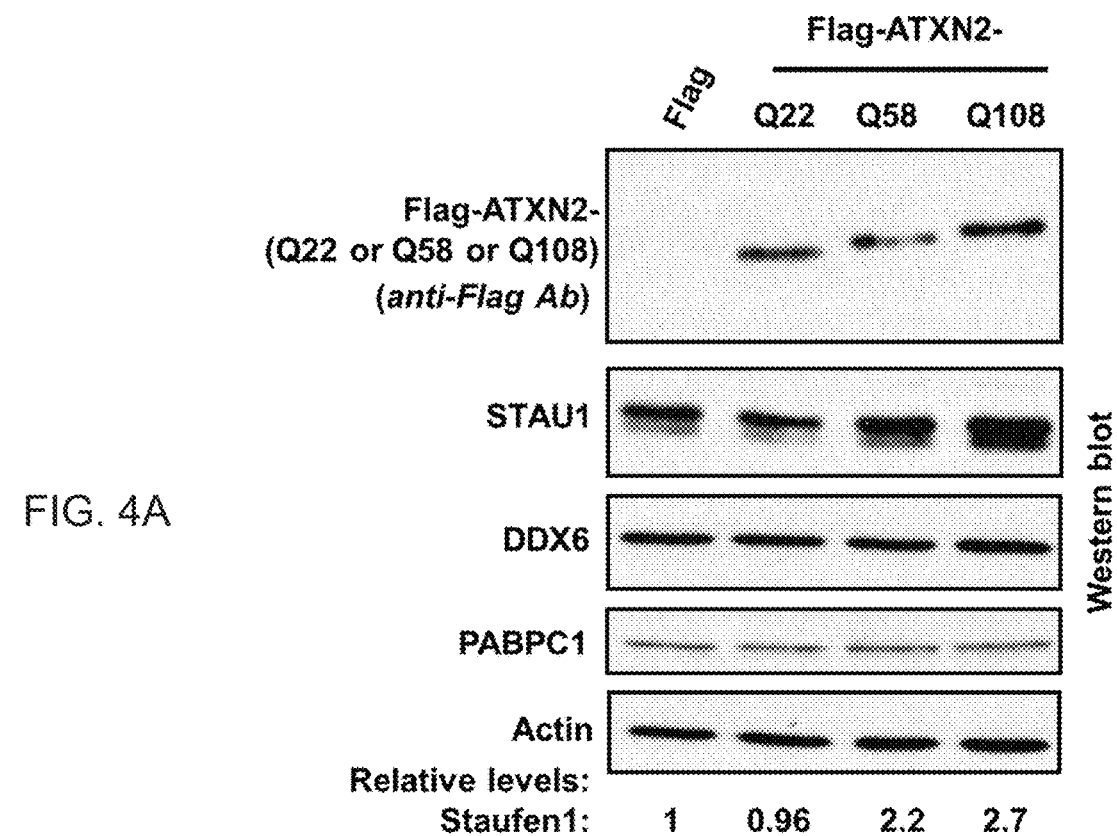
FIG. 4A depicts a Western blot analysis where cells were transfected with plasmids: Flag tagged-ATXN2 containing Q22 or Q58 or Q108 repeats and protein extracts from harvested cells at 48 hr post-transfection to measure Staufen1 steady-state levels.

Example 4—Expression of Mutant ATXN2 in SH-SY5Y Cells Recapitulates Increased Abundance of Staufen1 and Stability of Staufen1 Protein is Increased in SCA2 Fibroblasts To test whether increased Staufen1 levels could be recapitulated upon expression of ATXN2 with long polyQ tracts, steady-state levels of Staufen1 were measured in whole cell extracts of SH-SY5Y cells expressing Flag-tagged ATXN2-Q22 or -Q58 or -Q108. Western blot analyses indicated that expression of ATXN2-Q58 or -Q108 was sufficient to result in increased Staufen1 levels (~2.2 and ~2.7 fold) when compared with ATXN2-Q22 and control (FIG. 4A). To asses if the increased Staufen1 level was not a consequence of selective cellular toxicity of ATXN2-Q58 or -Q108 expression, endogenous PABPC1 and DDX6 levels were measured in those cell extracts by western blot. The levels of PABPC1 and DDX6 were not altered in SH-SY5Y cells expressing ATXN2-Q22 or -Q58 or -Q108 (FIG. 4A). Thus, these data demonstrate that the increased abundance of Staufen1 occurs specifically as a consequence of mutant ATXN2 expression in SH-SY5Y cells.

Figure 4B:
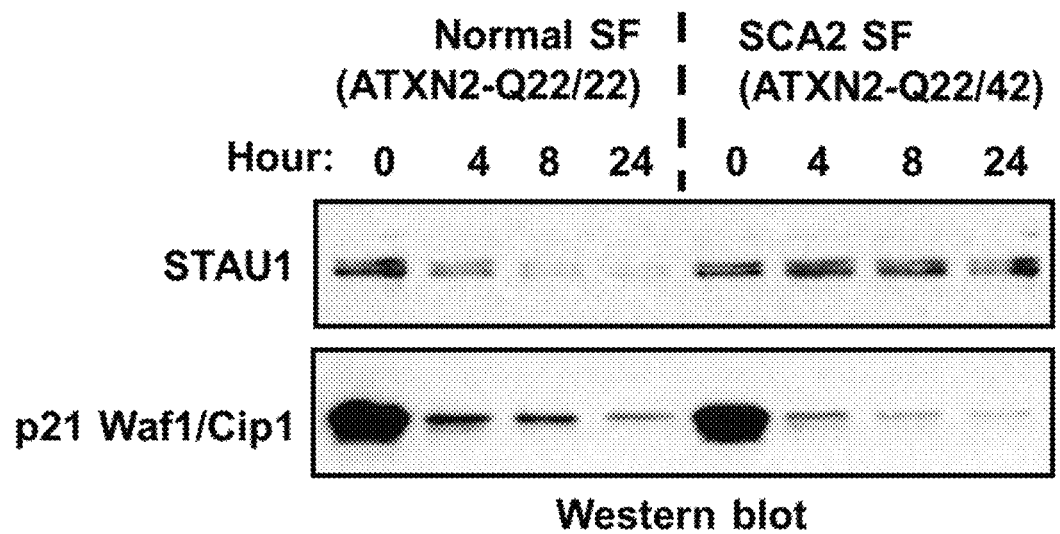
FIG. 4B depicts a blot showing stability of Staufen1 in SCA2 fibroblasts. Normal and SCA2 fibroblasts were exposed to CHX (25 µg/ml) for 0 to 24 hr, and protein extracts were immunoblotted for Staufen1 for each time point. Staufen1 levels are calculated as a percentage of the 0 time point and p21 Waf1/Cip1 protein abundances were measured as an experimental control to verify protein synthesis inhibition by CHX. Staufen1 protein stability is prolonged in SCA2 fibroblasts when compared with normal fibroblasts.
Figure 4C:
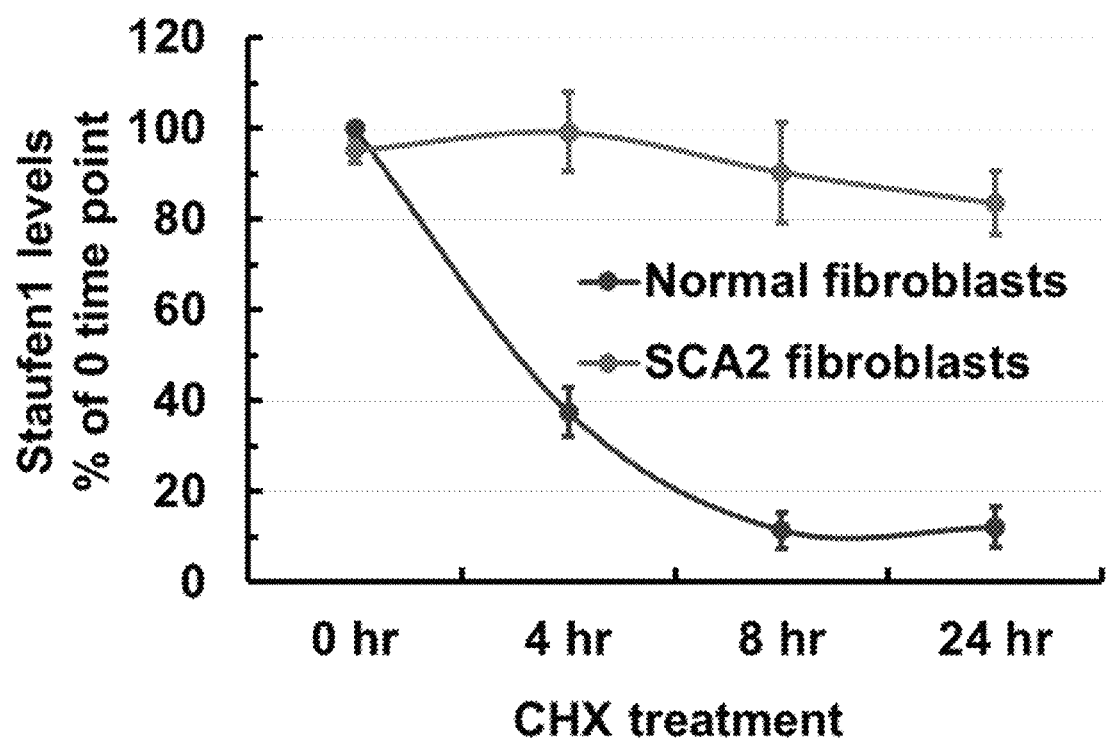
FIG. 4C is a graph of the Quantification of Staufen1 on western blots determined densitometrically.

To identify the underlying mechanism of ATXN2 polyQ expansion-mediated Staufen1 abundance, Staufen1 transcript levels were examined in normal and SCA2 fibroblasts. Results of qPCR data showed little or no differences in Staufen1 transcript levels (data not shown) and suggested that ATXN2 polyQ expansion likely affected Staufen1 protein levels. To test this, comparative protein stability for Staufen1 was measured by cycloheximide (CHX)-chase assay in normal and SCA2 fibroblasts. Relative Staufen1 levels were analyzed from harvested normal and SCA2 fibroblast extracts. (FIGS. 4B and 4C). Western blot analyses demonstrated that Staufen1 levels were reduced 4 hr after CHX treatment in normal fibroblasts. However, in SCA2 fibroblasts, Staufen1 protein expression levels showed relatively little decrease. p21 Waf1/Cip1 levels were also measured as experimental control and demonstrated that p21 Waf1/Cip1 levels were reduced by ~90% at 4 hr after CHX treatment in both normal and SCA2 fibroblasts. Thus, these data suggest that presence of mutant ATXN2 in SCA2 cells increases the stability of Staufen1 protein.

Figure 5A:
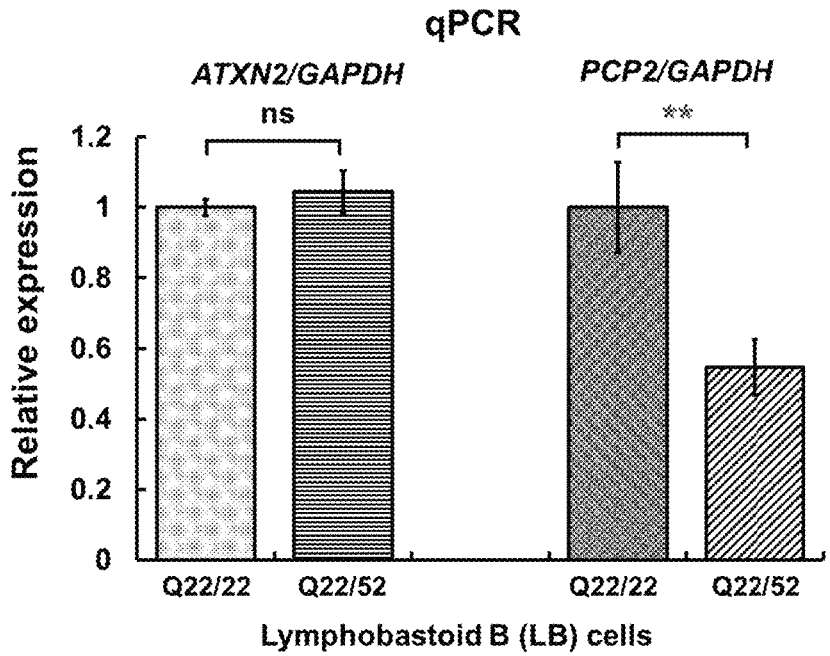
FIG. 5A is a graph showing that SCA2-LB cells demonstrate decreased PCP2 transcripts. qPCR analyses of synthesized cDNAs from SCA2-LB cells show significant reduction of PCP2 mRNA abundance when compared with normal LB cells. ATXN2 mRNA levels remain unchanged in both normal and SCA2-LB cells.
Figure 5B:
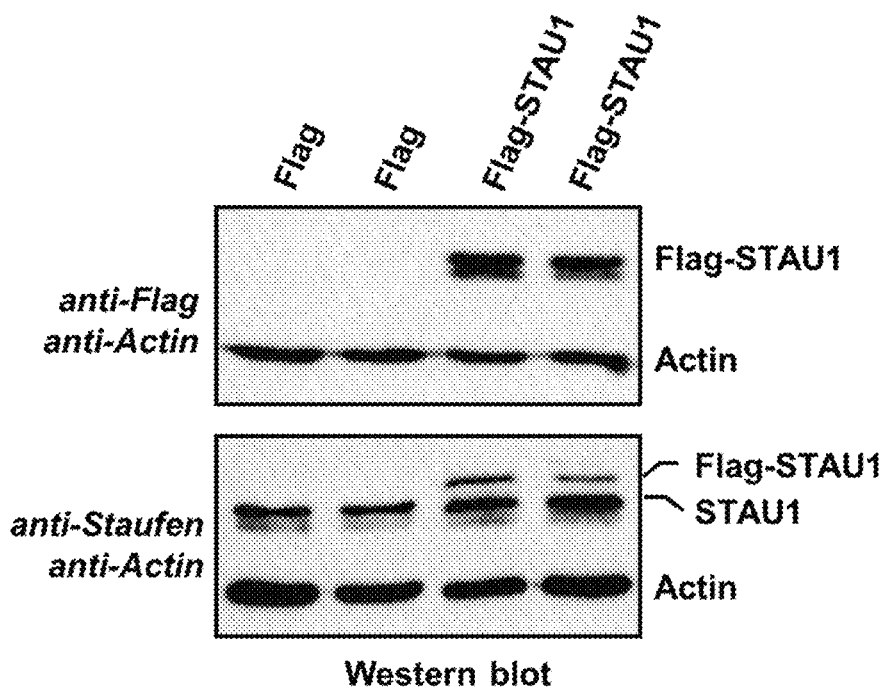
FIG. 5B is a blot showing that increased Staufen1 level in human cell culture independently induces reduction of PCP2 and CALB1 mRNAs abundances. SH-SY5Y cells were transfected with Flag-tagged Staufen1 construct and harvested as two aliquots at 48 hr post-transfection. Protein extracts from one aliquot were immunoblotted to measure the relative expression of Flag-Staufen1.
Figure 5C:
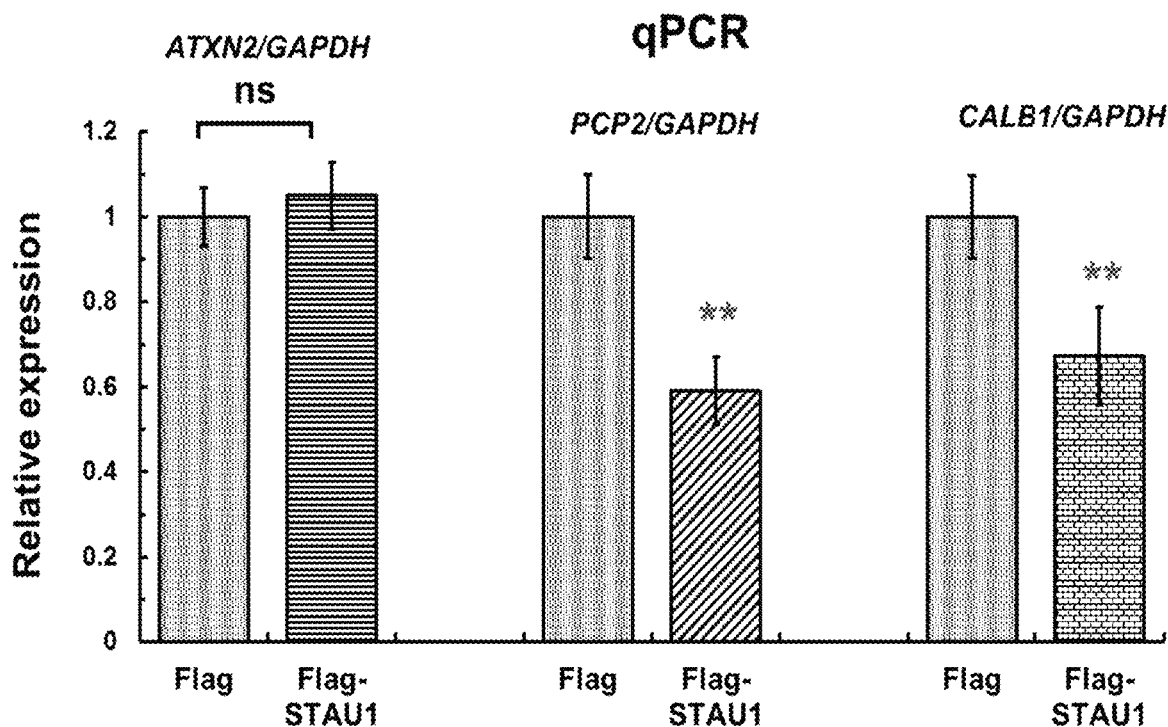
FIG. 5C is a graph of qPCR analyses of synthesized cDNAs from second aliquot showing decreased PCP2 and CALB1 transcripts compared with control transfections. ATXN2 transcripts were not altered upon Staufen1 overexpression. The data are means SD, **p<0.01 (Student's t-test).

Example 5—Elevated Level of Staufen1 Results in Aberrant Processing of RNA Targets To investigate the role of Staufen1 in the development of the aberrant gene expression patterns observed in SCA2, the effect of altered Staufen1 dosage on PCP2 and CALB1 gene expression in SH-SY5Y cells was evaluated and these results were compared with those observed in SCA2-LB cells. First, PCP2 mRNA levels were measured in SCA2-LB (ATXN2-Q22/52) cells using qPCR. CALB1 mRNA could not be analyzed due to undetectable expression levels. The levels of PCP2 mRNA were reduced by 45.4±7.7% in SCA2-LB cells when compared with normal LB (ATXN2-Q22/22) cells (FIG. 5A). In contrast, no alteration of ATXN2 transcript levels was observed in normal and SCA2-LB cells. In separate experiments, the role of increased Staufen1 levels on PCP2 and CALB1 mRNA abundance in SH-SY5Y cells were evaluated. Staufen1 protein was overexpressed in a range that mimicked the changes that are observed in SCA2-fibroblasts or -LB cells. Elevated expression of Staufen1 induced the reduction of PCP2 and CALB1 mRNA levels by 40.8±7.9% and 32.8±8.5%, respectively. To exclude selective cellular toxicity of Staufen1 overexpression, endogenous ATXN2 mRNA levels were measured. The levels of ATXN2 transcript was not altered in SH-SY5Y cells overexpressing Staufen1 (FIGS. 5B and 5C). Thus, these data demonstrate that aberrant gene expression patterns in SCA2 cells can be recapitulated in cell culture model.

Figure 5D:
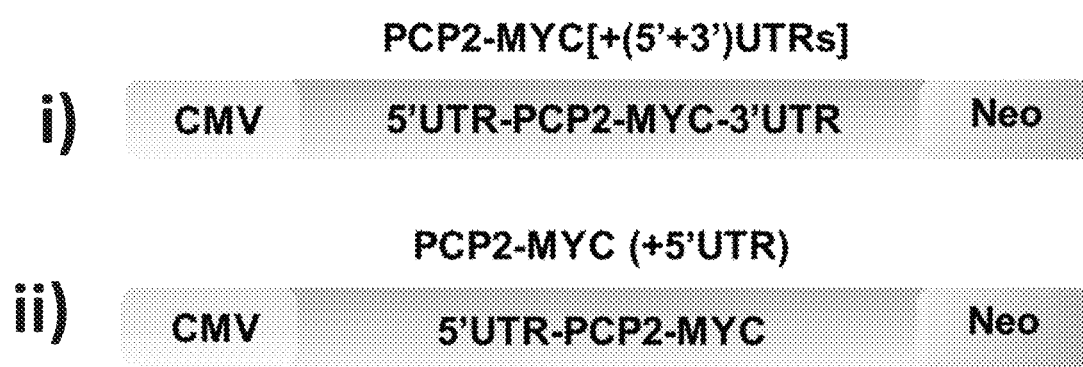
FIG. 5D illustrates a schematic of MYC tagged-PCP2 cDNA[(5'+3')UTRs] (i) and PCP2 cDNA(+5'UTR) (ii).
Figure 5E:
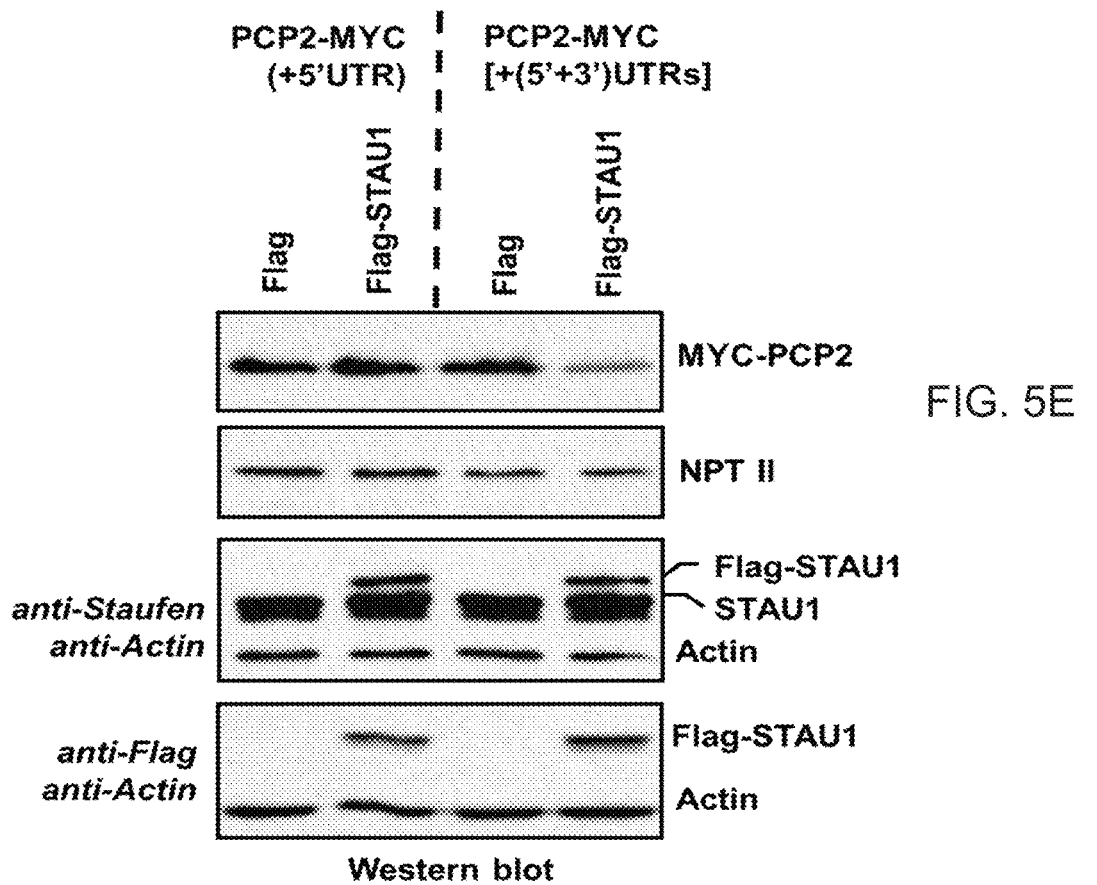
FIG. 5E is a blot showing that increased Staufen1 levels induces repression of PCP2 protein synthesis. MYC tagged-PCP2 cDNA[(5'+3')UTRs] (5Di) PCP2 cDNA(+5'UTR) (5Dii) were cloned under CMV promoter and transfected into short-term hygromycin selected SH-SY5Y cells expressing Flag-Staufen1. Forty-eight hrs post-transfection, western blot analyses show significant reduction of exogenous PCP2 levels in Flag-Staufen1 expressing cells transfected with MYC-tagged PCP2 cDNA[(5'+3')UTRs] (5Di) compared with control. Conversely, increased Staufen1 levels did not show significant regulatory effect on expression of MYC-tagged PCP2 cDNA(−3'UTR) (5Dii) when compared with control.
Figure 5F:
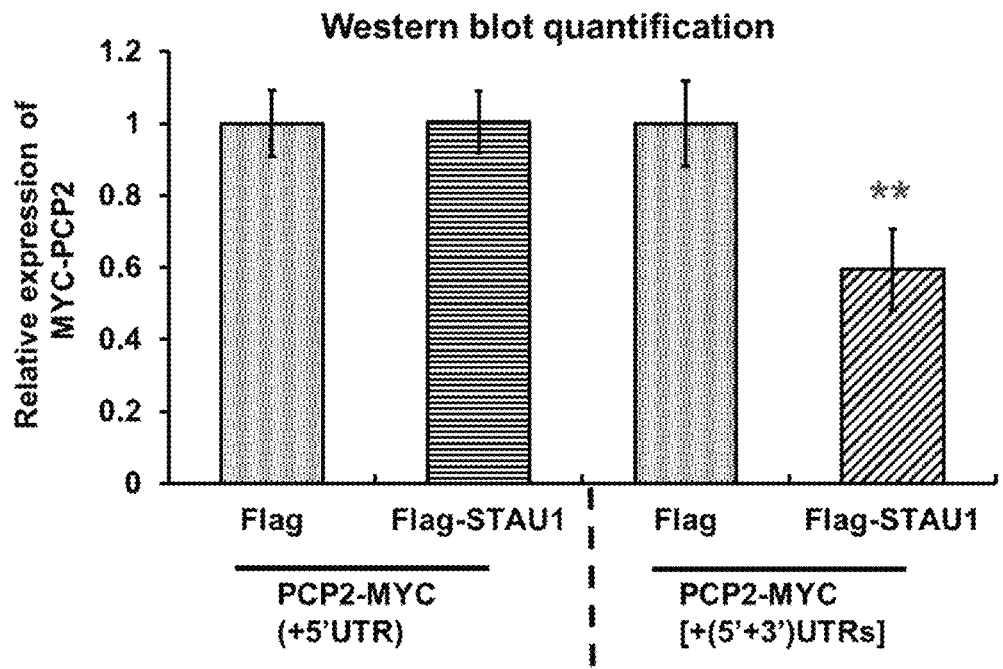
FIG. 5F is a graph of the quantification of MYC-tagged PCP2 on western blots determined densitometrically. To control for equal transfection, Neomycin levels were measured which is expressed as an independent cassette in the MYC-tagged PCP2 plasmids. Blots were re-probed for β-Actin as an internal loading control. The data are means±SD, **p<0.01 (Student's t-test).

Next, PCP2 protein abundance upon increased Staufen1 levels was analyzed. Endogenous PCP2 protein could not be analyzed (due to undetectable expression levels), but exogenous MYC-tagged PCP2 was expressed in short-term hygromycin selected SH-SY5Y cells expressing Flag-tagged Staufen1 and tested regulatory effects of increased Staufen1 levels on exogenous MYC-tagged PCP2 expression. MYC-tagged PCP2 cDNA including 5' and 3' UTRs (i) or excluding 3'UTR (ii) were cloned under the transcriptional control of the CMV promoter. Forty-eight hours post-transfection, western blot analyses revealed that the exogenous PCP2 levels were significantly reduced in Staufen1 expressing cells transfected with MYC-tagged PCP2 cDNA[(5'+3')UTR] (i) when compared with control. However, increased Staufen1 levels did not show inhibitory effect on expression of MYC-tagged PCP2 cDNA(+5'UTR) (ii) compared with control (FIGS. 5D-5F). To control for equal transfection, Neomycin protein levels were monitored, which was expressed as an independent cassette in MYC-tagged PCP2 plasmids. Thus, these data suggest that Staufen1 regulates the expression of PCP2 via its 3'UTR.

Example 6—Staufen1 Interacts with PCP2 and CALB1 RNAs

Figure 6A:
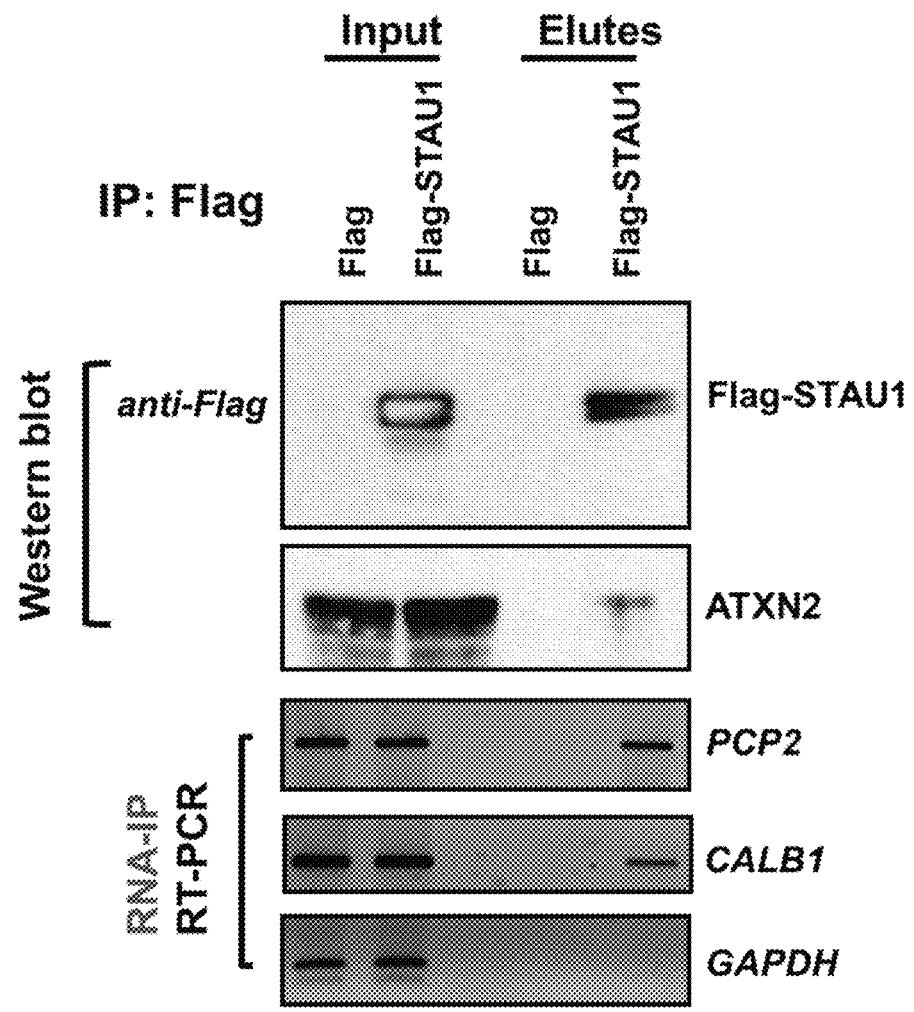
FIG. 6A is a blot where non-RNase treated SH-SY5Y whole cell extracts expressing Flag or Flag-Staufen1 were subjected to immunoprecipitation with Flag mAb beads. Bound protein-RNA complexes were eluted by Flag peptide competition and IP products were divided equally into two parts and subjected to western blot and RT-PCR/qPCR analyses. Western blot analyses of the eluted proteins shows co-IP of endogenous ATXN2 with Flag-Staufen1. RT-PCR analyses of the second aliquot shows that Flag-Staufen1 pulls down PCP2 and CALB1 mRNAs but not GAPDH mRNA.

Reduction of PCP2 and CALB1 mRNAs, and a concomitant repression of PCP2 expression at protein levels by the elevated Staufen1 level predict that Staufen1 might interact with subset of mRNAs and regulate their expressions. To identify Staufen1 targets, protein-RNA immunoprecipitation (IP) experiments were performed in cultured SH-SY5Y cells overexpressing Flag-tagged Staufen1. Non-RNase A treated whole cell extracts were subjected to immunoprecipitation with Flag mAb beads and eluted protein-RNA complexes were divided as two aliquots for western blot and RT-PCR analyses. Flag-Staufen1 showed co-IP of ATXN2 (FIG. 6A). RT-PCR analyses from the second aliquot revealed that Flag-Staufen1 pulled down PCP2 and CALB1 mRNAs but not control GAPDH mRNA (FIG. 6A).

Figure 6B:
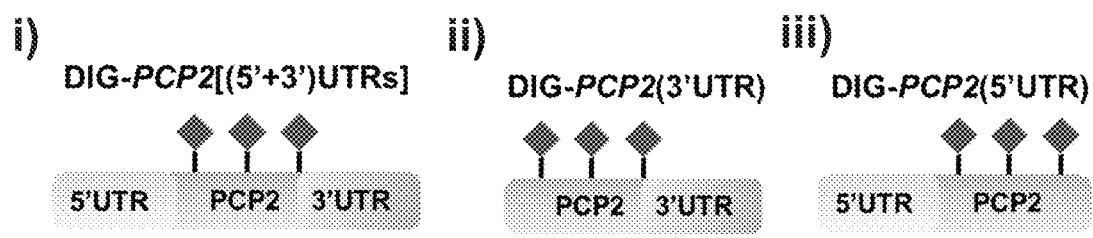
FIG. 6B depicts a schematic of DIG-labelled human PCP2 transcripts: PCP2 [(5'+3)UTR] (i), PCP2 (3'UTR) (ii) and PCP2 (5'UTR) (iii).
Figure 6C:
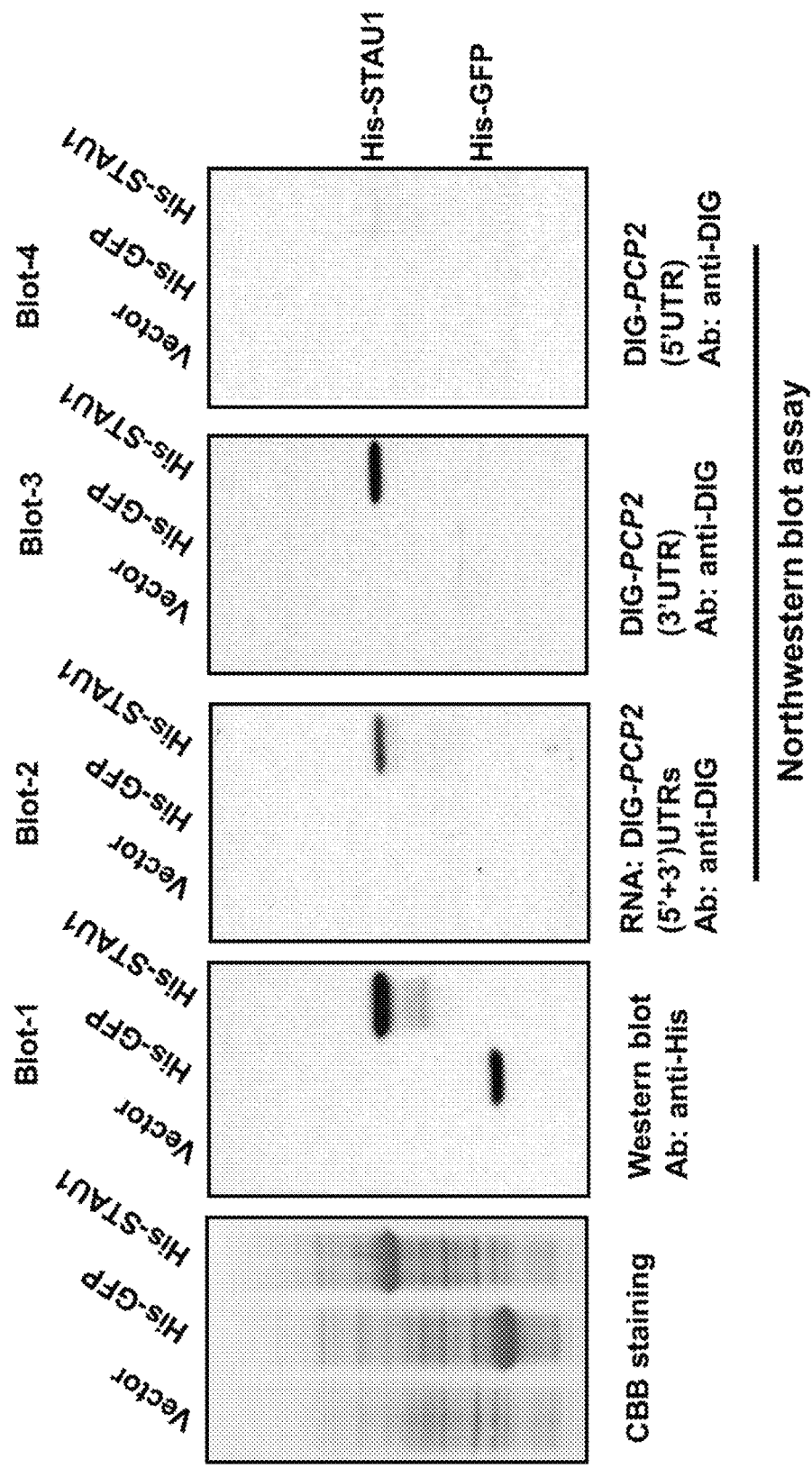
FIG. 6C is a blot of extracts from BL21<DE3> bacteria transformed with pET vectors containing His tagged-Staufen1, -GFP or pET that were run on SDS-PAGE and stained with coomassie brilliant blue or western blotted with anti-His antibody (blot 1). For northwestern blot assay, bacterial protein extracts: pET, His-GFP or His-Staufen1 were run on SDS-PAGE and transferred onto PVDF membrane. The membranes were re-natured and hybridized with DIG-labelled PCP2 RNA probes as indicated. Following anti-DIG antibody staining, the signals were detected by Western Chemiluminescent method. The results demonstrate Staufen1 binds directly to PCP2 RNAs: (5'+3')UTRs (i) (blot 2) or (3'UTR) (ii) (blot 3) but not to PCP2(5'UTR) RNA (blot 4). His-GFP does not show any interactions with PCP2 RNA probes. The blot represents one of three independent experiments.

To confirm direct binding between Staufen1 and its targets, northwestern blotting experiments were performed using bacterially expressed recombinant His-tagged Staufen1 protein and in vitro transcribed DIG-labelled PCP2 RNA probes. Several probes were generated that allowed testing of which parts of PCP2 RNA interacted with Staufen1. The probes used were: DIG-PCP2[(5'+3')UTR)] (i), DIG-PCP2(3'UTR) (ii), and DIG-PCP2(5'UTR) (iii) (FIG. 6B). Staufen1 showed binding toward PCP2[(5'+3') UTR)] (i) or PCP2(3'UTR) (ii) RNAs but not to PCP2 (5'UTR) (iii) RNA, thereby showing the specificity of the interaction (FIG. 6C). Together, these results demonstrate that both in vivo and in vitro, Staufen1 interacts with PCP2 mRNA through 3'UTR.

Example 7—Silencing of Staufen1 or Mutant ATXN2 Restores PCP2 mRNA Levels in SCA2 Cells The siRNAs used in this study were: All Star Negative Control siRNA (Qiagen Inc., USA; Cat #1027280), siATXN2 [Hs_ATXN2_2, (Qiagen Inc., USA; Cat #SI00308196), human siSTAU1: 5' CCUAUAACUACAA-CAUGAGdTdT-3' and mouse siStau1: 5'-CAACUGUAC-UACCUUUCC AdTdT-3'. Staufen1 siRNA oligonucleotides were synthesized by Invitrogen Inc., USA. The oligonucleotides were deprotected and the complementary strands were annealed.

SCA2-fibroblasts or -LB cells demonstrated increased abundance of Staufen1 (FIGS. 3A-3G). The recapitulation of increased Staufen1 levels by the expression of mutant ATXN2 in the BAC-SCA2 mouse model or in a cell culture model, and dysregulation of RNA processing by the overexpression of Staufen1 in cell culture (FIGS. 4A-4C and 5A-5F) predict that silencing of staufen1 might result in restoration of normal levels of Staufen1-target RNAs.

Figure 7A:
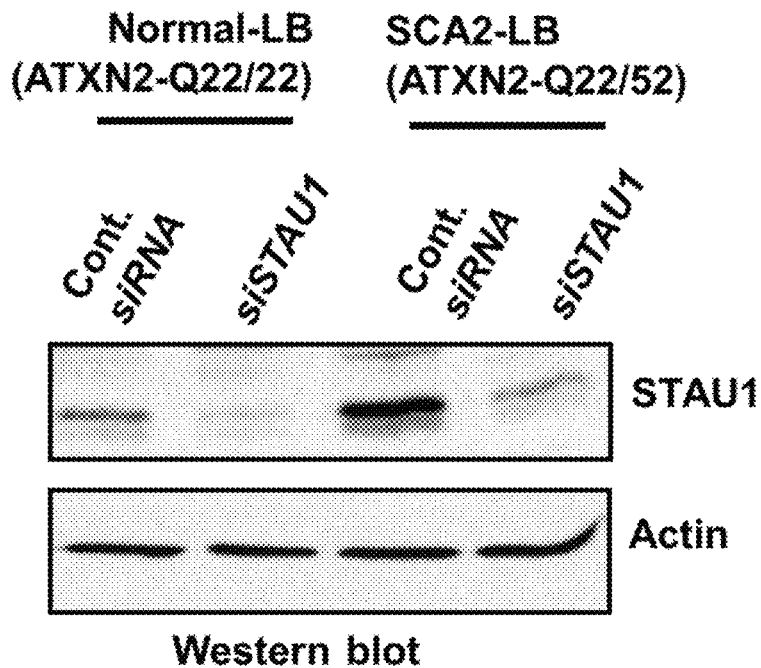
FIG. 7A is a blot of Normal (ATXN2-Q22/22) and SCA2-LB (ATXN2-Q22/52) cells that were electroporated with siSTAU1 and harvested as two aliquots for protein and RNA analyses after 4 days post-electroporation. Protein extracts from one aliquot were immunoblotted for Staufen1.
Figure 7B:
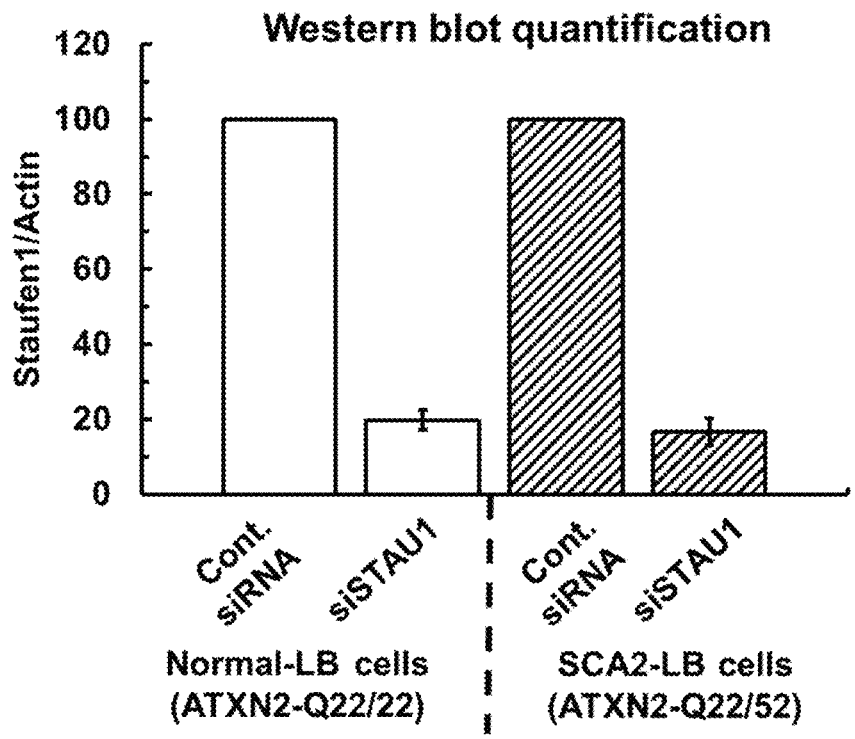
FIG. 7B is a graph of Western blot quantification determined densitometrically of Staufen1/Actin in normal LB cells and SCA2-LB cells.
Figure 7C:
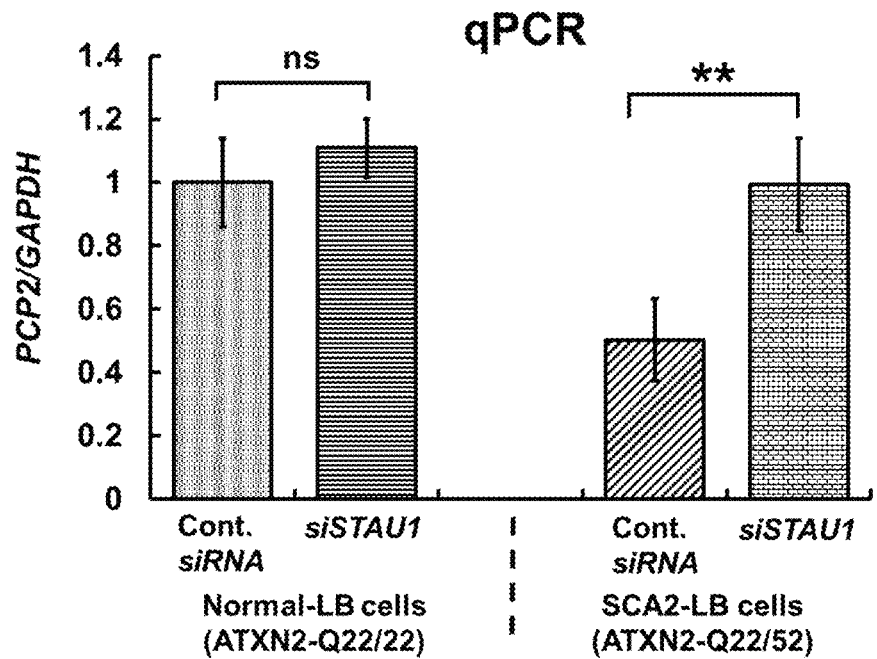
FIG. 7C is a graph of isolated RNAs from the second aliquot that were subjected to qPCR analyses to measure PCP2 transcript levels. Staufen1 depletion does prevent PCP2 transcript expression defects in SCA2-LB cells but not showing significant PCP2 transcript alterations in normal cells when compared with control siRNAs.
Figure 7D:
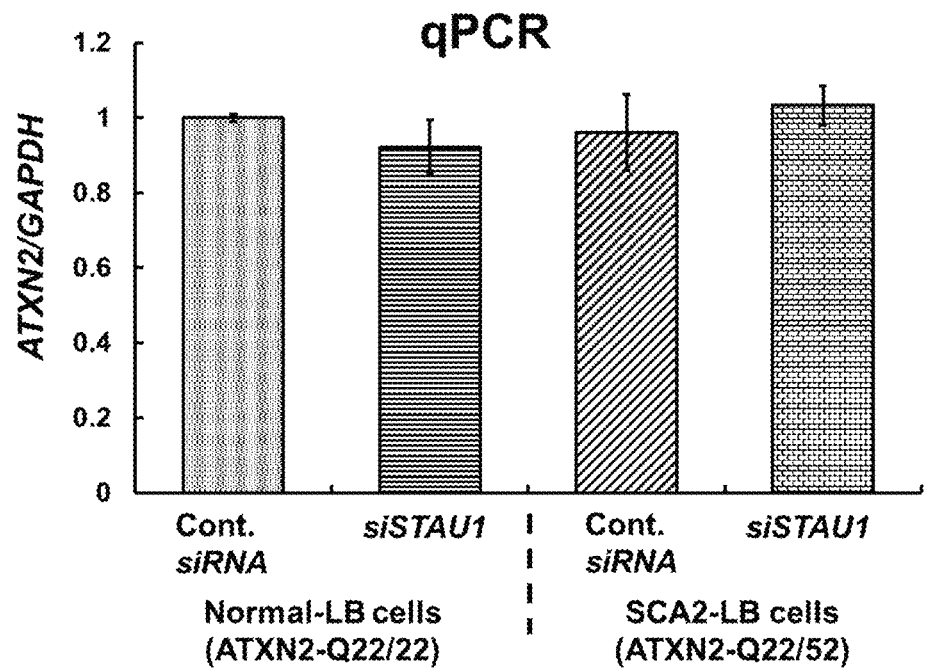
FIG. 7D is a graph showing silencing of Staufen1 does not show alteration of ATXN2 transcript steady-state levels in normal and SCA2-LB cells as judged by qPCR analyses.
Figure 7E:
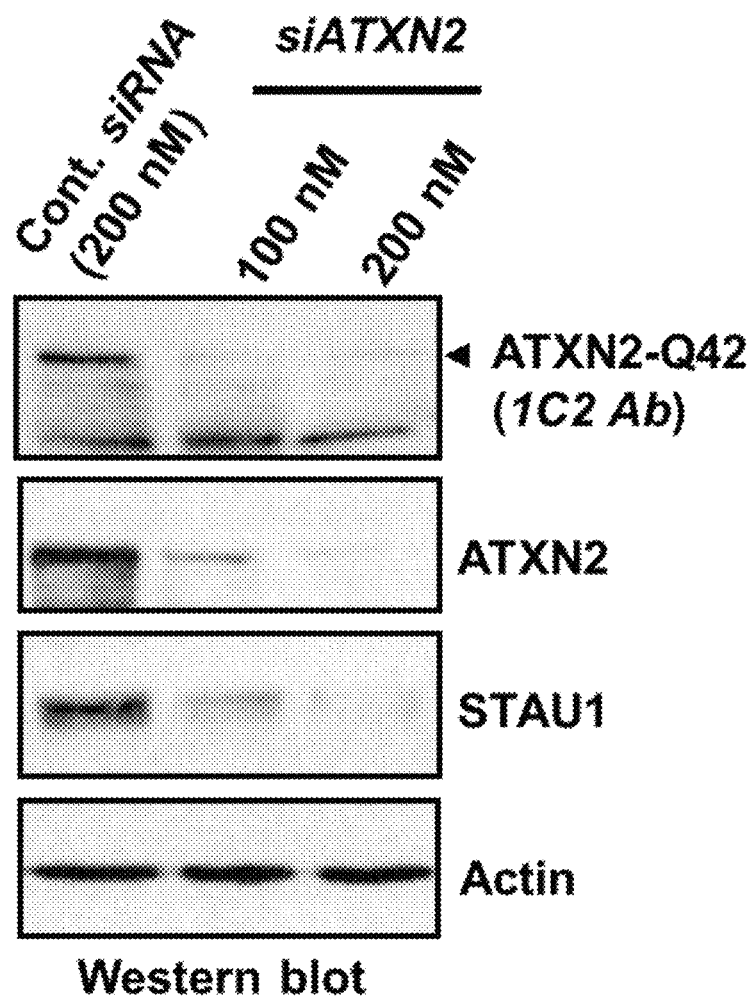
FIG. 7E is a blot of SCA2-fibroblasts (ATXN2-Q22/42) cells that were transfected or electroporated with siATXN2 at dose dependent fashion and harvested as two aliquots for protein and RNA analyses after 4 days post-transfection/electroporation. Protein extracts from one aliquot were immunoblotted for ATXN2 and Staufen1 and showing significant reductions of Staufen1 abundance upon depletion of ATXN2 dosages when compared with control siRNA.
Figure 7F:
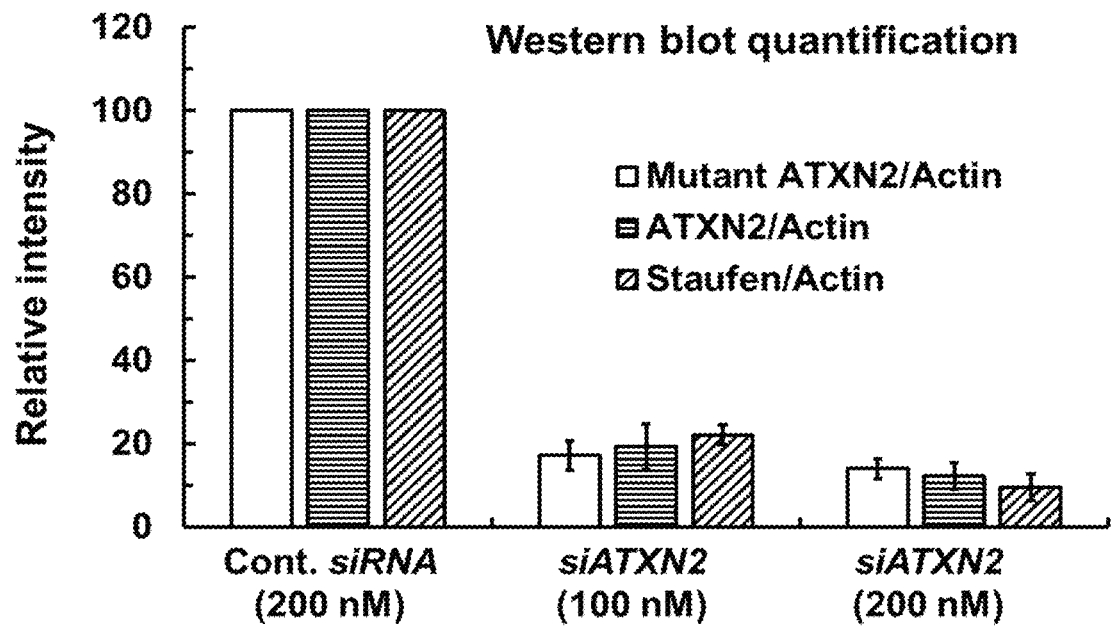
FIG. 7F is a graph of the Quantification of western blots of FIG. 7E determined densitometrically.
Figure 7G:
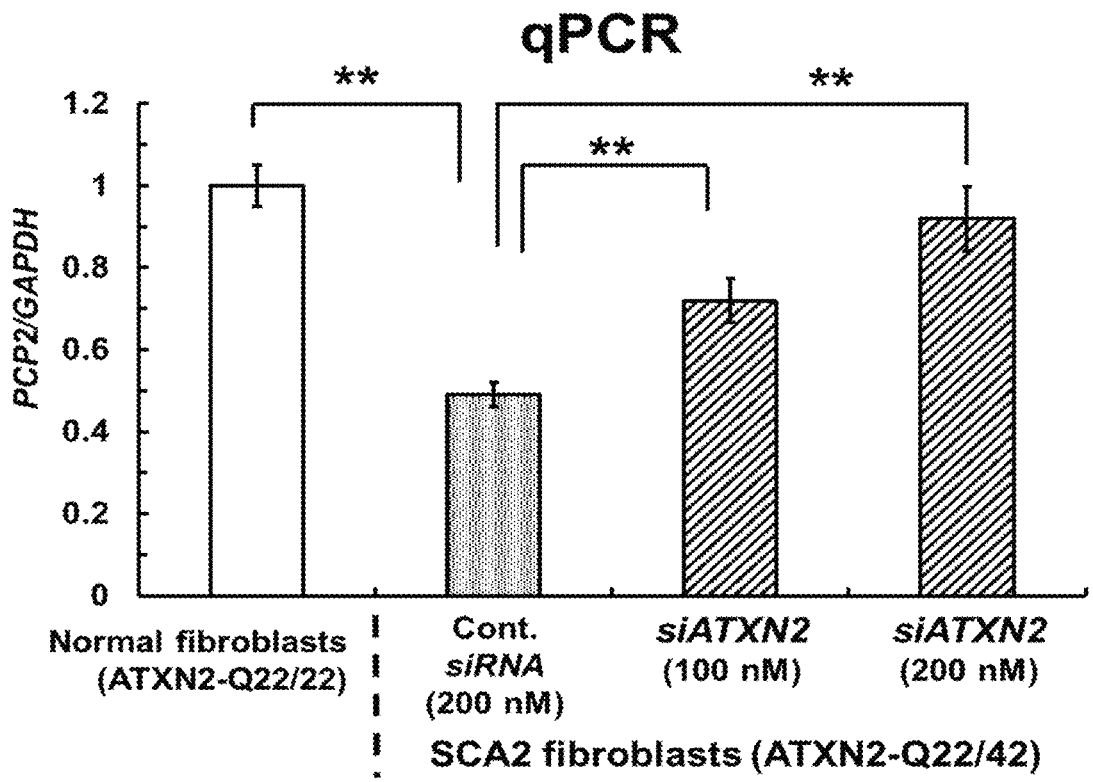
FIG. 7G is a qPCR analysis of synthesized cDNAs from second aliquot show significant incremental of PCP2 transcript levels in SCA2-fibroblasts, upon depletion of ATXN2 dosages, when compared with control siRNA.
Figure 7H:
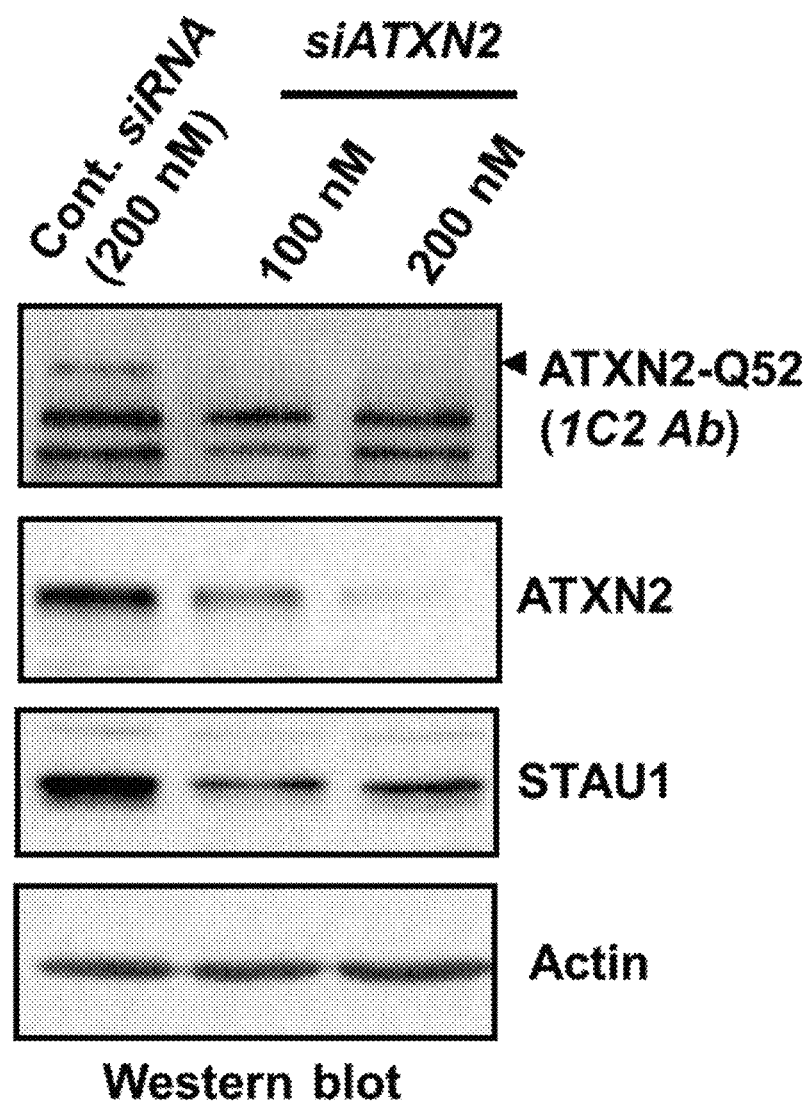
FIG. 7H is a blot of SCA2-LB (ATXN2-Q22/52) cells that were transfected or electroporated with siATXN2 at dose dependent fashion and harvested as two aliquots for protein and RNA analyses after 4 days post-transfection/electroporation. Protein extracts from one aliquot were immunoblotted for ATXN2 and Staufen1 and showing significant reductions of Staufen1 abundance upon depletion of ATXN2 dosages when compared with control siRNA.
Figure 7I:
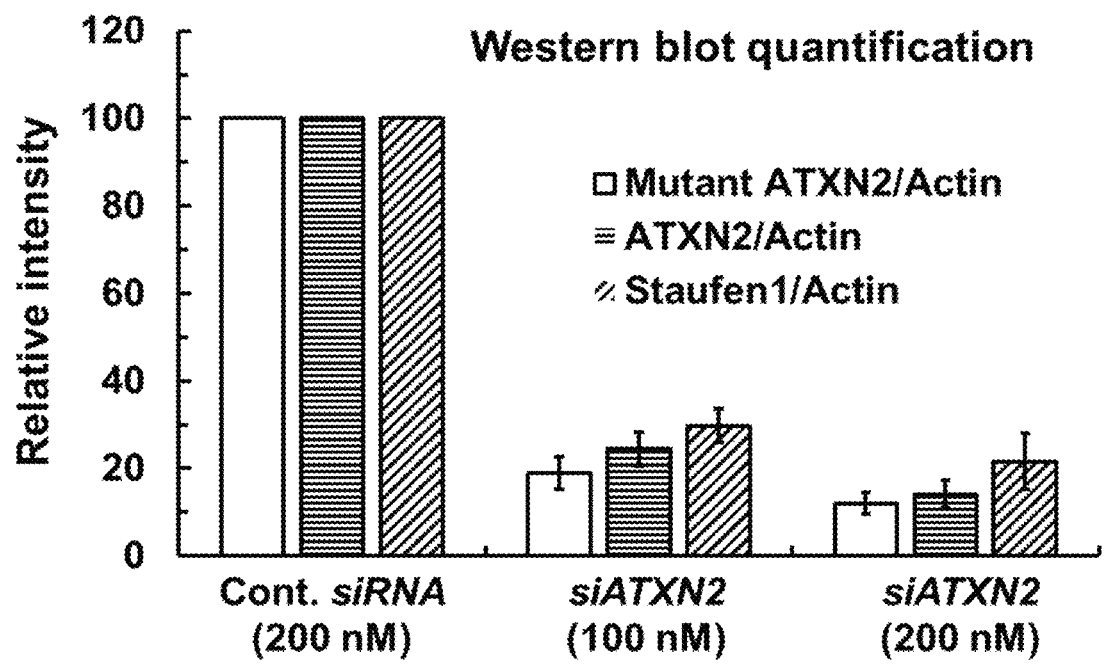
FIG. 7I is a graph of the Quantification of western blots of FIG. 7H determined densitometrically.
Figure 7J:
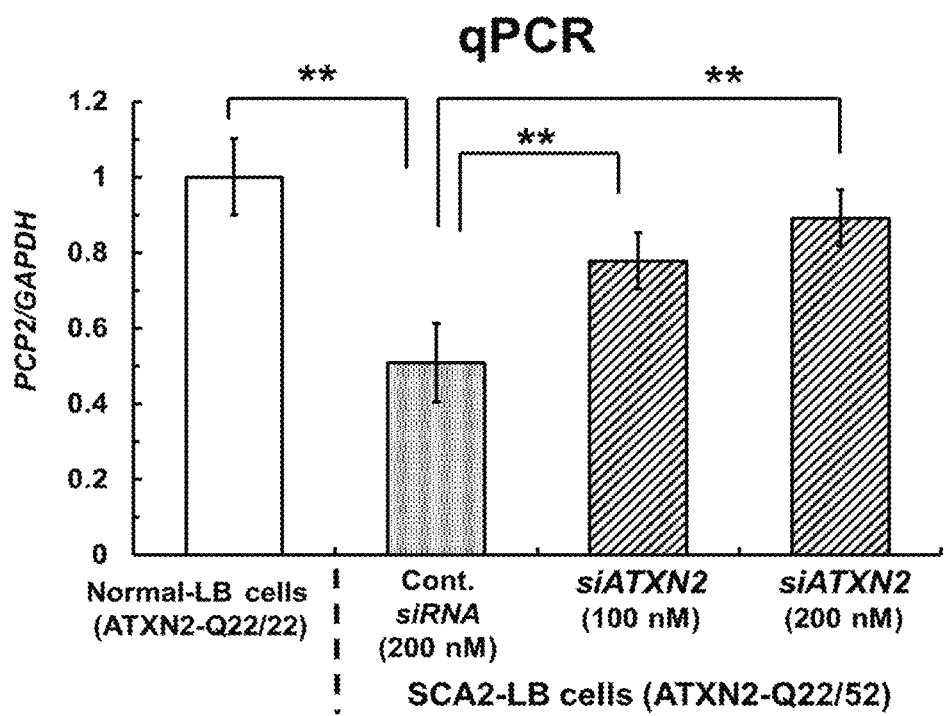
FIG. 7J is a qPCR analysis of synthesized cDNAs from second aliquot show significant incremental of PCP2 transcript levels in SCA2-LB cells, upon depletion of ATXN2 dosages, when compared with control siRNA.

To test this, the consequences of PCP2 mRNA levels in SCA2-LB (ATXN2-Q22/52) cells in which staufen1 levels were reduced by siRNA directed against Staufen1 were studied. qPCR analyses revealed that depletion of Staufen1 (~83%) in SCA2-LB cells restored PCP2 mRNA level to a level similar to that seen in normal LB cells treated with control siRNA (FIGS. 7A-7C). However, silencing of staufen1 (~81%) in normal LB cells did not show significant alteration of PCP2 mRNA levels when compared with normal LB cells treated with control siRNA (FIGS. 7A-7C). Of note, silencing of Staufen1 does not show any effect on ATXN2 transcript levels in normal or SCA2-LB cells (FIG. 7D). Thus, silencing of Staufen1 rescued the effect of the mutant ATXN2 on aberrant RNA metabolism observed in SCA2.

Next, mutant ATXN2 was depleted using siATXN2 RNA in a dose dependent fashion in SCA2-fibroblasts (ATXN2-Q22/42) or -LB (ATXN2-Q22/52) cells. Treatment with ATXN2 siRNA resulted in a dose-dependent reduction of mutant ATXN2 in both cell types (FIGS. 7E, 7F, 7H, and 7I). Upon depletion of ATXN2, significant reduction of Staufen1 abundance and a significant increase of PCP2 mRNA levels were observed in SCA2-LB cells and -fibroblasts when compared with control siRNA (FIGS. 7E-7J). Thus, graded loss of ATXN2 lowered increased staufen1 abundance and resulted in restoration PCP2 mRNA levels in SCA2 cells.

Example 8—ASO Targeting Staufen1 Lowers Staufen1 Levels

The ATXN2 CAG22 repeat was edited to CAG58 repeats in the ATXN2 locus in SH-SY5Y cells using the CRISPR/Cas9/HDR (homology-directed-repair) technique. The human ATXN2 locus was engineered to replace CAG22 with CAG58 repeats in one ATXN2 allele. Modified CAG58 repeats flanking with locus-specific 0.6 Kb left and right homologous arms (HAs) were cloned into donor vector. The single guide RNA (sgRNA) that targeted ATXN2 was cloned into the hSpCas9-2A-Puro (PX459) vector (Addgene #62988). SH-SY5Y cells were transfected with 1.0 µg of linearized donor vector and 1.0 µg of sgRNA and the pgRNA-Cas9 vector using the Lipofectamine 2000 transfection reagent (ThermoFisher scientific). The cells were cultured with 1.0 µg/ml puromycin for 7-10 days. The puromycin-resistant cells were plated and cultured in a 96-well plate at 1 cell/well until wells were ~80% confluent with cells. The cells were then expanded and maintained for PCR screening to identify knock-in positive cells.

SH-SY5Y cells were cultured in standard DMEM with 10% FBS and 1× penicillin/streptomycin in 5% CO2. Transfection of STAU1 siRNA or STAU1 ASO was accomplished using Lipofectamine transfection reagent using standard conditions. Cells were harvested 3-5 days post transfection.

Protein extracts were prepared by suspending cell pellets in SDS-PAGE sample buffer (Laemmli sample buffer) followed by boiling for 5 min. Equal amount of the extracts were subjected to Western blot analysis to determine the steady-state levels of proteins using the indicated antibodies. Protein extracts were resolved by SDS-PAGE and transferred to Hybond P membranes (Amersham Bioscience Inc., USA). After blocking with 5% skim milk in 0.1% Tween 20/PBS, the membranes were incubated with primary antibodies in 5% skim milk in 0.1% Tween 20/PBS for 2 hrs at room temperature or overnight at 4° C. After several washes with 0.1% Tween 20/PBS, the membranes were incubated with the corresponding secondary antibodies conjugated with HRP in 5% skim milk in 0.1% Tween 20/PBS for 2 hrs at room temperature. Following three additional washes with 0.1% Tween 20/PBS, signals were detected by using the Immobilon Western Chemiluminescent HRP Substrate (Millipore Inc., USA; cat #WBKLSO100) according to the manufacturer's protocol. The antibodies used included ATXN2 mAb [(1:3000), BD Biosciences Inc.; cat #611378], rabbit anti-Staufen antibody (Novus biologicals Inc., NBP1-33202), SQSTM1/p62 antibody (Cell signaling, #5114), LC3B Antibody (Novus biologicals Inc., NB100-2220), mTOR antibody (Cell signaling, #2972), Phospho-mTOR (Ser2448) antibody (Cell signaling #2971), β-Actin mAb conjugated with HRP [(1:10,000), Sigma Inc.; cat #A3858]. Secondary antibodies were horse anti-mouse IgG-HRP antibody (Vector laboratories, PI-2000), and goat anti-rabbit IgG-HRP antibody (Vector laboratories, PI-1000).

Figure 8A:
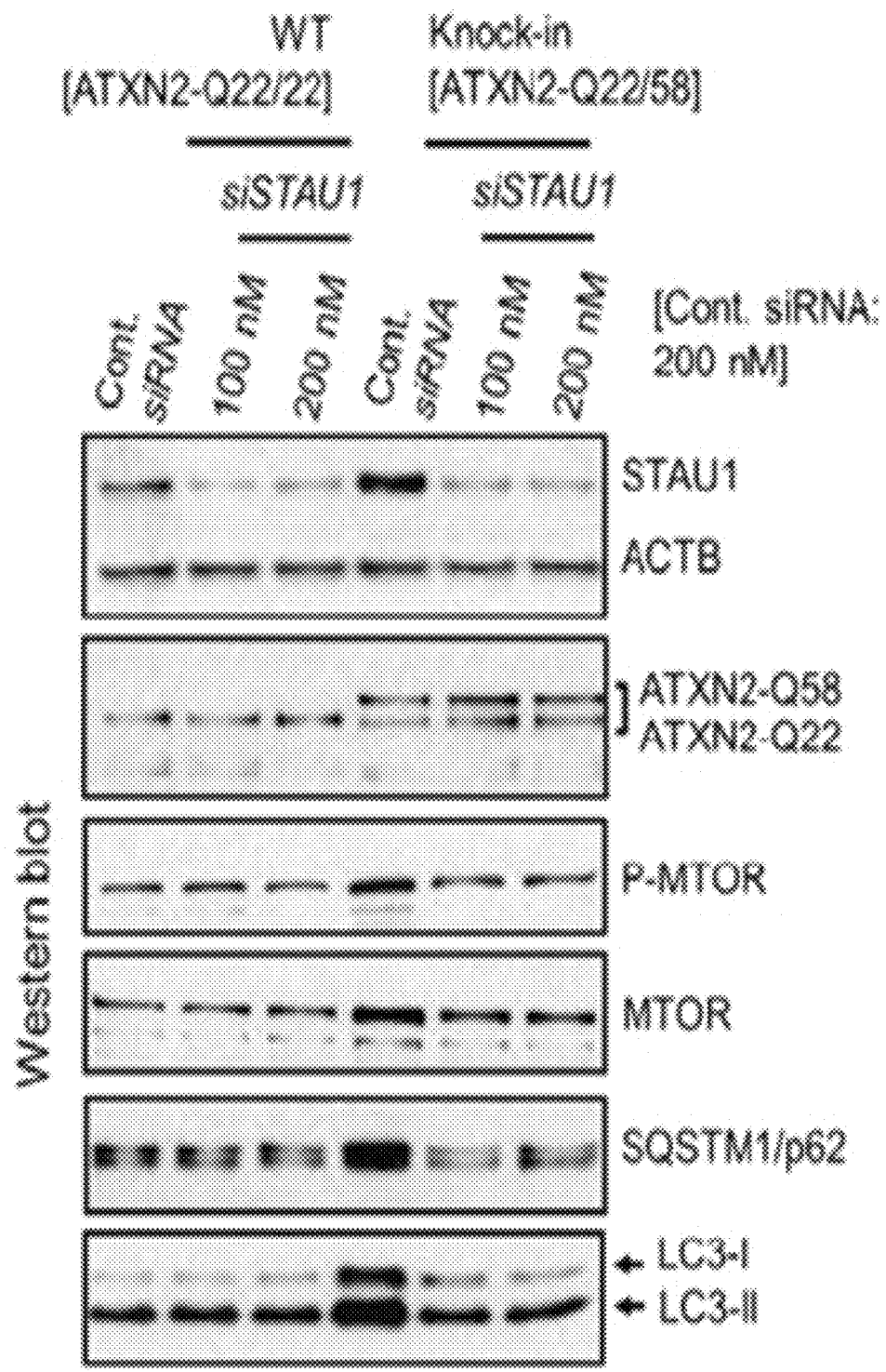
FIG. 8A is a blot showing Staufen1 depletion restored autophagic pathway proteins in ATXN2-Q22/58 knock-in cells. Cells were transfected with STAU1 RNAi and analyzed by western blotting. Autophagy proteins evaluated included the following: total (MTOR) and activated (pMTOR) mechanistic target of rapamycin which is an inhibitor of autophagy, SQSTM1/p62, or sequestosome-1, which binds proteins targeted to the autophagosome. LC3, a commonly used marker of autophagy function. LC3-I is cytoplasmic while a cleaved form with higher mobility. LC3-II, localizes to the autophagosome. The amount of LC3-II is an indicator of autophagosome quantity which typically increases when autophagy is defective.

As illustrated in FIG. 8A, Staufen1 depletion restored autophagic pathway proteins in ATXN2-Q22/58 knock-in cells. Cells were transfected with STAU1 RNAi and analyzed by western blotting. Autophagy proteins evaluated included the following: total (MTOR) and activated (pM-TOR) mechanistic target of rapamycin which is an inhibitor of autophagy, SQSTM1/p62, or sequestosome-1, which binds proteins targeted to the autophagosome. LC3, a commonly used marker of autophagy function. LC3-I is cytoplasmic while a cleaved form with higher mobility. LC3-II, localizes to the autophagosome. The amount of LC3-II is an indicator of autophagosome quantity which typically increases when autophagy is defective.

Figure 8B:
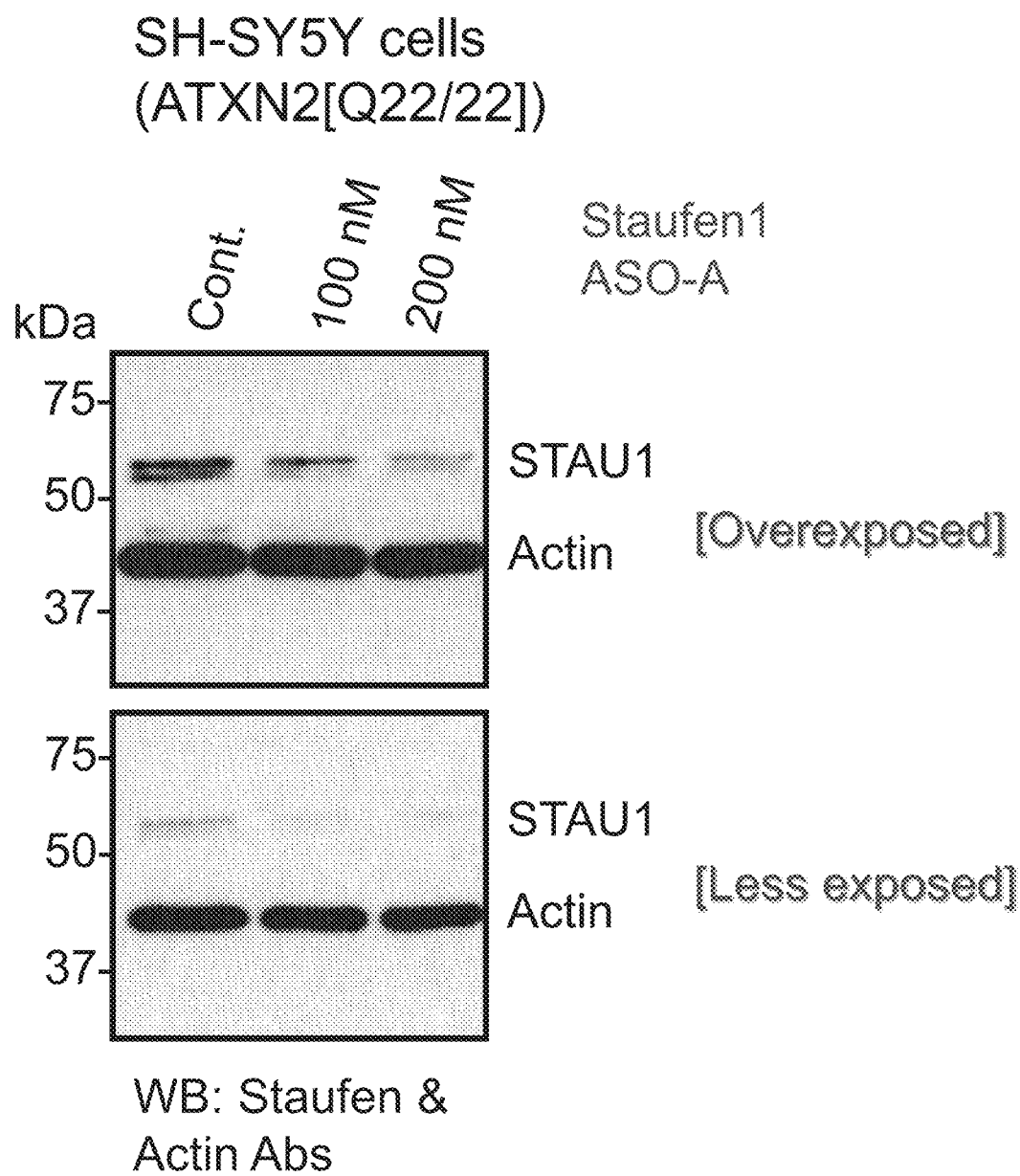
FIG. 8B is a blot showing antisense oligonucleotides (ASOs) targeting Staufen1 lower its expression in SH-SY5Y-ATXN2[Q22/Q22] cells. STAU1 ASO-A (5'-TCTCATGTTGTAGTTATAGG-3' used at the indicated dose reduced STAU1 levels, determined by western blotting. Expression relative to actin.
Figure 8C:
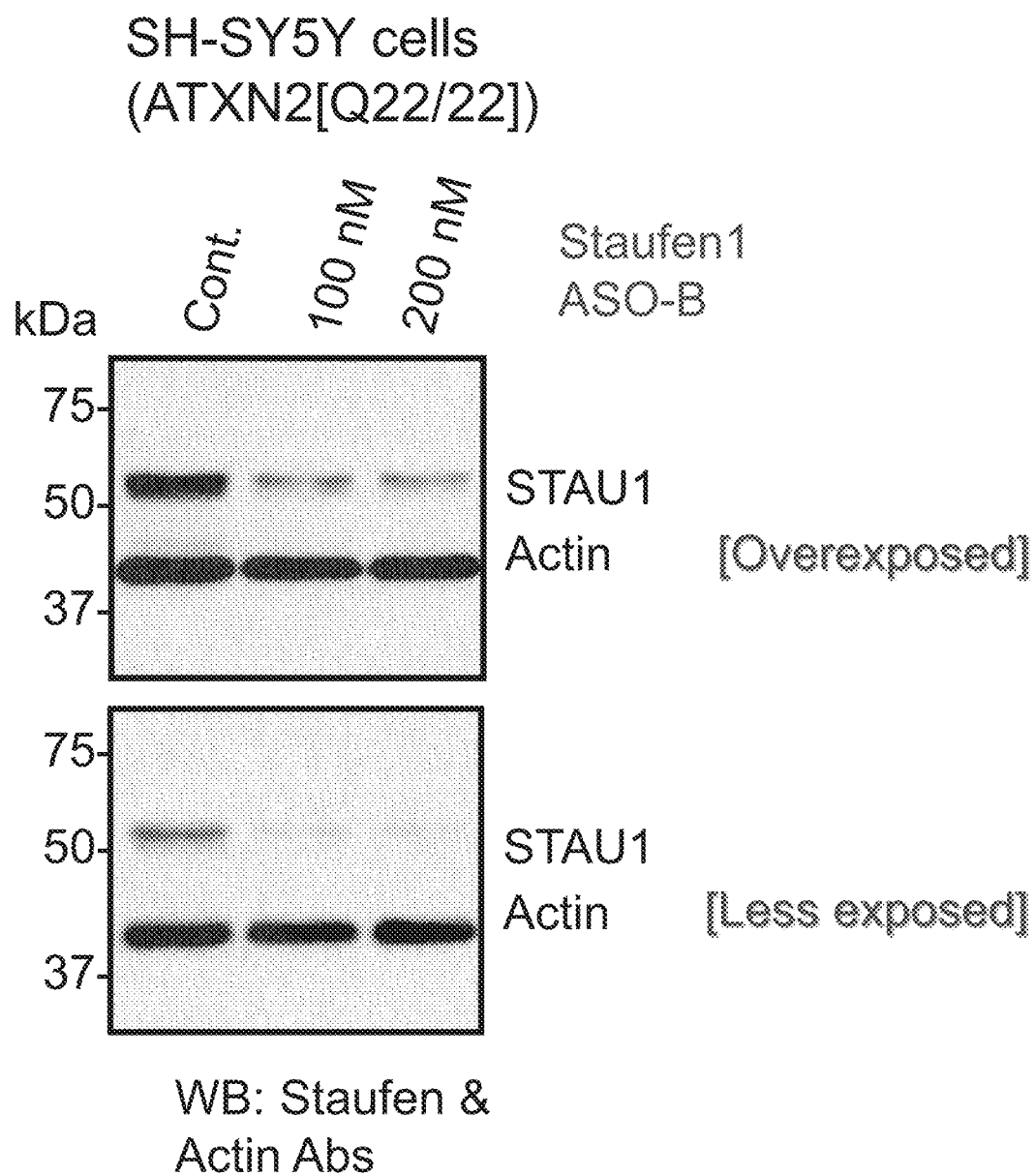
FIG. 8C is a blot showing antisense oligonucleotides (ASOs) targeting Staufen1 lower its expression in SH-SY5Y-ATXN2[Q22/Q22] cells. STAU1 ASO-B (5'-CTGGAAAGATAGTCCAGTTG-3') used at the indicated dose reduced STAU1 levels, determined by western blotting. Expression relative to actin.
Figure 9A:
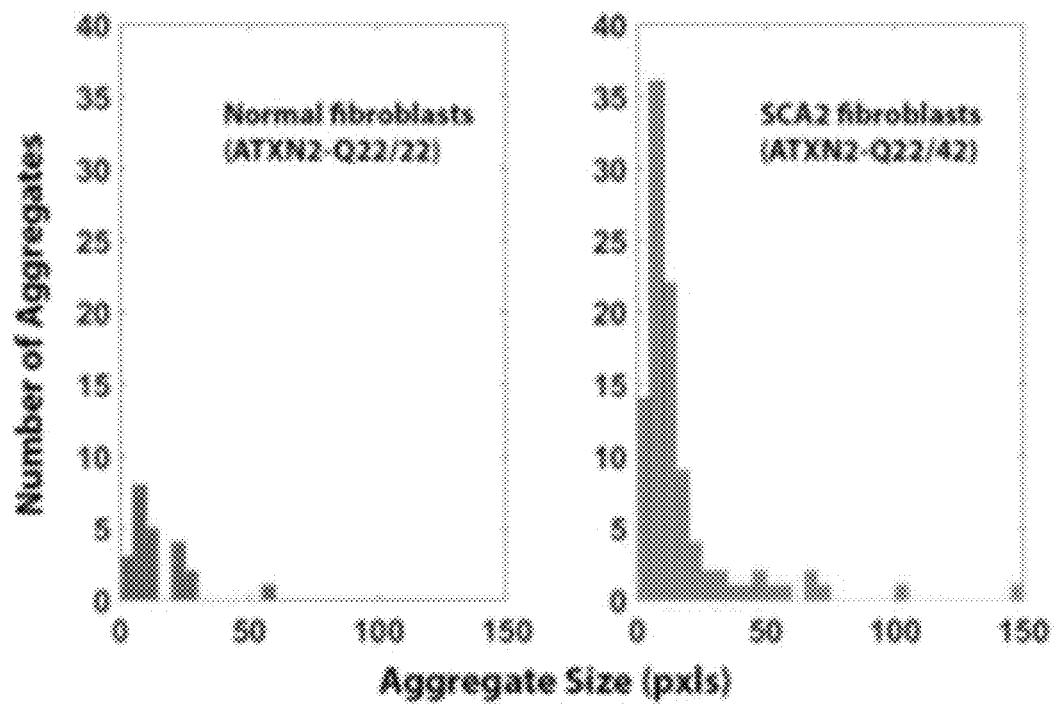
FIG. 9A is a histogram representing quantities and sizes of co-localized granules.
Figure 9B:
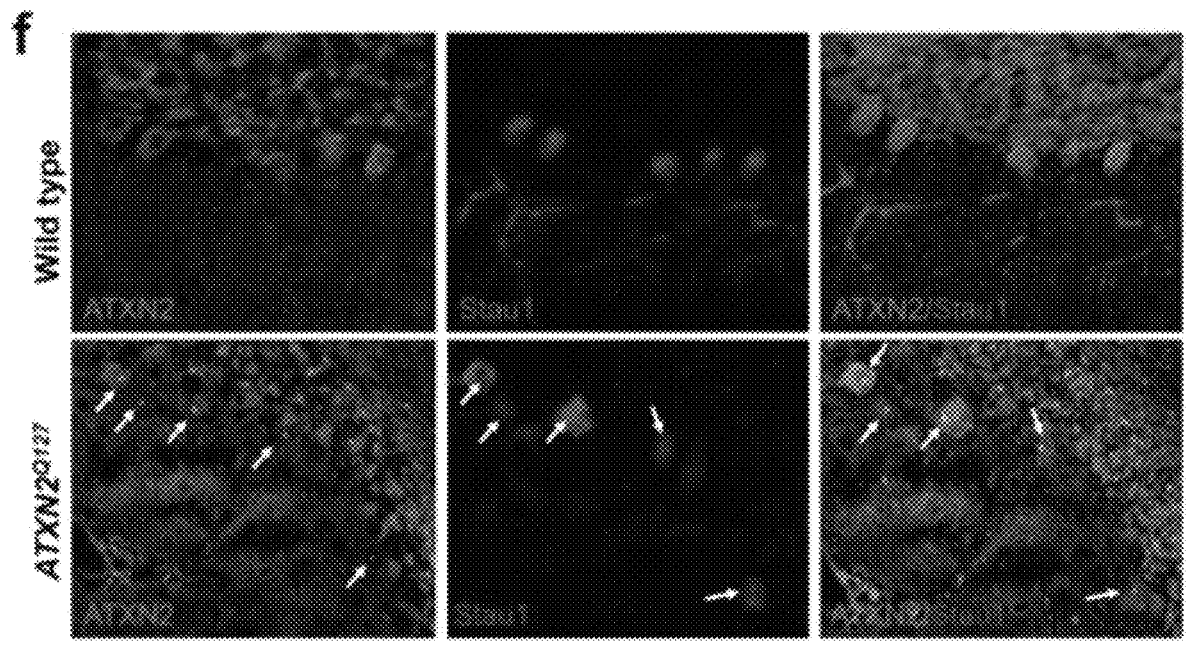
FIG. 9B presents images of co-localization of Staufen1 with mutant ATXN2 detected in ATUN2$^{Q127}$ mouse cerebellar PCs (24 wks of age). Combined double-staining of Staufen1 (red) and ATXN2 (green) shows the presence of aggregates (white arrows) in ATXN2Q$^{127}$ mice.

Further, as illustrated in FIGS. 8B and 8C, Antisense oligonucleotides (ASOs) targeting Staufen1 lower its expression in SH-SY5Y-ATXN2[Q22/Q22] cells. STAU1 ASO-A (5'-TCTCATGTTGTAGTTATAGG-3' (8B) or STAU1 ASO-B (5'-CTGGAAAGATAGTCCAGTTG-3') (8C) used at the indicated dose reduced STAU1 levels, determined by western blotting. Expression relative to actin.

Example 9—Staufen1 Links RNA Stress Granules and Autophagy in Neurodegeneration

DNA constructs. Human cDNA sequences for STAU1 (NM_001037328) were derived from the NCBI DNA database and used to design primers to PCR-amplify the coding sequences from a cDNA library made from SH-SY5Y cells. All cDNAs including ATXN2 with expanded CAG repeats were subsequently cloned into the appropriate vectors; pcDNA3.1/Flag (Agilent Technologies, USA) plasmids. For in vitro RNA binding assay, human Staufen1 and GFP coding sequences were PCR amplified and cloned into pET-His plasmids. All constructs were verified by sequencing.

siRNAs. The siRNAs used in this study were: All Star Negative Control siRNA (Qiagen Inc., USA; Cat #1027280), human siATXN2 [Hs_ATXN2_2 (Qiagen Inc., USA; Cat #SI00308196)], human siST7AUI: 5'-CC-UAUAACUACAACAUGAGdTdT-3', and simTOR: 5'-GAGCCUUGUUGAUCCUUAA-3'. Staufen1 and mTOR siRNA oligonucleotides were synthesized by Invitrogen Inc., USA. The oligonucleotides were deprotected and the complementary strands were annealed.

Cell culture and Transfections. Four normal skin fibroblasts (ATXN2 with CAG22) and five SCA2 patient-derived skin FBs (ATXN2 with CAG repeats; 35, 35, 35, 42, and 45), were maintained in DMEM medium containing 10% fetal bovine serum. Two normal (ATXN2 with CAG22) and three SCA2 patient-derived (ATXN2 with expanded CAG repeats; 40, 46 and 52) Epstein-Barr virus (EBV)-immortalized LBCs were maintained in RPMI medium containing 15% fetal bovine serum. All subjects gave written consent and all procedures were approved by the Institutional Review Board at the University of Utah. The following primary human fibroblasts were obtained from the Coriell Cell Repositories (Camden, N.J., USA): ALS patient (TDP-43$^{G298S}$ mutation) (ND32947), Huntington disease (HD) patient (ND33392) and SCA3 (Machado-Joseph disease, MJD) patient (GM06153). TDP-43$^{G298S}$, HD, SCA3, and SH-SY5Y cells were maintained in DMEM medium containing 10% fetal bovine serum.

For over-expression of recombinant proteins, SH-SY5Y cells were seeded on 100 mm or 6 well dishes and incubated overnight. The cells were then transfected with plasmid DNAs and harvested 48 hrs post-transfection and processed as two aliquots for protein and RNA analyses. For siRNA experiments, cells were transfected with siRNAs using lipofectamine 2000, and lymphoblastoid B cells (1×10$^6$) were electroporated with siRNAs using the Neon transfection system (Invitrogen Inc., USA) according to the manufacturer's protocol and seeded on 6 well plates. Prior standardization experiments showed that maximum silencing was achieved 4-5 days post-transfection/electroporation.

Generation of SH-SY5Y-ATXN2-Q22/58 Knock-in (KI) cells. CRISPR/Cas9-mediated gene editing was carried out according to published protocols. The human ATXN2 locus was engineered to replace CAG22 with CAG58 repeats in ATXN2 exon-1 in a BAC clone (RP11-798L5) containing ATXN2 (Empire Genomics, USA). The modified CAG58 repeat with flanking locus-specific 0.6 Kb left and right homologous arms (HAs) were cloned into a donor vector. The sgRNA oligonucleotides targeting the ATXN2 locus were annealed and cloned into the hSpCas9-2A-Puro (PX459) vector (Addgene #62988). SH-SY5Y cells were transfected with linearized donor vector and single guide RNA pgRNA-Cas9 vector using lipofectamine 2000 transfection reagent (ThermoFisher scientific). The cells were cultured with 1.0 μg/ml puromycin for ~7-10 days. The puromycin-resistant cells were plated and cultured in a 96-well plate at 1 cell/well until most wells were ~80% confluent with cells. The cells were then expanded and maintained for PCR screening to identify knock-in positive cells.

Mice. ATXN2$^{Q127}$ (Pcp2-ATXN2[Q127]) mice in a B6; D2 background, and BAC-SCA2 mice (BAC-Q22 and BAC-Q72) in an FVB background were used. The Staul$^{tm1APa(-/-)}$ (Staul$^{-/-}$) mouse was a generous gift from Prof Michael A. Kiebler, Ludwig Maximilian University of Munich, Germany, and maintained in a B6 background. The TDP-43 transgene [B6; SJL-Tg(Thy1-TARDBP)4Singh/J] ALS mouse was purchased from the Jackson laboratory (Stock no. 012836) and maintained in a B6 background. Genotyping of animals was according to published protocols. All mice were bred and maintained under standard conditions consistent with National Institutes of Health guidelines and conformed to an approved University of Utah IACUC protocol.

Antibodies. The antibodies used for western blotting and immunohistochemistry and their dilutions were as follows: mouse anti-Ataxin-2 antibody (Clone 22/Ataxin-2) (BD Biosciences Inc., 611378), rabbit anti-neomycin phosphotransferase II (NPTII) antibody (EMD Millipore, AC 113), rabbit anti-Staufen antibody (Novus biologicals Inc., NBP1-33202), rabbit anti-DDX6 antibody (Novus biologicals Inc., NB200-191), RGS8 antibody (1:5000) (Novus Biologicals, NBP2-20153), LC3B Antibody (Novus biologicals Inc., NB100-2220), monoclonal anti-FLAG M2 antibody (Sigma Inc., F3165), Monoclonal Anti-Calbindin-D-28K antibody [(1:5000), Sigma Inc., C9848], monoclonal anti-β-Actin-peroxidase antibody (clone AC-15) (Sigma Inc., A3854), goat anti-TIA-1 antibody (C-20) (Santa Cruz Inc., sc-1751), PCP-2 antibody (F-3) [(1:3000), Santa Cruz Inc., sc-137064], Homer-3 Antibody (E-6) [(1:2000), Santa Cruz Inc., sc-376155], Anti-PCP4 antibody [(1:5000) Abcam Inc., ab197377], Anti-FAM107B antibody (1:5,000) (Abcam Inc., ab175148), rabbit anti-PABP antibody (Abcam Inc., ab153930), p21 Wafl/Cip1 (12D1) rabbit mAb (Cell signaling, 2947), mTOR antibody (Cell signaling, #2972), Phospho-mTOR (Ser2448) antibody (Cell signaling #2971), SQSTM1/p62 antibody (Cell signaling, #5114), anti-c-Myc epitope tag monoclonal antibody, HRP conjugate (Thermo Fisher Scientific, R951-21), 6×-His epitope tag monoclonal antibody, HRP conjugate (HIS.H8) (Invitrogen Inc., MA1-21315-HRP) and sheep-anti-Digoxigenin-POD, Fab fragments (Roche Life Science, 11207733910). The secondary antibodies were: horse anti-mouse IgG-HRP antibody (Vector laboratories, PI-2000), goat anti-rabbit IgG-HRP antibody (Vector laboratories, PI-1000) and horse anti-goat IgG-HRP antibody (Vector laboratories, PI-9500). Fluorescent secondary antibodies were: goat anti-mouse IgG (H+L) antibody, DyLight-488 (Invitrogen Inc., 35502), goat anti-mouse IgG (H+L) antibody, DyLight-550 (Invitrogen Inc., 84540), goat anti-rabbit IgG (H&L) antibody (Thermo Scientific, 35557), goat anti-rabbit IgG (H+L) antibody, DyLight-488 (Invitrogen Inc., 35552), and donkey anti-goat IgG (H+L) antibody, DyLight-550 (Invitrogen Inc., SA5-10087).

Immunofluorescence. Immunofluorescence studies were performed to determine the co-localization of ATXN2 and Staufen1. Briefly, SCA2 fibroblasts and SH-SY5Y-ATXN2-Q22/58 KI cells were plated on cover slides overnight and fixed with 4% paraformaldehyde/PBS. To determine localization of ATXN2 with Staufen1 in stress granules, SH-SY5Y cells were cultured on cover slides for overnight and heat-shocked at 43.5° C. for 1 hr. Cells were fixed with 4% paraformaldehyde/PBS, permeabilized with 0.1% Triton X-100, and processed for immunostaining using corresponding primary and fluorescent secondary antibodies. The nuclei were stained with DAPI followed by mounting with Fluoromount-G (Southern Biotech Inc.; 0100-01). The cells were imaged using confocal microscope (Nikon Eclipse Ti microscopy) and analyzed using the Nikon EZ-C1 software. The co-localization plugin in ImageJ was used to define co-localized areas via intensity-based thresholding. The Analyze Particles tool was then used to count the number of co-localized areas greater than four pixels (baseline). Isolated cerebella were fixed in 4% paraformaldehyde and embedded in paraffin. Sections were deparaffinized using standard conditions, blocked with 5% donkey serum 0.3% Triton X-100 in PBS and processed for immunostaining. Primary antibodies: custom-designed ATXN2 rabbit polyclonal antibody [SCA2-280 (1:250)], STAU1 antibody (C-4) [(1:250), Santa Cruz Inc., sc-390820], and corresponding fluorescent secondary antibodies were used. Images were acquired using confocal microscope (Nikon Eclipse Ti microscopy) and analyzed by the Nikon EZ-C1 software.

Preparation of protein lysates and western blot analyses. Cellular extracts were prepared by a single-step lysis method. The harvested cells were suspended in SDS-PAGE sample buffer [Laemmli sample buffer (Bio-Rad Inc.; cat #161-0737)] and then boiled for 5 min. Equal amounts of the extracts were used for western blot analyses. Cerebellar protein extracts were prepared by homogenization of mouse cerebella in extraction buffer [25 mM Tris-HCl pH 7.6, 300 mM NaCl, 0.5% Nonidet P-40, 2 mM EDTA, 2 mM $MgCl_2$, 0.5 M urea and protease inhibitors (Sigma Inc.; cat #P-8340)] followed by centrifugation at 4° C. for 20 min at 14,000 RPM. Only supernatants were used for western blotting. Protein extracts were resolved by SDS-PAGE and transferred to Hybond P membranes (Amersham Bioscience Inc., USA). After blocking with 5% skim milk in 0.1% Tween 20/PBS, the membranes were processed for immunostaining using corresponding primary and secondary antibodies. Signals were detected by using the Immobilon Western Chemiluminescent HRP Substrate (Millipore Inc., USA; cat #WBKLSO100) according to the manufacturer's protocol. The intensity of proteins was determined by using the ImageJ software analyses system and the relative protein abundances were expressed as ratios to β-actin.

Immunoprecipitations. To determine protein-protein or protein-RNA interactions, we carried out protein-RNA immunoprecipitation (IP) experiments using SH-SY5Y cells expressing Flag-ATXN2-Q22 and Flag-ATXN2-Q108 or Flag-Staufen1. The preparation of whole cell extracts and IP methods followed previously published methods. First, cells were lysed with a cytoplasmic extraction buffer [25 mM Tris-HCl pH 7.6, 10 mM NaCl, 0.5% NP40, 2 mMEDTA, 2 mM $MgCl_2$, protease inhibitors (Sigma Inc.; Cat #P-8340)] and cytoplasmic extracts were separated by centrifugation at 14,000 RPM for 20 min. Second, the resultant pellets were suspended in nuclear lysis buffer or high salt lysis buffer (25 mM Tris-HCl, pH 7.6, 500 mM NaCl, 0.5% Nonidet P-40, 2 mM EDTA, 2 mM $MgCl_2$, protease inhibitors), and the nuclear extracts were separated by centrifugation at 14,000 RPM for 20 min. The nuclear extracts were then combined with the cytoplasmic extracts and denoted whole cell extracts. Specifically, while combining cytoplasmic and nuclear extracts, the NaCl concentration was adjusted to physiologic buffer conditions (~150 mM) to preserve in vivo interactions. For identifying non-RNA mediated interactions, whole cell extracts were treated with 1.0 mg/ml RNase A (Amersham Bioscience Inc., USA) for 15 min at 37° C. before subjected to IP. Ninety percent of cell extracts were subjected to Flag monoclonal antibody (mAb) IP (Anti-FlagM2 Affinity Gel, Sigma Inc.; cat #A2220-1ML) to immunoprecipitate ATXN2 or Staufen1 interacting protein-RNA complexes. The remaining 10% of whole cell extracts were saved as the input control for western blotting and RT-PCR analyses. The IPs were washed with a buffer containing 200 mM NaCl and the bound protein-protein or protein-RNA complexes were eluted from the beads with Flag peptide competition (100 μg/ml). Eluted fractions were divided into two equal parts. One part was analyzed by SDS-PAGE followed by western blotting to determine interactions between ATXN2 and Staufen1. RNA was isolated from the other fraction and subjected to RT-PCR analyses to identify RNAs that bound to Staufen1.

In vitro RNA binding (Northwestern) assay. Northwestern blot assays were performed following a published protocol with some modifications. BL21<DE3> cells carrying His-Staufen1, His-GFP and empty pET vectors, were grown to mid-log phase. Whole cell lysates from harvested cells were run on SDS-PAGE and electro-blotted onto a Hybond P membrane. The transferred proteins were re-natured as follows: the blot was first incubated with binding buffer (0.1 M HEPES, pH 7.9, 0.1 M $MgCl_2$, 0.1 M KCl, 0.5 μM $ZnSO_4$) with 1 mM DTT and 6 M urea for 5 min at room temperature. The blots were then incubated, for 5 min each, through five serial twofold dilutions of urea with binding buffer/1 mM DTT with continuing incubation steps until the binding buffer was 1 mM DTT without urea. Blot pre-hybridizations were carried out with binding buffer (1 mM DTT, 5% BSA, 1 μg/ml yeast tRNA) for 1 hr at room temperature. The blots were then hybridized with DIG-labelled RNA probes in binding buffer (1 mM DTT, 0.25% BSA, 1 μg/ml yeast tRNA) overnight at 4° C. After several washes with 0.1% Tween 20/PBS, the membranes were incubated with anti-DIG-POD antibody in 5% skim milk in 0.1% Tween 20/PBS for 2 hr at room temperature. Following three additional washes with 0.1% Tween 20/PBS, signals were detected by using the Immobilon Western Chemiluminescent HRP Substrate according to the manufacturer's protocol.

RNA expression analyses by Quantitative RT-PCR. Mice were deeply anesthetized with isoflurane. Mouse cerebella were removed and immediately submerged in liquid nitrogen. Tissues were kept at −80° C. until the time of processing. Total RNA was extracted from mouse cerebella and from harvested cells using the RNaeasy mini-kit according to the manufacturer's protocol (Qiagen Inc., USA). DNAse I treated RNAs were used to synthesize cDNAs using the ProtoScript cDNA synthesis kit (New England Biolabs Inc., USA). Quantitative RT-PCR was performed in QuantStudio 12K (Life Technologies, Inc.; USA) with the Power SYBR Green PCRMaster Mix (Applied Biosystems Inc.; USA). PCR reaction mixtures contained SYBR Green PCRMaster mix, synthesized cDNA and 0.5 pmol primers, and PCR amplifications were carried out for 45 cycles: denaturation at 95° C. for 10 sec, annealing at 60° C. for 10 sec and extension at 72° C. for 40 sec. The threshold cycle for each sample was chosen from the linear range and converted to a starting quantity by interpolation from a standard curve run on the same plate for each set of primers. All gene expression levels were normalized to the ACTB or GAPDH or Actb mRNA levels. Primer pairs designed for qRT-PCR and RT-PCR are given as forward and reverse, respectively, and listed in Table 1 below.

TABLE 1

RT-PCR and qPCR primer sequences.

| | | | |
|---|---|---|---|
| SCA2-A | 5'-GGGCCCCTCACCATGTCG-3' | Human | RT-PCR |
| SCA2-B | 5'-CGGGCTTGCGGACATTGG-3' | " | " |
| ATXN2-Exon1-F | 5'CCGCCCGGCGTGCGAGCCGGTGTATGG-3' | " | " |
| ATXN2-Exon2-R | 5'-GTAGACTGAGGCAGTCCTTTGTTACTG-3' | " | " |
| GAPDH-F | 5'-ACATCGCTCAGACACCATG-3' | " | RT-PCR/qRT-PCR |
| GAPDH-R | 5'-TGTAGTTGAGGTCAATGAAGGG-3' | " | " |
| ACTB-F | 5'-GAAAATCTGGCACCACACCT-3 | " | qRT-PCR |
| ACTB-R | 5'-TAGCACAGCCTGGATAGCAA-3' | " | " |
| STAU1-F | 5'-TCCTTGGTTTCAAAGTCCCG-3 | " | " |
| STAU1-R | 5'-ATTTTCATCCCCAGAGCCAG-3' | " | " |
| PCP2-F | 5'-AAGGACGGAGCACAGAAAC-3' | " | " |
| PCP2-R | 5'-GAGTGAGACCCAGGATGC-3' | " | " |
| ATXN2-F | 5'-AAGATATGGACTCCAGTTATGCAAA-3' | " | " |
| ATXN2-R | 5'-CAAAGCCTCAAGTTCCTCAT-3' | " | " |
| CACNA1G | 5'-CCGACCCACAGATCCCTCTA-3' | " | " |
| CACNA1G | 5'-GCTGTCATTGGGCAGAGAGT-3' | " | " |
| ITPR1 | GCACGTCTTCCTGAGAACCA | " | " |
| ITPRI | CACTGAGGGCTGAAACTCCA | " | " |
| PCP2-F | 5'-GCCAGATCCAGCATCGTTGT-3 | " | RT-PCR |
| PCP2-R | 5'-CTCTGGCTCTTGGTGGTCTG-3' | " | " |
| mTOR-F | 5'-CGAACCTCAGGGCAAGATG-3' | " | " |
| mTOR-R | 5'-TTTCCTCATTCCGGCTCTTTAG-3' | " | " |
| Stau1-F | 5'-AGTACATGCTCCTTACAGAACG-3' | Mouse | qRT-PCR |
| Stau1-R | 5'-TGATGCCCAACCTTTACCTG-3' | " | " |
| Actb-F | 5'-CGTCGACAACGGCTCCGGCATG-3' | " | " |
| Actb-R | 5'-GGGCCTCGTCACCCACATAGGAG-3' | " | " |

Rotarod Testing. Following genotyping mice were randomly assigned to cages according to sex, ensuring that each possible genotype was represented in each cage. During the five days of testing, mice were taken to a separate testing room and allowed to habituate for one hour. Testing began at the same time every day and was completed by the same technician. The technician was blinded to the genotypes of the mice in each cage. On day 1 mice were handled for 2 min per mouse. On day 2 mice were placed on an accelerating rotarod apparatus (Rotamex-5, Columbus Instruments, Columbus, Ohio, USA) initially rotating at 4 RPM for 2 min. The rate of rotation was increased by 1 RPM per every 15 s to 10 RPM for 60 s. On days 3-5, mice were tested on the accelerating rotarod from 0 RPM with acceleration increasing by 1 RPM every 9 s until the maximum speed of 51 RPM was reached (maximum time of 459 s). The time that a mouse fell (latency to fall) from the rotating bar was recorded. Statistical comparisons of rotarod data were determined using the method of generalized estimating equations (GEE) with the independent correlation option using Stata 12 (procedures xtset followed by xtgee).

Statistical analysis. For western blot analyses, the experiments were performed three times, and wherever appropriate, gels were scanned and band intensities quantified by ImageJ analyses after inversion of the images. The P values were calculated by pairwise Student's t-test to determine whether difference between groups were significant. The level of significance was set at $P \leq 0.05$. In the figures, a single asterisk indicates $P<0.05$, a double asterisk $P<0.01$, a triple asterisk $P<0.001$, and ns represents $P>0.05$ (Student's t-test).

Results. Disorders of RNA metabolism have recently come into focus either as directly causative via mutation of the respective proteins or as contributing through formation of RNA stress granules and sequestration of proteins into these granules. Thus, mutations in the RNA binding protein, Tar DNA binding protein-43 (TDP-43) cause ALS and ALS/Frontotemporal lobar degeneration (FTLD), but other genetic or non-genetic forms of ALS also show TDP-43 accumulation in spinal motor and cortical neurons.

Figure 10A:
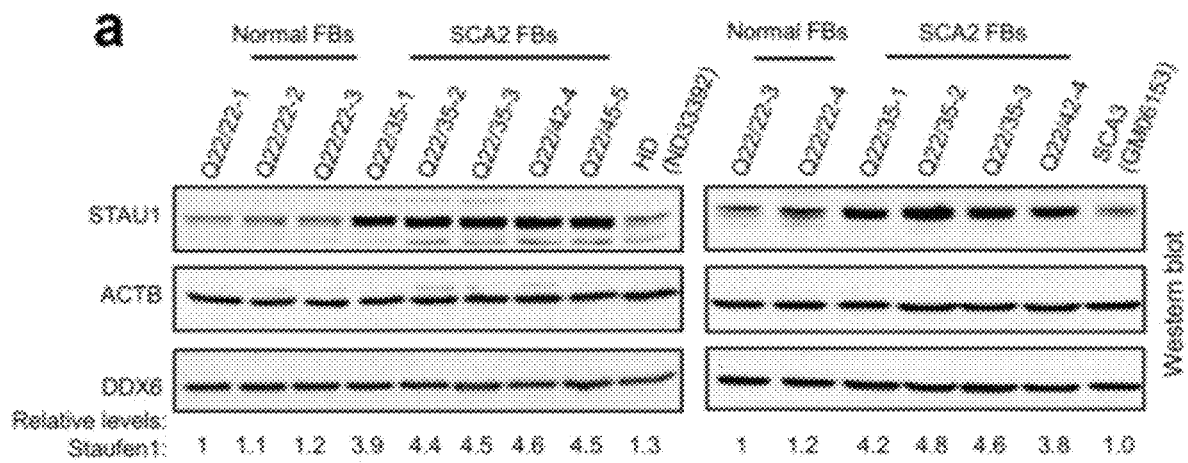
FIG. 10A presents a western blot analysis of SCA2 fibroblasts showing increased Staufen1 levels compared with normal controls. DDX6 levels are unchanged.
Figure 10B:
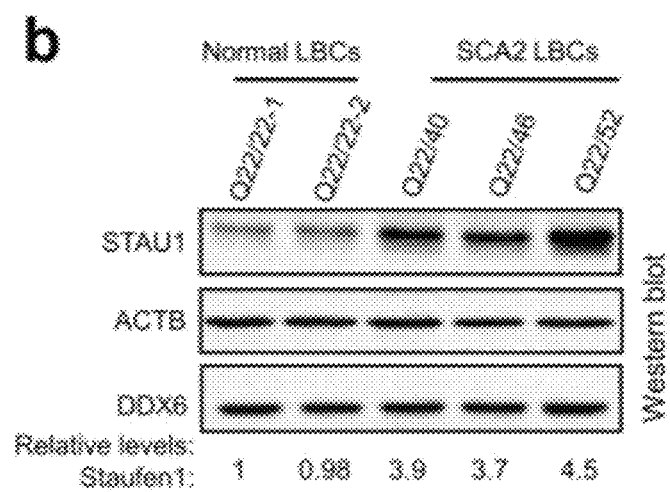
FIG. 10B presents a western blot analysis of LBCs showing increased Staufen1 levels compared with normal controls. DDX6 levels are unchanged.
Figure 10C:
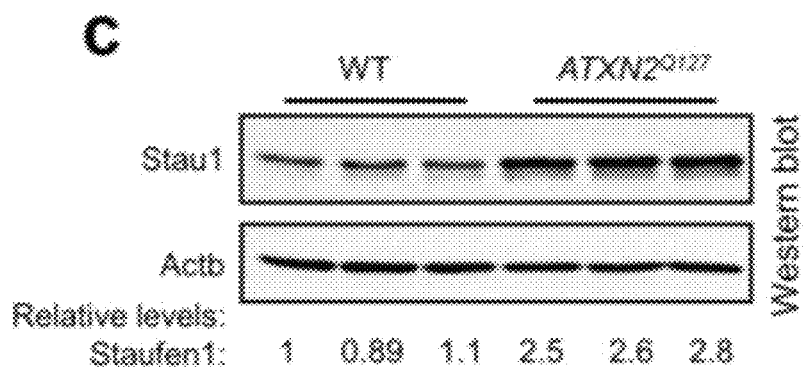
FIG. 10C presents a western blot analysis showing increased Staufen1 levels in cerebellar extracts from ATXN2$^{Q127}$ mice at 24 weeks of age.
Figure 10D:
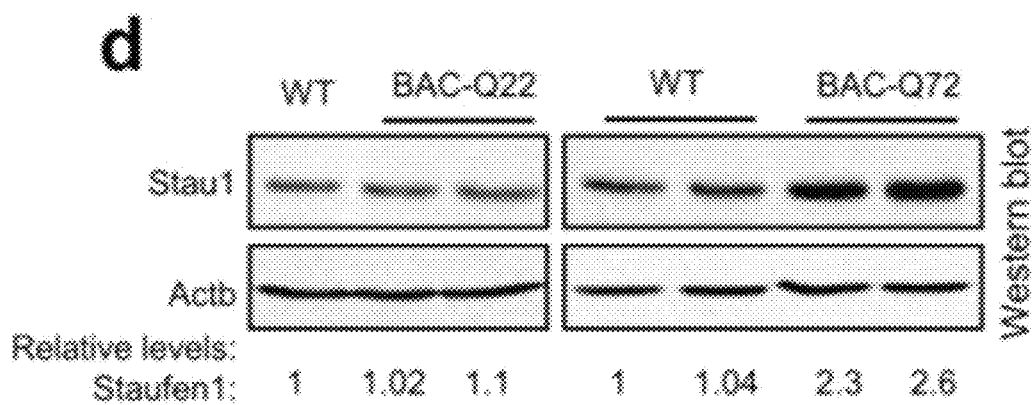
FIG. 10D presents a western blot analysis showing increased Staufen1 levels in cerebellar extracts from BAC-Q72 mice at 24 weeks of age.

To further define components of the dysregulated stress response in SCA2 and TDP43-mediated motor neuron death the ATXN2 protein complex was purified. As described above, a prominent protein in the ATXN2 complex in SH-SY5Y cells is STAU1, showing RNA-dependent interaction with wild-type or mutant ATXN2 by co-immunoprecipitation (FIG. 1F). STAU1 is a well-characterized double-stranded RNA-binding protein and component of RNA stress granules (SGs). As also described above, heat-stressed SH-SY5Y cells produced SGs positive for both ATXN2 and STAU1 (FIG. 1A). In SCA2 patient fibroblasts (FBs), constitutively-present ATXN2/STAU1 SGs were observed even in the absence of stress as well as in Purkinje cells of SCA2 (ATXN2$^{Q127}$) mice (FIGS. 1B-1C and FIGS. 9A-9B). Upon verification of the levels of proteins in SCA2-patient FBs and lymphoblastoid cells (LBCs), it was noted that STAU1 levels were significantly increased in the presence of endogenous mutant ATXN2 (FIGS. 10A-10B). This observation was also confirmed by analysis of cerebellar extracts from two animal models of SCA2 (ATXN2$^{Q127}$ and BAC-Q72) (FIGS. 10C-10D).

Figure 10E:
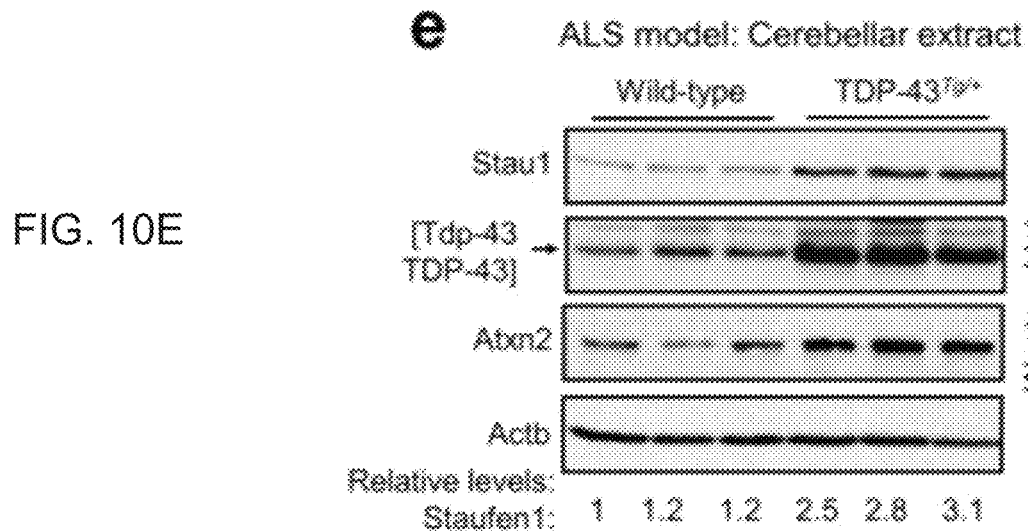
FIG. 10E presents a western blot analysis of cerebellar extracts from TDP-43$^{Tg/+}$ hemizygous mice at 8 weeks of age compared with wild-type litter mates.
Figure 10F:
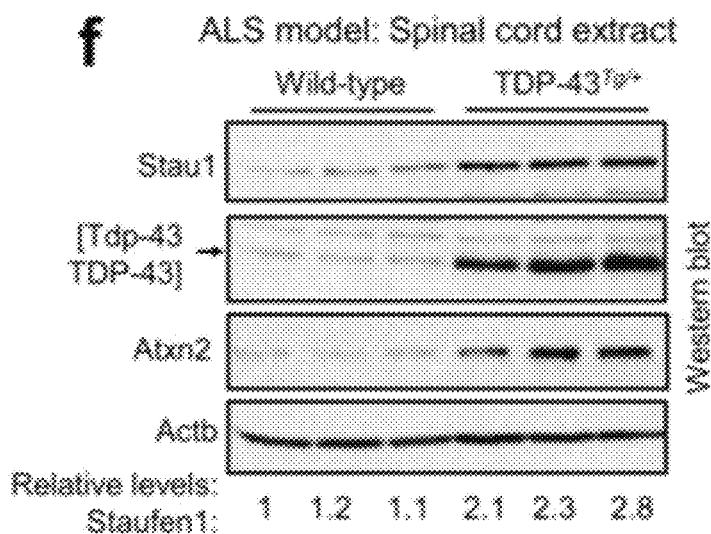
FIG. 10F presents a western blot analysis of spinal cord extracts from TDP-43$^{Tg/+}$ hemizygous mice at 8 weeks of age compared with wild-type litter mates.
Figure 10G:
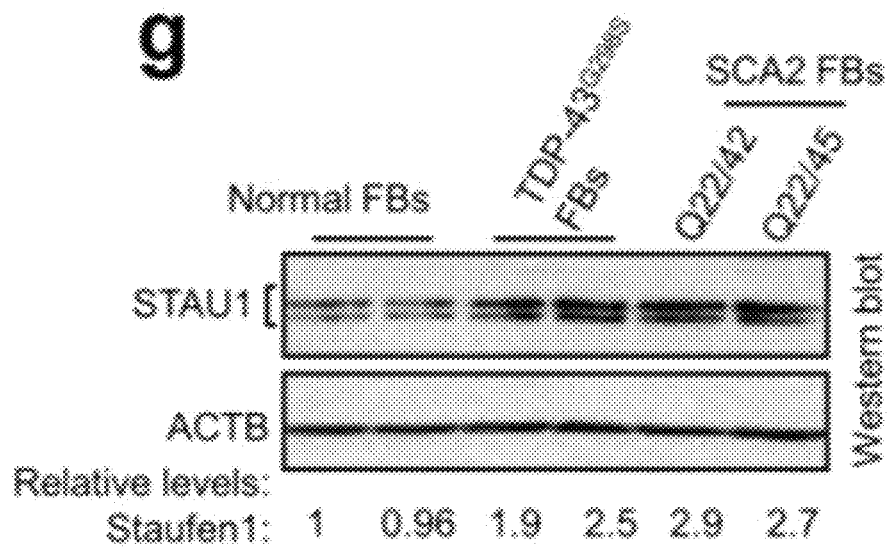
FIG. 10G presents a western blot analysis showing increased Staufen1 in FB extracts from a patient with ALS caused by TDP-43$^{G298S}$ mutation.
Figure 10H:
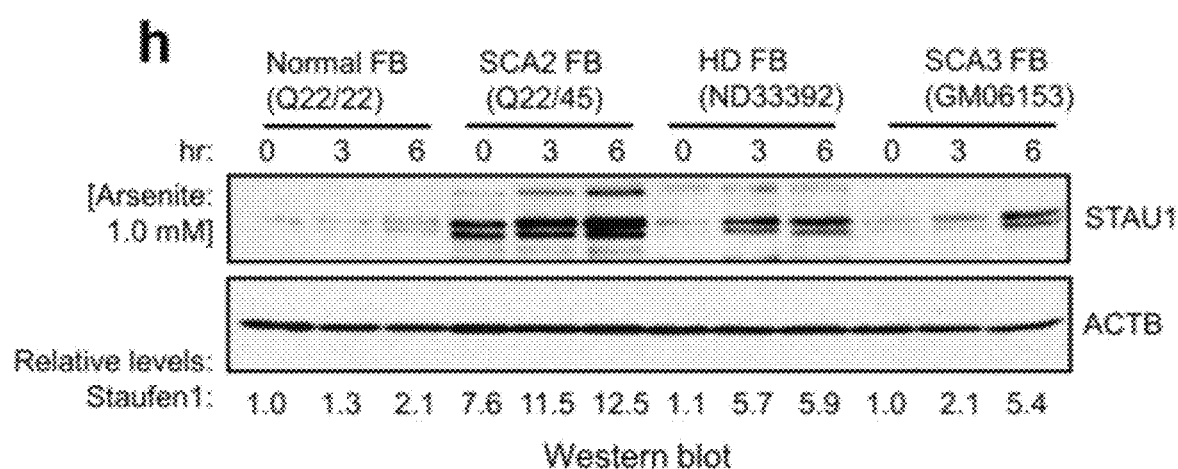
FIG. 10H presents a western blot analysis showing arsenite-induced stress results in exaggerated increases in STAU1 levels in HD and SCA3 FBs. SCA2, HD and SCA3 FBs were treated with sodium arsenite (1.0 mM) for 0, 3 and 6 hr followed by immunoblotting. β-actin was used as loading control and representative blots of three independent experiments are shown.
Figure 11A:
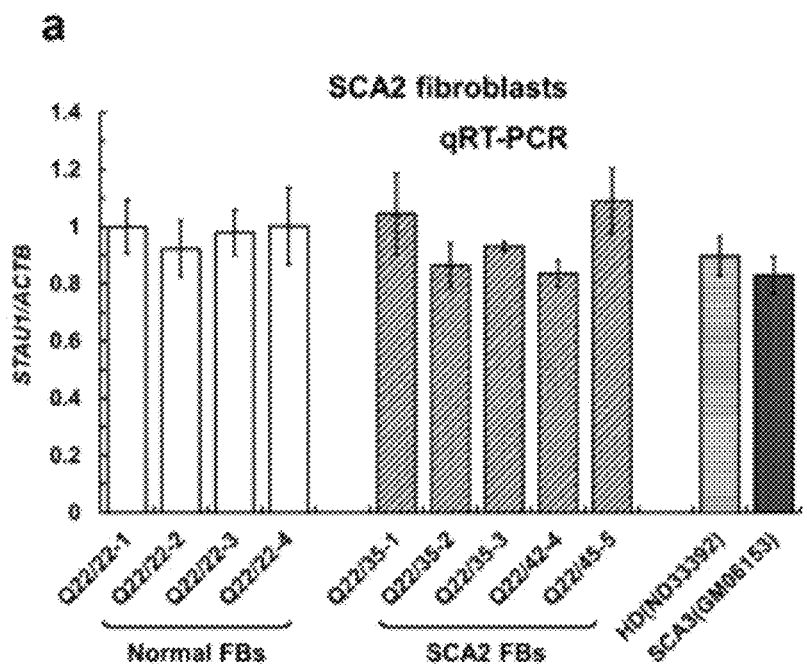
FIG. 11A is a graph showing Staufen1 transcript levels do not correspond to the differences in the steady state Staufen1 protein levels observed in SCA2-FBs when compared to control cells.
Figure 11B:
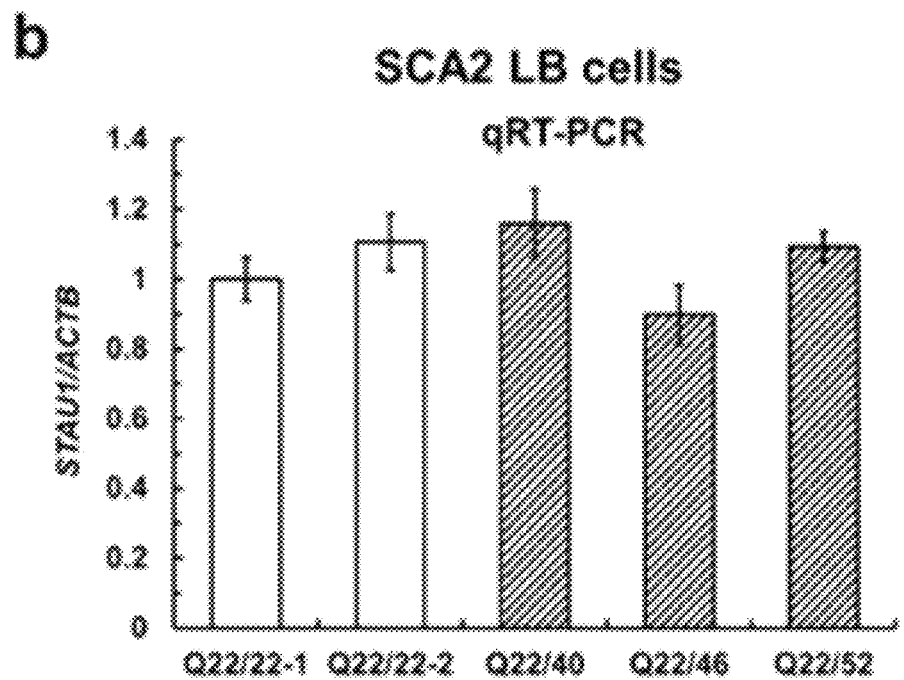
FIG. 11B is a graph showing Staufen1 transcript levels do not correspond to the differences in the steady state Staufen1 protein levels observed in SCA2-LBCs when compared to control cells.
Figure 11C:
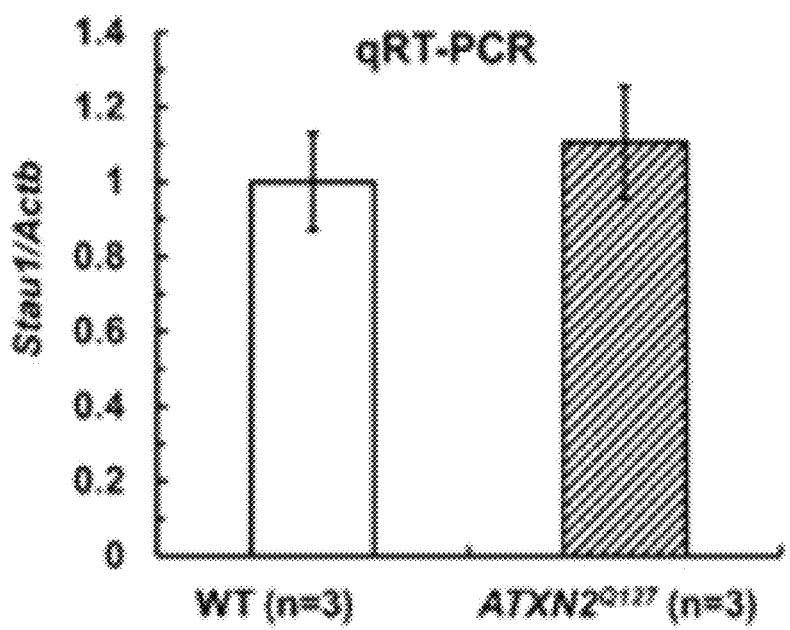
FIG. 11C is a graph showing a qRT-PCR analysis of cerebellar RNAs from ATXN2$^{Q127}$ mice showing unaltered Staufen1 transcript levels compared to wild-type littermates at 24 weeks of age. Gene expression levels were normalized to Actb.
Figure 11D:
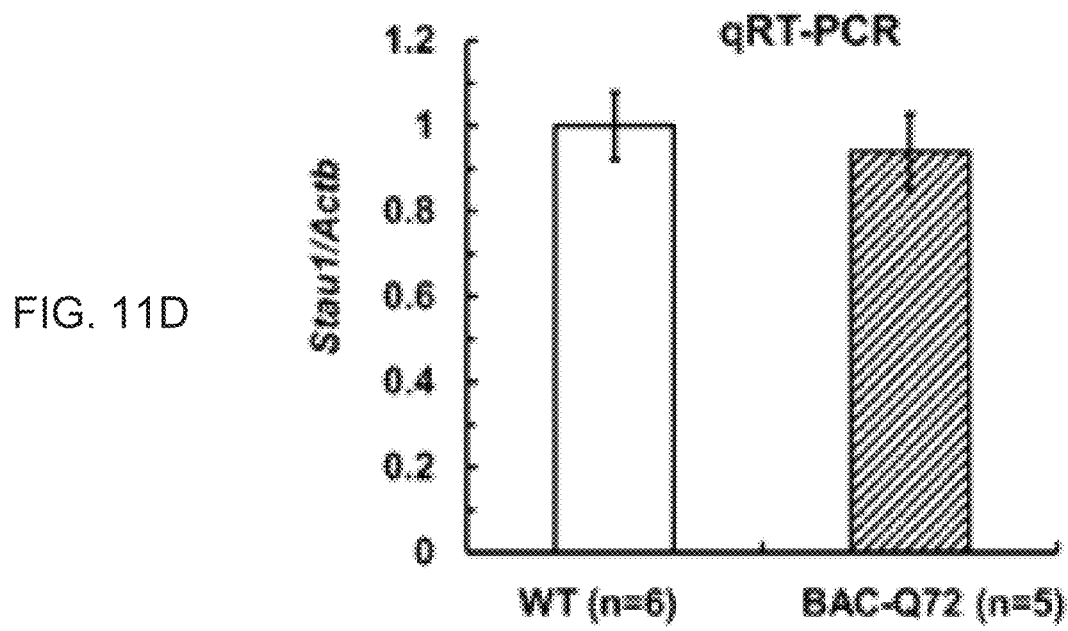
FIG. 11D is a graph showing a qRT-PCR analysis of cerebellar RNAs from BAC-Q72 mice showing unaltered Staufen1 transcript levels compared to wild-type littermates at 24 weeks of age. Gene expression levels were normalized to Actb.

The sensitivity of STAU1 to cellular stress prompted the examination of whether this pathway was active in other neurodegenerative conditions. Protein extracts were prepared from cerebella and spinal cords from animals overexpressing wild-type TDP-43, a mouse model of ALS. For these experiments, hemizygous transgenic animals were used that develop a phenotype late, at 15 months, facilitating testing Stau1 levels several months prior to onset of symptoms. There were significant increases in Stau1 and wild-type Atxn2 in both cerebellum and spinal cord (FIGS. 10E-10F), aligning with improved TDP-43 mouse survival with therapeutic reduction of wild-type Atxn2. STAU1 levels were also increased in ALS-patient FBs harboring the TDP-43$^{G298S}$ mutation (FIG. 10G). STAU1 levels were then determined in cell lines from patients with Huntington disease (HD) or SCA3. At physiologic conditions, STAU1 levels were not different in HD and SCA3 fibroblasts as compared with normal fibroblasts. When sodium arsenite was added to cultures, however, clear differences emerged. While only a modest STAU1 increase in response to arsenite was detected and only visible after 6 hr treatment, patient cells showed early and exaggerated responses to arsenite indicating hypersensitivity of the STAU1 pathway in these cells (FIG. 10H).

Figure 12:
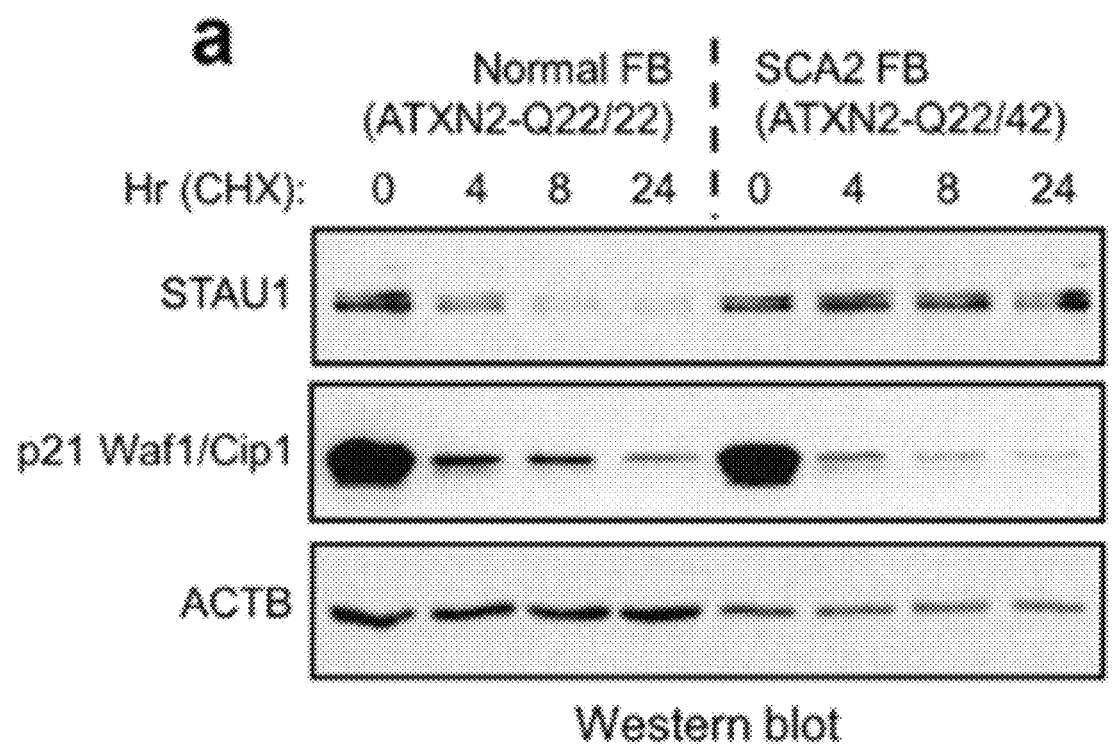
FIG. 12 is a western blot analysis where normal and SCA2 FBs were exposed to CHX (25 μg/ml) for different times from 0 to 24 hr, and protein extracts were immunoblotted for Staufen1. Staufen1 levels are quantified as a percentage of the value for the 0 time point and p21 Waf1/Cip1 protein levels are shown to verify CHX inhibition. Staufen1 protein stability was prolonged in SCA2 FBs compared to normal FBs. Loading control, β-actin found to be invariant over the treatment period. Representative blots of three independent experiments are shown.
Figure 13A:
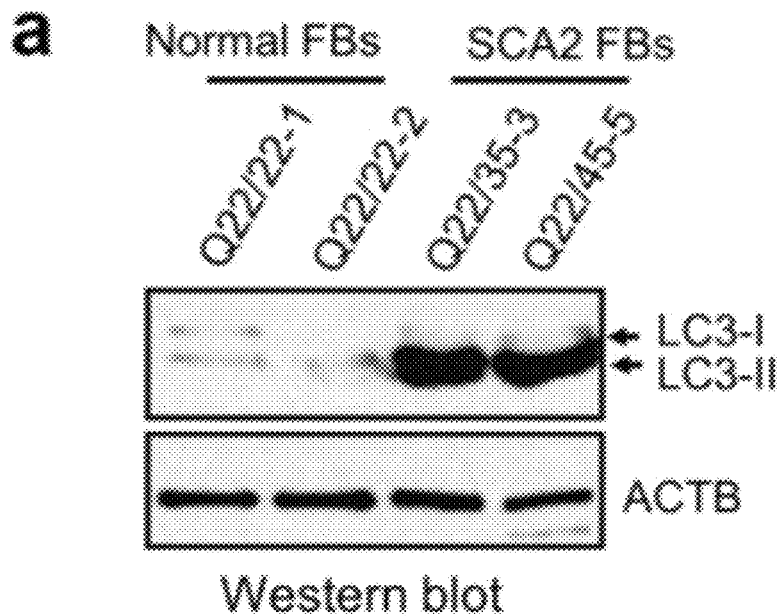
FIG. 13A is a western blot analysis illustrating that Autophagy is impaired in SCA2 FBs as indicated by increased levels of processed LC3-II.

As stress granules are degraded by autophagy, it was examined whether increased STAU1 levels were due to slowed turnover. STAU1 mRNA levels were not increased in patient cell lines and rodent cerebella by qRT-PCR (FIGS. 11A-11D), but STAU1 degradation was slowed, determined by a cycloheximide (CHX) pulse-chase experiment (FIG. 12 and FIG. 4C). Indeed, analysis of autophagic flux in SCA2 patient cells indicated that autophagy was impaired in the presence of mutant ATXN2 (FIG. 13A). In order to investigate STAU1 directly in autophagy, CRISPR/Cas9 genome editing was used to introduce an expanded CAG$^{58}$ (Q58) repeat into one ATXN2 allele in human SH-SY5Y cells. These cells were designated ATXN2-Q22/58 knock-in (KI) cells. ATXN2-Q22/58 KI cells had elevated STAU1 abundance, and ATXN2/STAU1 SGs (FIG. 13C and FIGS. 14A-14D). In prior studies, we had established key transcriptomic changes in SCA2 mouse models including reduced abundances in cerebellar PCP2, CACNA1G, and ITPR1 mRNAs. These changes were replicated in SH-SY5Y ATXN2-Q22/58 KI cells in the presence of one mutant ATXN2 allele (FIGS. 14A-14D).

Figure 13B:
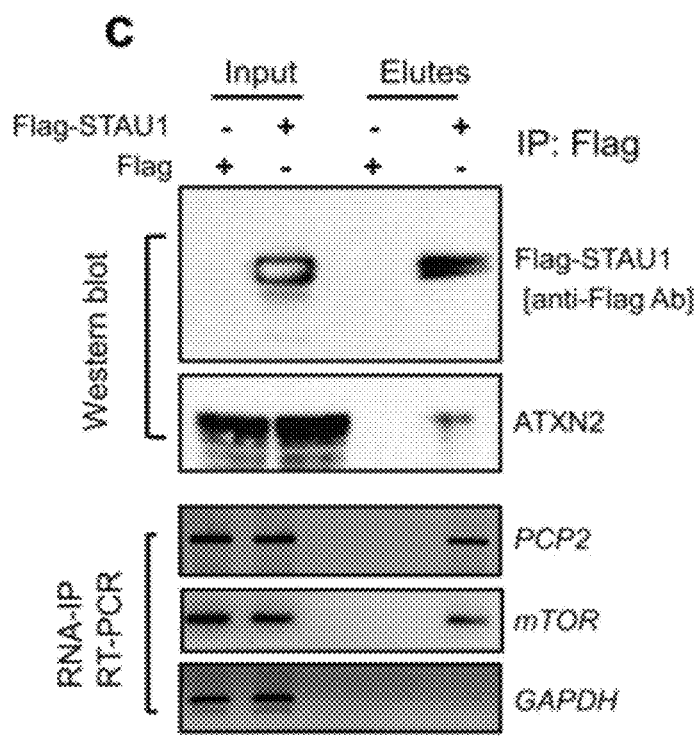
FIG. 13B is a plot illustrating Flag immunoprecipitation of SH-SY5Y cell extracts expressing Flag-tagged STAU1 (non-RNAse A treated). Flag-Staufen1 pulled down ATXN2 protein, and PCP2 and mTOR mRNAs on western blot and RT-PCR.
Figure 13C:
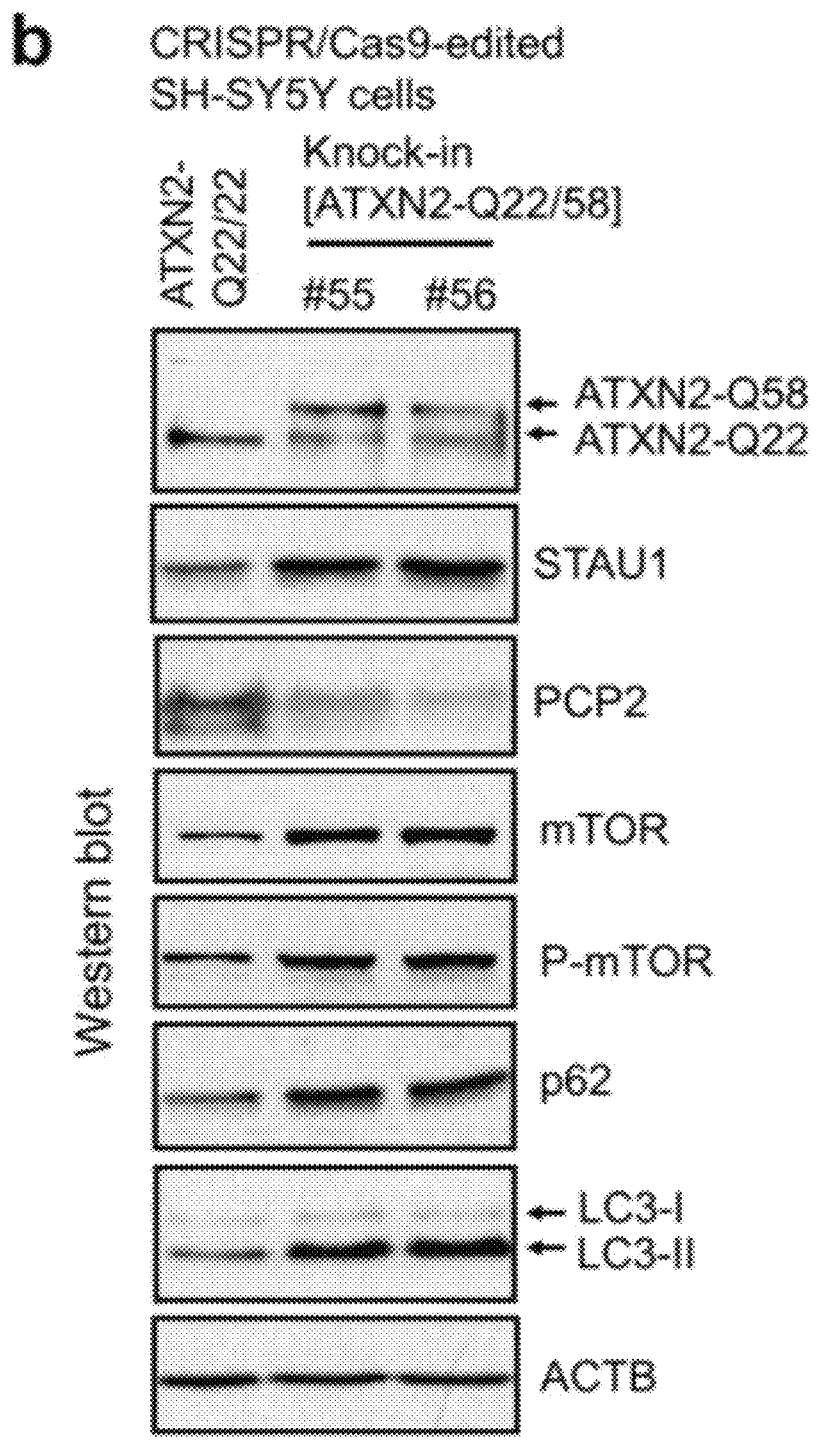
FIG. 13C is a western blot analysis illustrating Introduction of an expanded ATXN2 allele into SH-SY5Y cells by CRISPR/Cas9 editing results in STAU1 increase and autophagic dysfunction as shown by increases in mTOR, P-mTOR, p62 and processed LC3-II on western blots. The differentially regulated cerebellar transcript PCP2 is decreased in this cell model. β-actin was used as loading control.
Figure 14B:
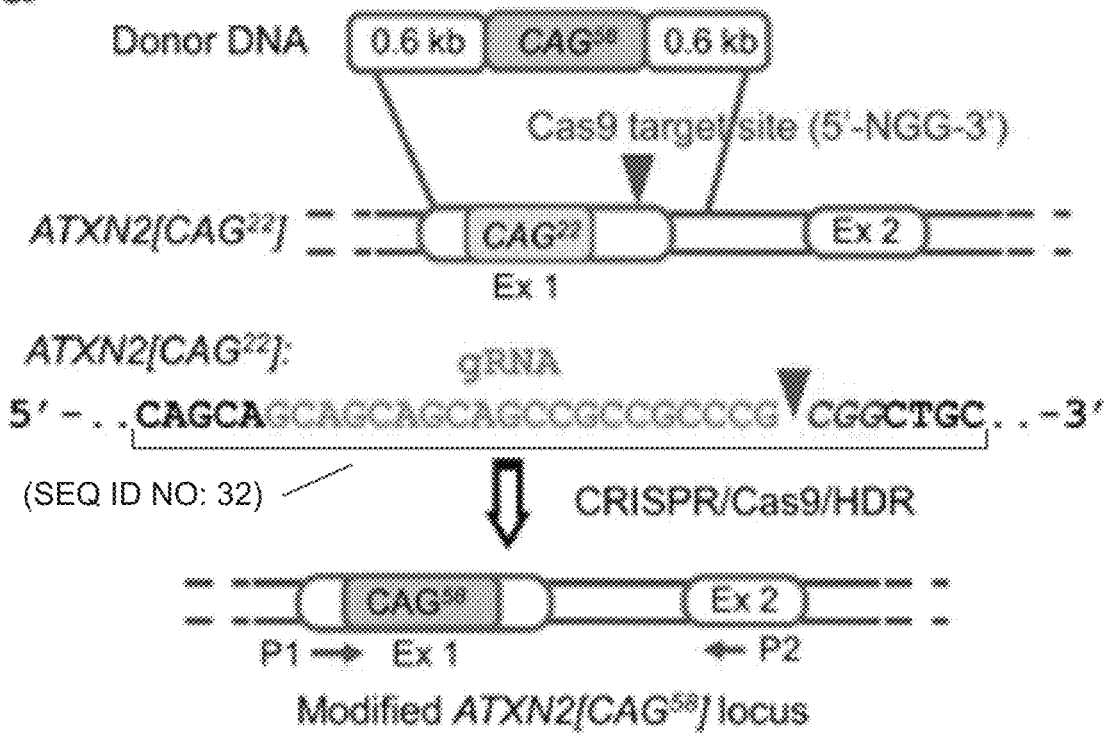
FIG. 14B presents RT-PCR analyses of some identified ATXN2-Q22/58 Knock-in clones.
Figure 14B:
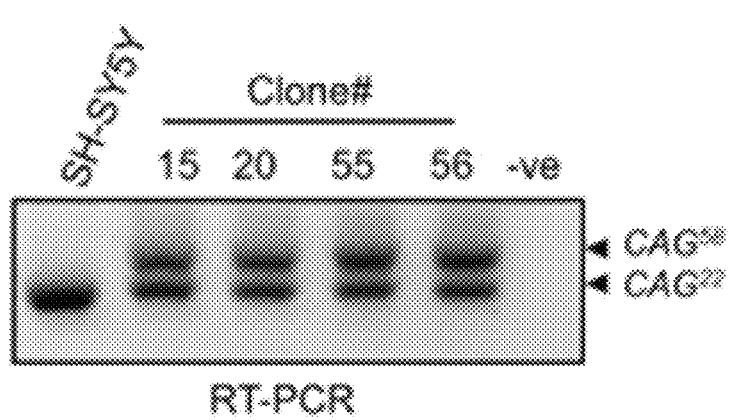
Figure 14C:
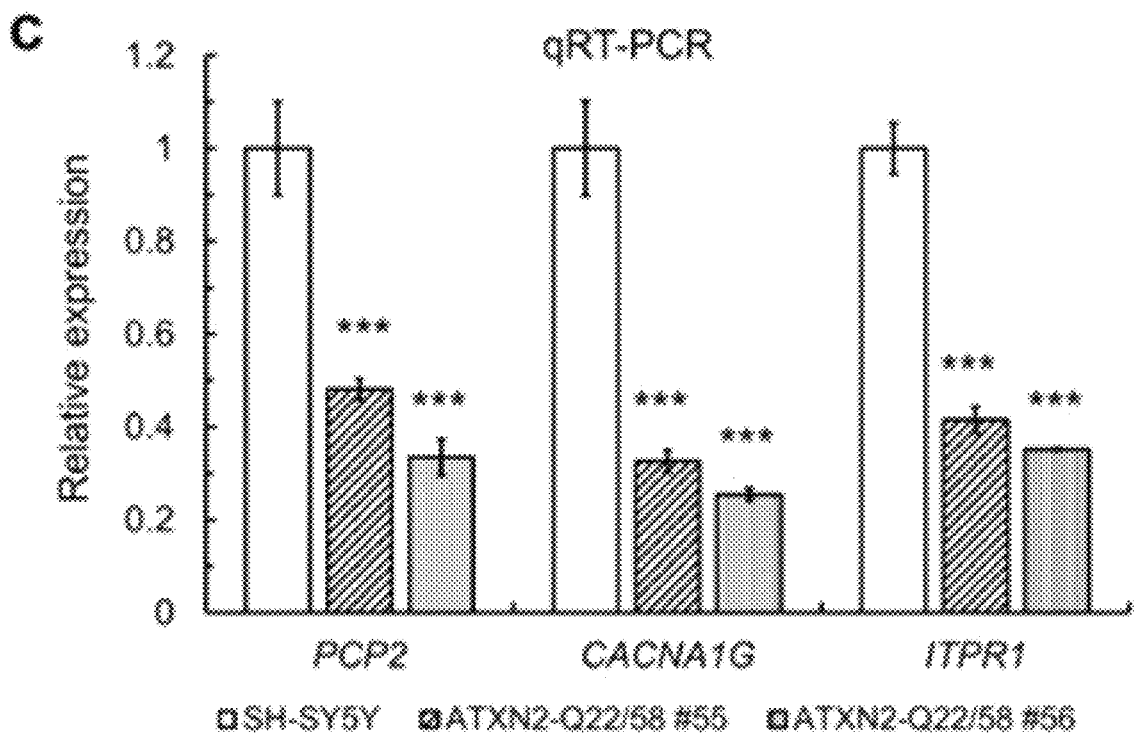
FIG. 14C is a graph showing CRISPR/Cas9 edited ATXN2-Q22/58 KI cells mirror SCA2 phenotypes including Staufen1 abundance (FIG. 13B; western blotting) and dysregulation of transcripts (PCP2, CACNA1G and ITPR1) associated with SCA2 in vivo analyzed by qRT-PCR. Data are means±SD, ***P<0.01, Student t-test.
Figure 14D:
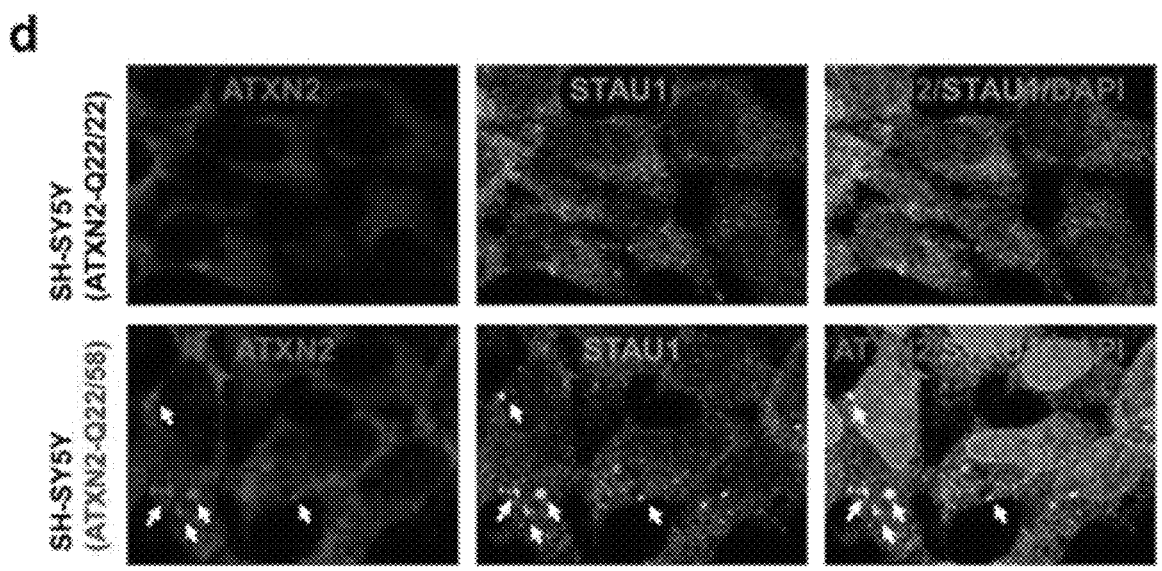
FIG. 14D presents images showing ATXN2 and Staufen1 co-localize in SG-like aggregates. Representative immunohistochemical images from wild-type and ATXN2-Q22/58 KI cells stained with antibodies directed against Staufen1 (green) and ATXN2 (red) showing presence of SG-like structures positive for both ATXN2 and Staufen1. All images for a respective antibody were taken at the same exposure times. Scale bar=100 μM.
Figure 15A:
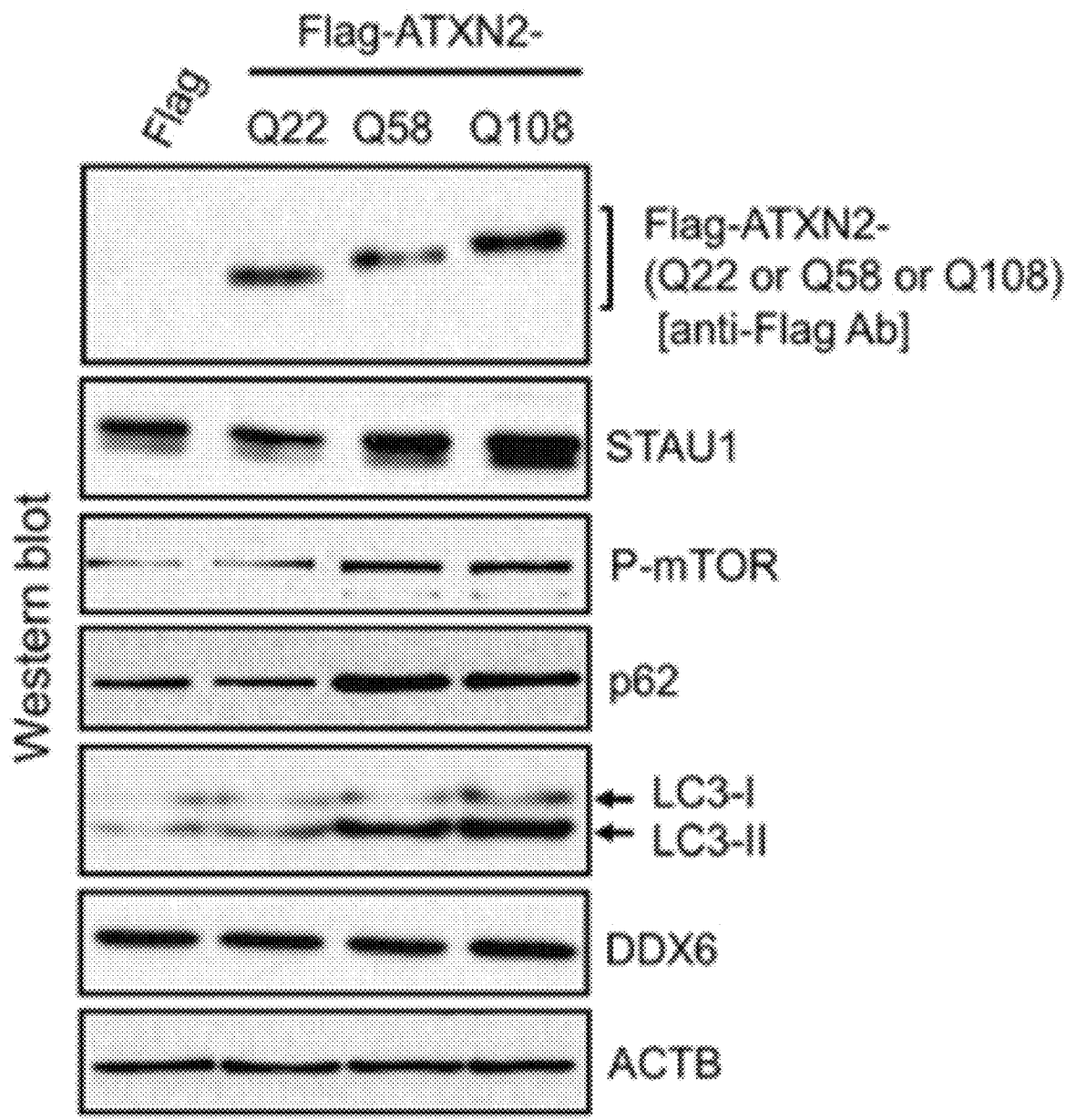
FIG. 15A is a western blot analysis of Mutant ATXN2 overexpressed SH-SY5Y cells showing increased levels of Staufen1, P-mTOR, p62 and processed LC3-II.
Figure 15B:
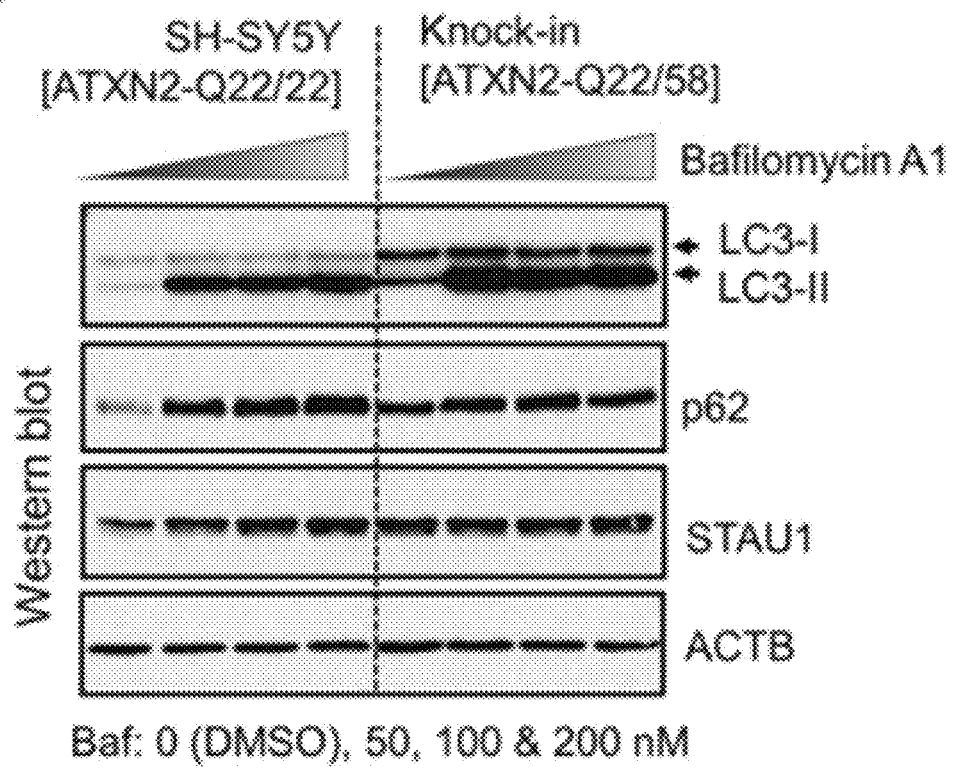
FIG. 15B is a western blot analysis showing Bafilomycin A1 lowers Staufen1 clearance. SH-SY5Y and ATXN2-Q22/58 knock-in cells were treated dose-wise with Baf for 6 h and analyzed by western blotting. Baf treatment showing dose-wise increased levels of processed LC3-II along with p62 and Staufen1 for both cell types compared to untreated cells.

Compared with wild-type SH-SY5Y cells, the presence of endogenous mutant ATXN2 significantly increased abundance of active mechanistic target of rapamycin (mTOR), sequestosome 1 (SQSTM1/p62) and processed LC3-II (the lipidated isoform of LC3-I) (FIG. 13C). It was verified that the same autophagy changes including STAU1 abundance occurred in SH-SY5Y cells following overexpression of ATXN2 harboring Q58 and Q108 repeats but not Q22 (FIG. 15A). Consistent with inhibited autophagy, we showed that SH-SY5Y cells treated with bafilomycin A1 (Baf), an inhibitor of autophagosome-lysosome fusion, expressed p62 and processed LC3-II similar to cells expressing ATXN2-Q58 (FIG. 15B). However, the slight elevation of LC3-II with Baf treatment suggested that partial autophagy competence persisted in ATXN2-Q22/58 KI cells.

Figure 15C:
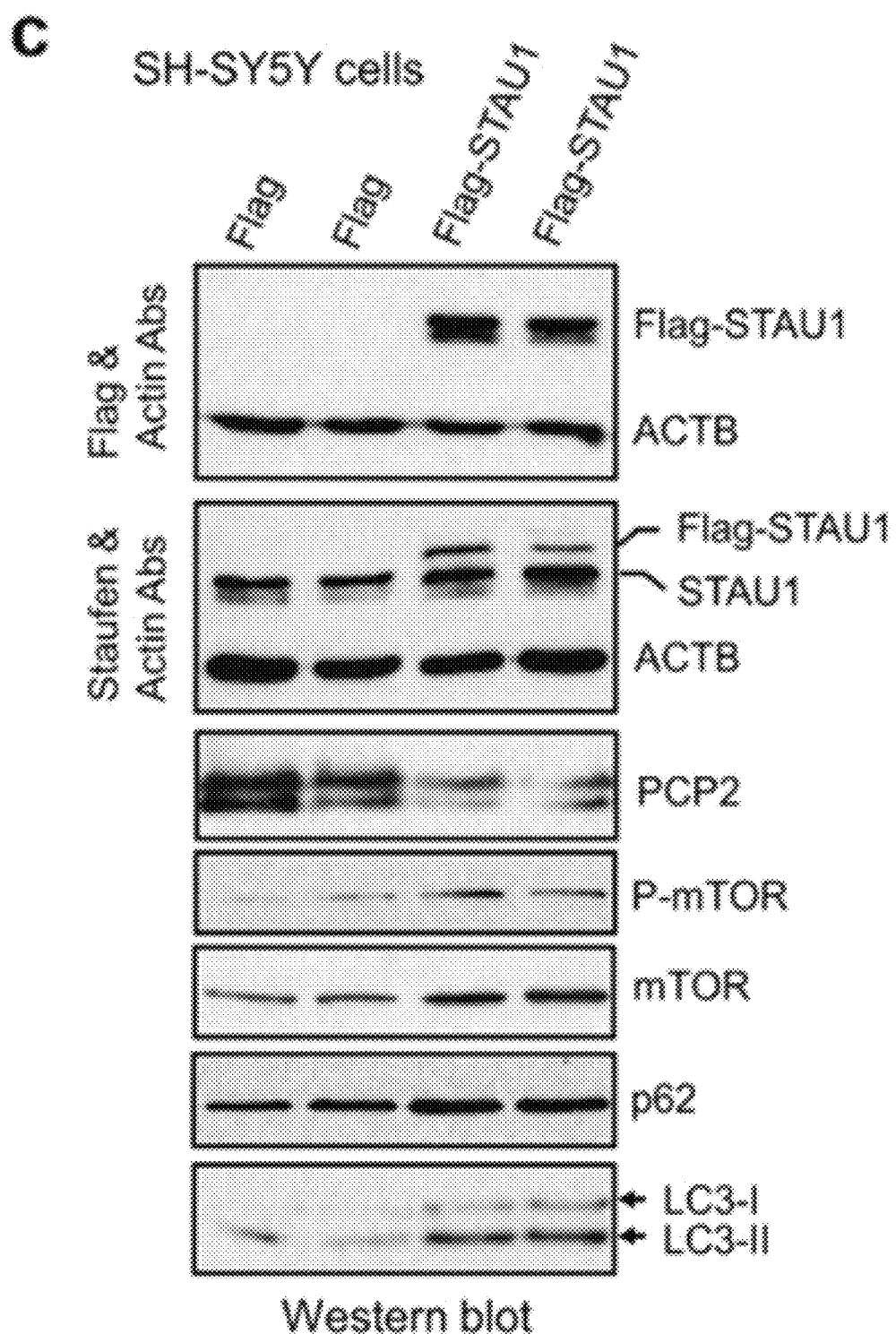
FIG. 15C is a western blot analysis of Staufen1 overexpressed SH-SY5Y cell extracts showing reduced PCP2 protein levels (differentially regulated cerebellar transcript Pcp2) and increased P-mTOR, mTOR, p62 and LC3-II levels. β-actin was used as loading control and representative blots of three independent experiments are shown.

To test whether changes in autophagy were largely due to increased STAU1 levels, STAU1 was exogenously expressed in SH-SY5Y cells. This resulted in increased expression of activated P-mTOR, mTOR, p62 and LC3-II, as well as reduction of the STAU1 target, PCP2 protein (FIG. 15C). Rapamycin- or rapalog-induced mTOR signaling inhibition has been shown to induce autophagy, reduce polyglutamine toxicity and motor deficits in HD models, and ameliorate motor phenotypes in mice modeling autism spectrum disorders (ASDs). Indeed, it was demonstrated that STAU1 levels and the abnormal levels of activated P-mTOR, mTOR, p62, and LC3-II were restored by rapamycin treatment, as well as by lowering either STAU1, ATXN2, or mTOR by RNAi in ATXN2-Q22/58 KI cells (FIGS. 16A-16B and FIGS. 17A-17B). These experiments also showed that STAU1 acted downstream of ATXN2 as ATXN2-RNAi reduced STAU1, but STAU1-RNAi did not change ATXN2 levels. Furthermore, STAU1 and mTOR functionally interact in a reciprocal fashion as RNAi to either one can normalize the level of the other protein.

One of the functions of STAU1 is targeting subsets of mRNAs for degradation via a mechanism similar to nonsense-mediated decay, referred to as STAU1-mediated RNA decay (SMD). In genome-wide transcriptome analysis in SCA2 animal models, it was noticed that a large number of mRNAs were severely decreased in abundance. Some of these RNAs had also been identified as STAU1 interactors by hiCLIP. SMD for a given mRNA predicts that STAU1 binds to the 3'UTR of the respective mRNA.

To test SMD for PCP2 mRNA, STAU1 was shown to bind PCP2 directly, and that binding was abolished in an mRNA lacking the 3'UTR (FIG. 13B and FIGS. 6B-6C). This is further supported by restoration of PCP2 expression in SCA2-patient LBCs after reduction of STAU1 via RNAi, and by the ability for STAU1 to lower PCP2 expression by way of an interaction with the PCP2 3'UTR (FIGS. 18A-18C and FIGS. 19A-19B). SMD may explain increased RNA abundance for a subset of mRNAs identified in SCA2 patient cells and animal models by STAU1 binding to the 3'UTRs of the respective mRNAs. STAU1 also regulates the translational efficiency via 5'UTR and polysome association[3]. Consistent with this, interaction between Staufen1 and a 5'UTR-mTOR RNA by STAU1 immunoprecipitation was shown (FIG. 13B), supporting its role in mTOR translation.

Figure 16A:
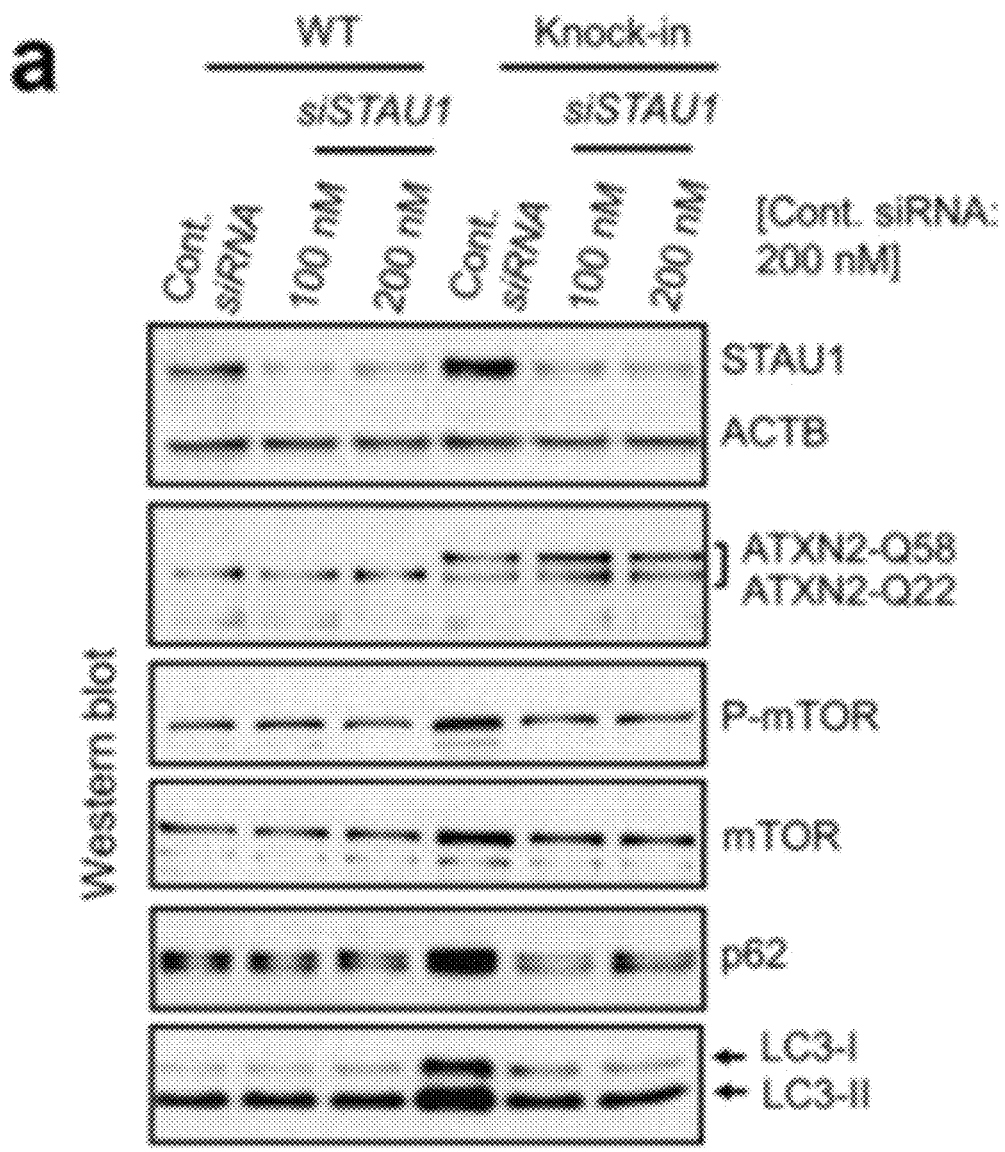
FIG. 16A is a western blot analysis showing Staufen1 depletion restores autophagic pathway proteins in ATXN2-Q22/58 KI cells. Cells were transfected with STAU1 siRNA and analyzed by western blotting. Staufen1 depleted ATXN2-Q22/58 KI cells show restoration of autophagic pathway proteins without affecting ATXN2 steady-state levels.
Figure 16B:
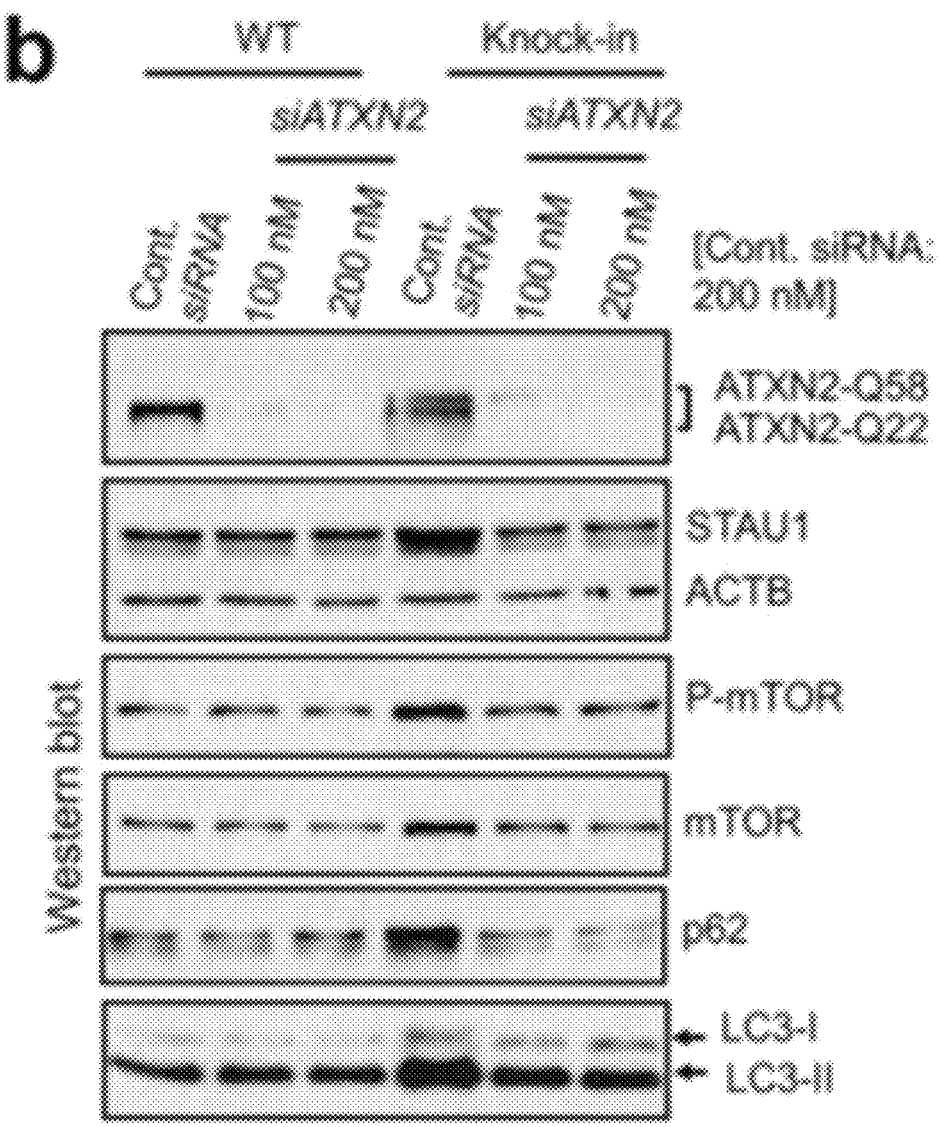
FIG. 16B is a western blot analysis showing ATXN2 siRNA lowers Staufen1 abundance, and normalizes autophagic pathway proteins in ATXN2-Q22/58 KI cells.
Figure 16C:
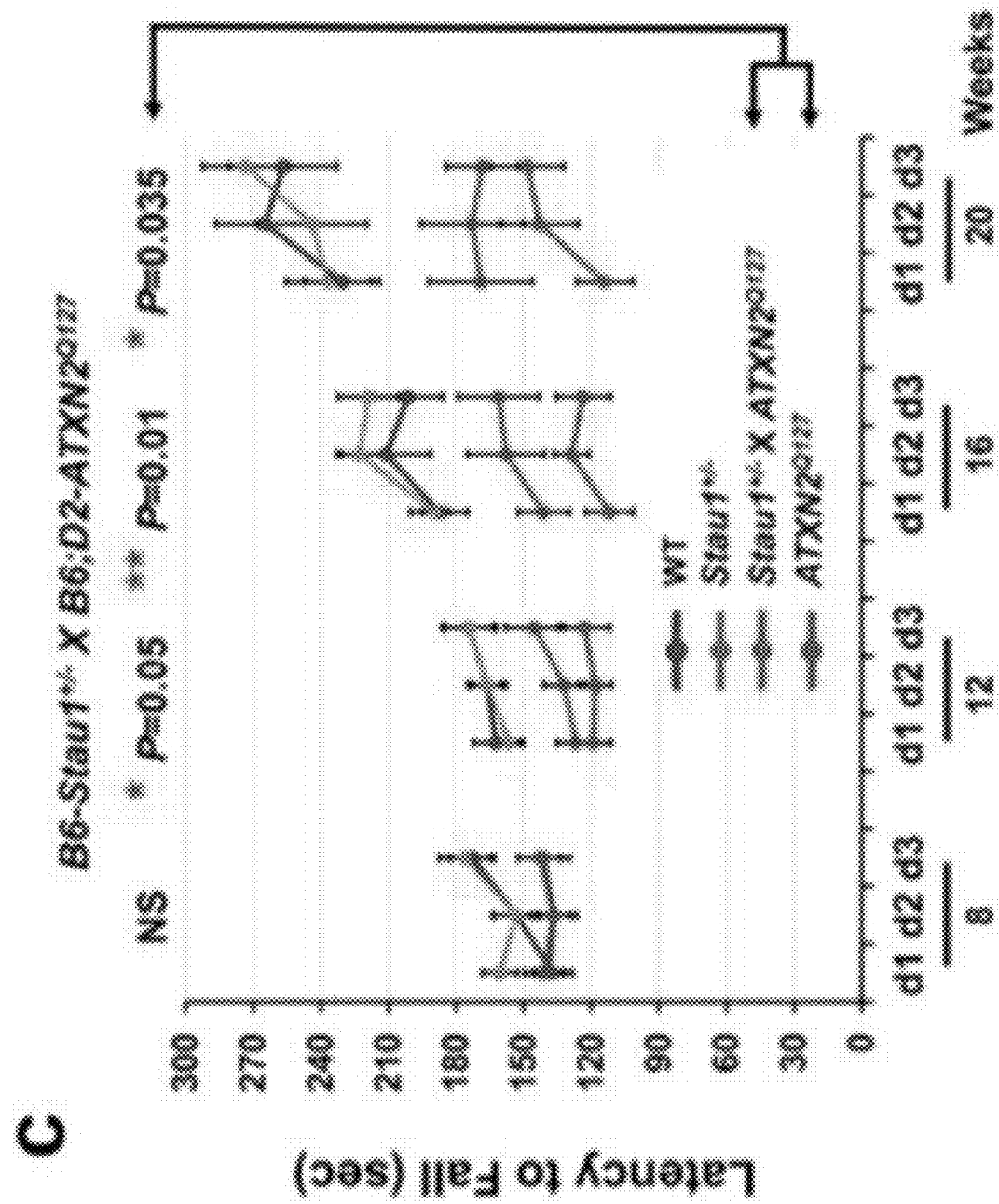
FIG. 16C is a graph showing Stau1 haploinsufficiency improves abnormal motor behavior of $ATXN2^{Q127}$ mice as determined by rotarod behavior at 8, 12, 16 and 20 weeks of age. $ATXN2^{Q127}$; Stau1$^{+/-}$ mice (green) have improved rotarod performances compared with $ATXN2^{Q127}$ mice (red) starting at 12 through 20 weeks of age; N=9-15 mice per group. Values shown are mean±SE. Significance was determined using generalized estimating equations (GEE). NS, nonsignificant, *$P<0.05$, **$P<0.01$.
Figure 16D:
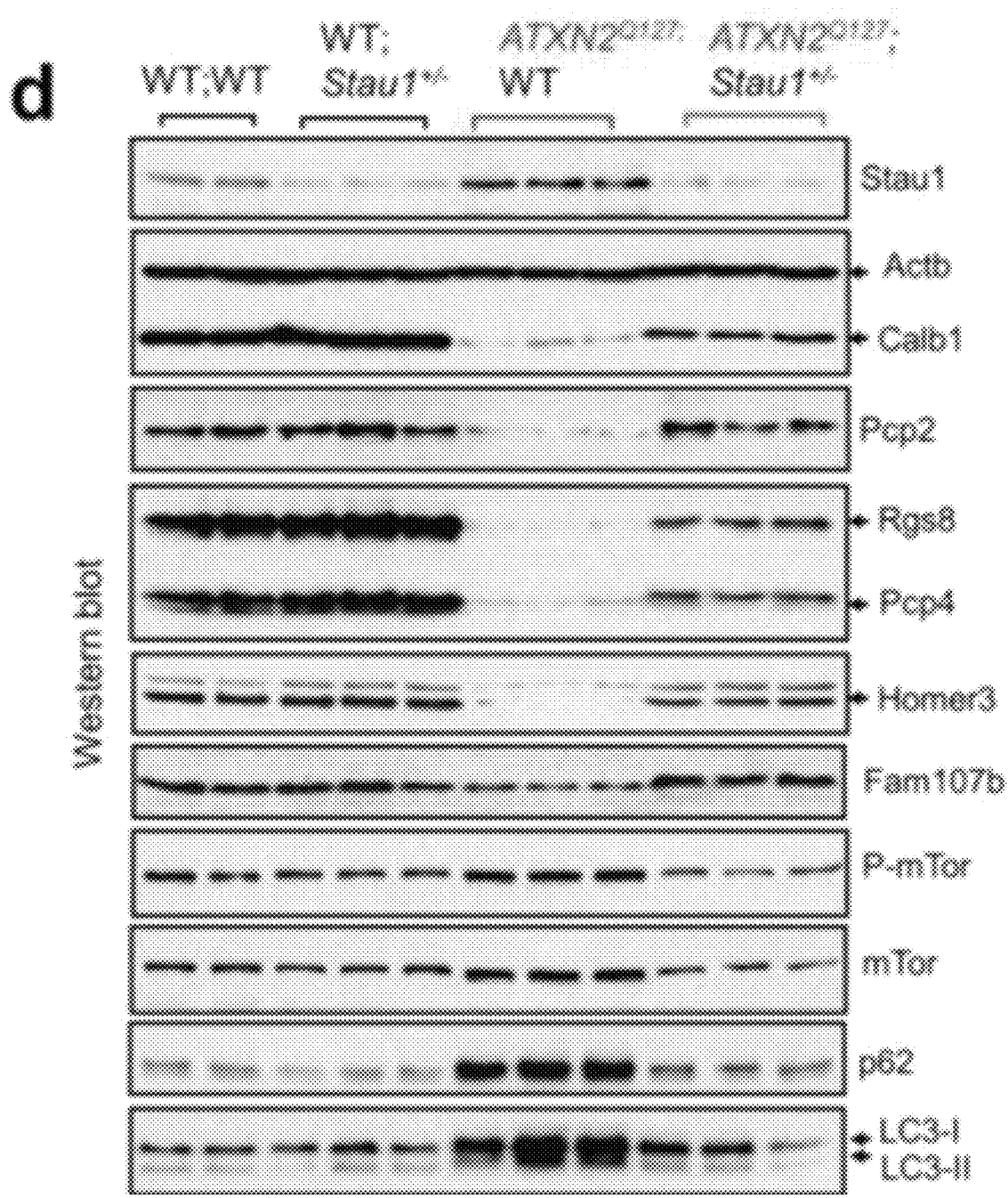
FIG. 16D is a western blot analysis of cerebellar extracts from wild-type and transgenic animals with normal and 50% Staufen1 reduction at 20 weeks of age. The PC proteins tightly correlate with disease progression in two SCA2 mouse models. Phosphorylated mTor, total mTor, p62, and LC3-II are markers of autophagosome function. Each lane represents a cerebellar extract from an individual mouse. β-actin is used as a loading control and the blots are from three replicate experiments.
Figure 16E:
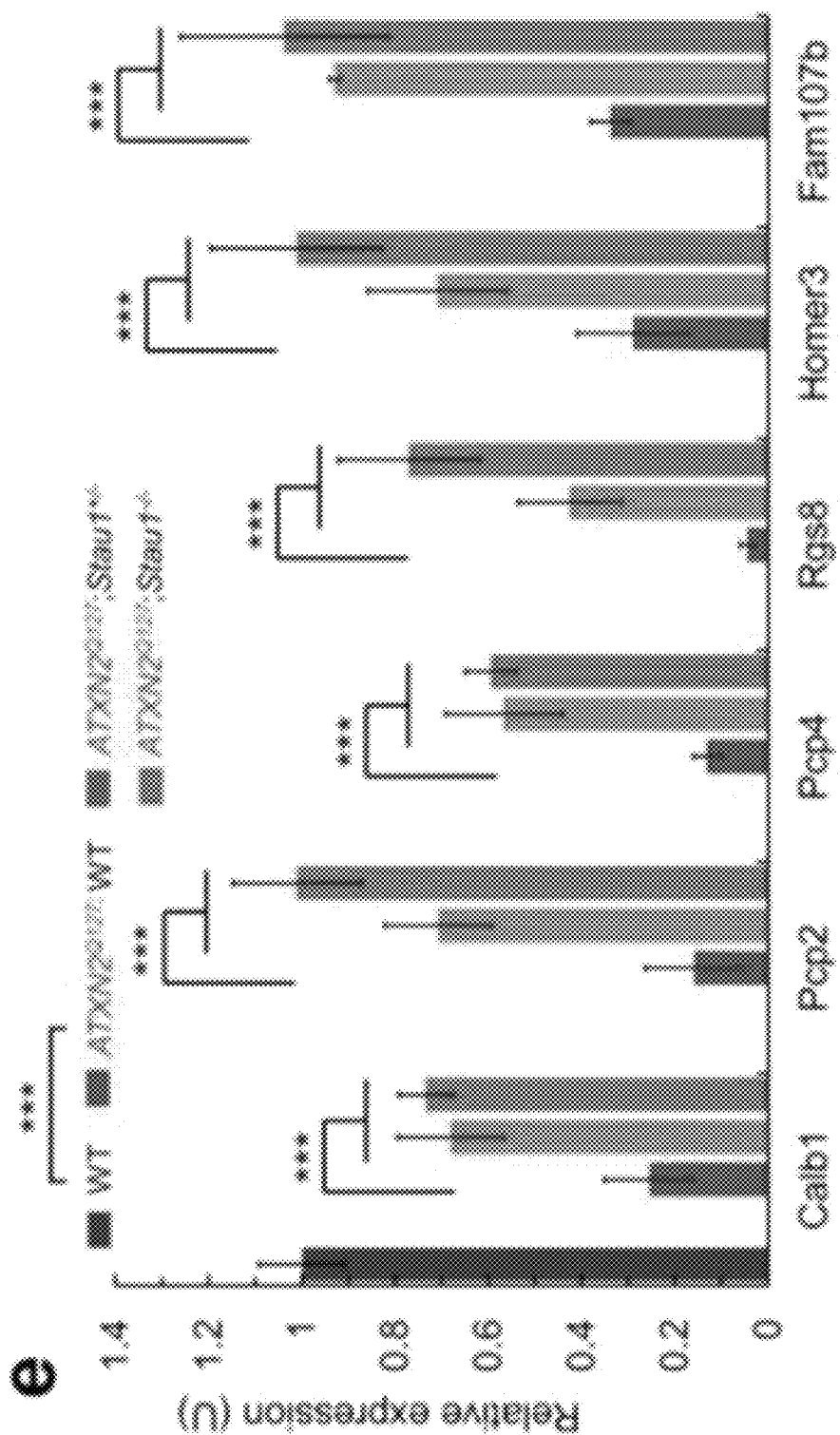
FIG. 16E is a graph of a quantitative analysis of western blots shown in FIGS. 16D and 20. Data are means±SD, ***$P<0.001$, Student t-test.
Figure 16F:
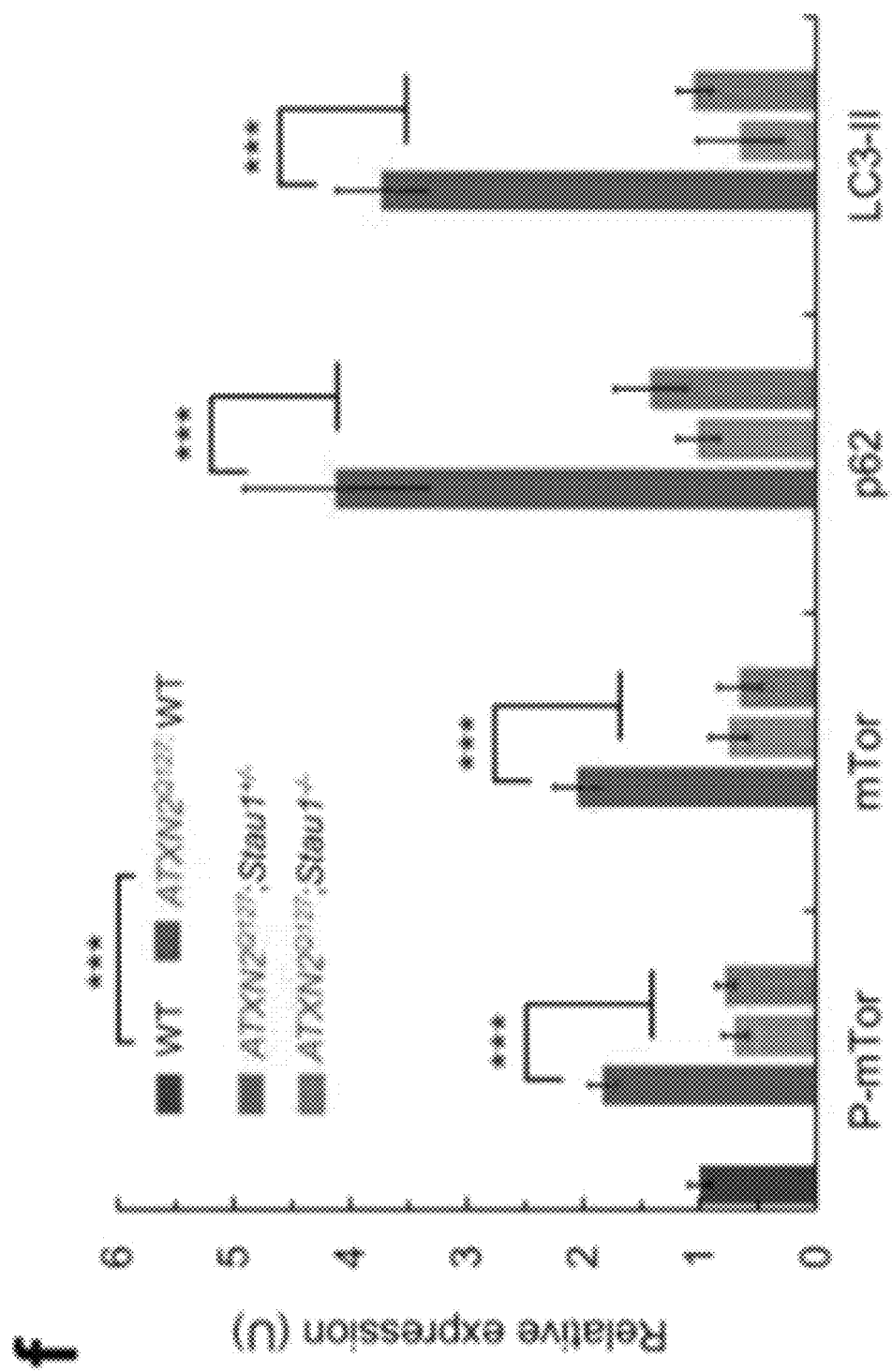
FIG. 16F is a graph of a quantitative analysis of western blots shown in FIGS. 16D and 20. Data are means±SD, ***$P<0.001$, Student t-test.
Figure 17A:
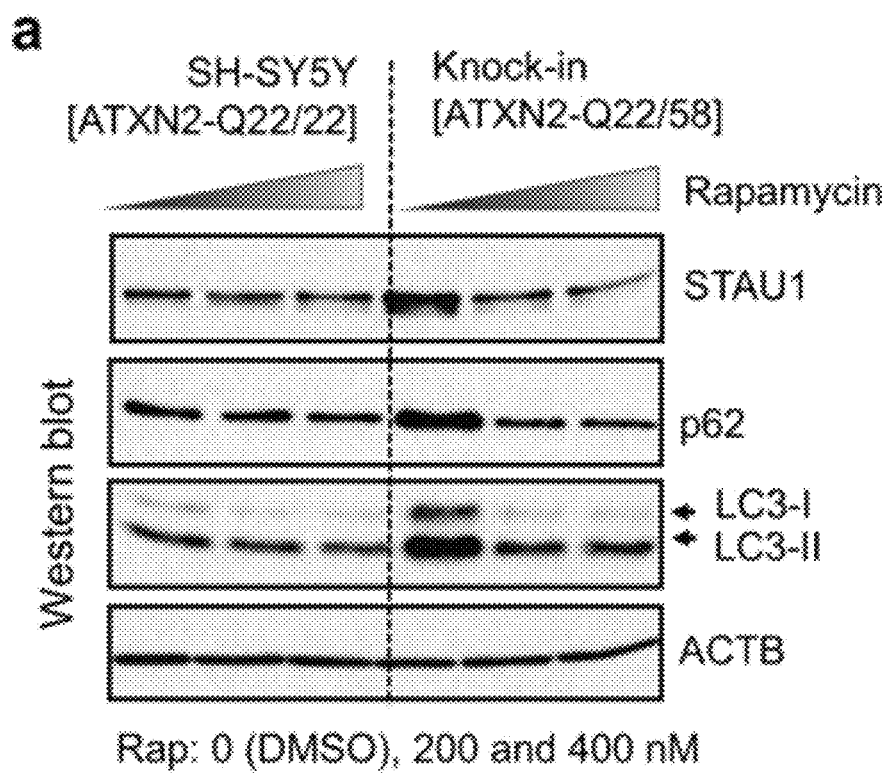
FIG. 17A is western blot analysis where SH-SY5Y and ATXN2-Q22/58 KI cells were treated dose-wise with Rapamycin for 24 h followed by western blotting. Rap-induced mTOR inhibition dose-wise decreased levels of elevated Staufen1 along with p62 and LC3-II in ATXN2-Q22/58 KI cells without affecting those levels in control SH-SY5Y cells. β-actin was used as loading control and representative blots of three independent experiments are shown.
Figure 17B:
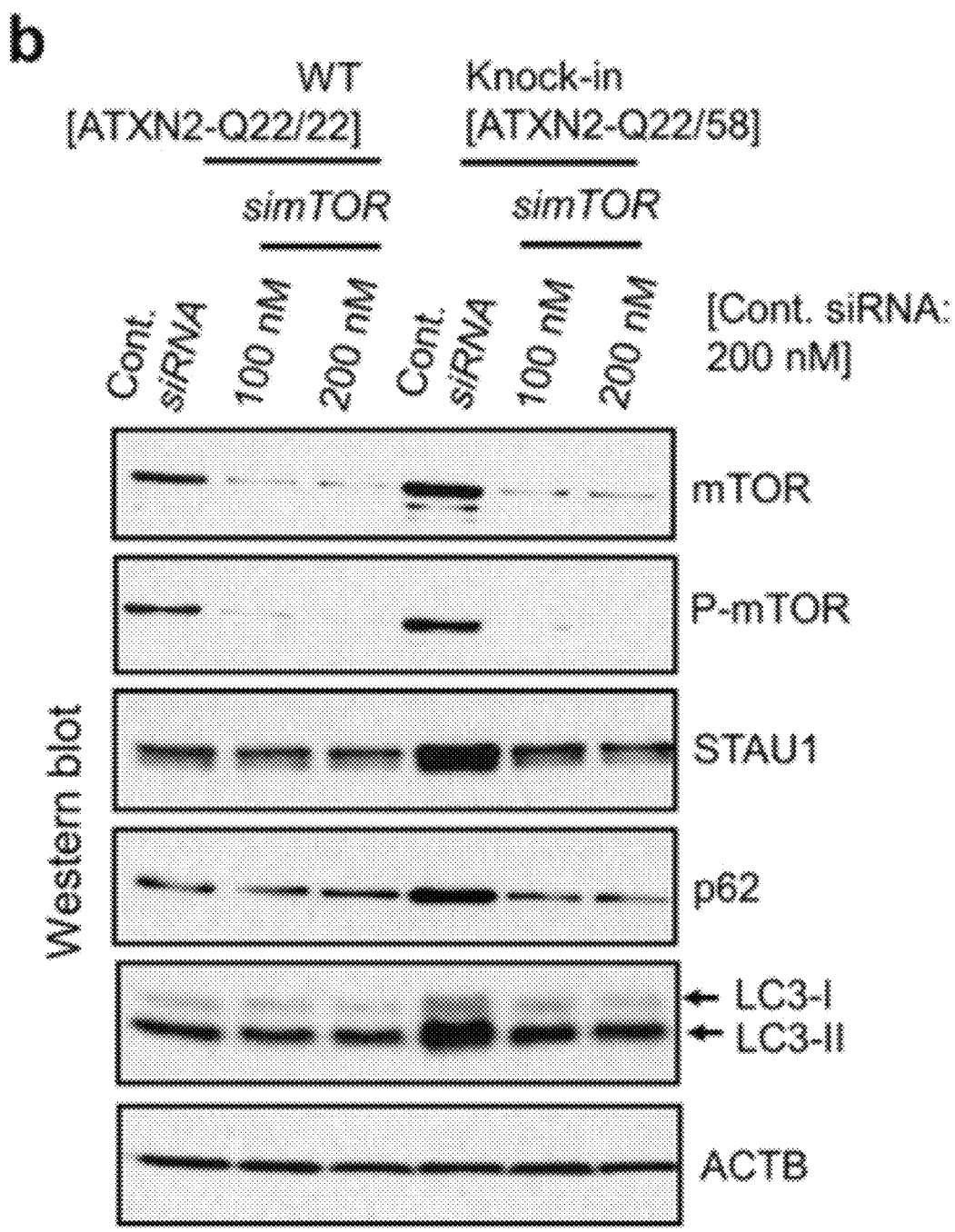
FIG. 17B is a western blot analysis showing RNAi-mediated mTOR depletion lowers Staufen1 and improves autophagy marker proteins. SH-SY5Y and ATXN2-Q22/58 KI cells were transfected with mTOR RNAi and cells were analyzed by western blotting at 4 days post-transfection. mTOR RNAi-mediated mTOR and phospho-mTOR depletion showing reduced Staufen1 and autophagic pathway protein component levels in ATXN2-Q22/58 KI cells without affecting those levels in control SH-SY5Y cells. β-actin was used as loading control and representative blots of three independent experiments are shown.
Figure 18C:
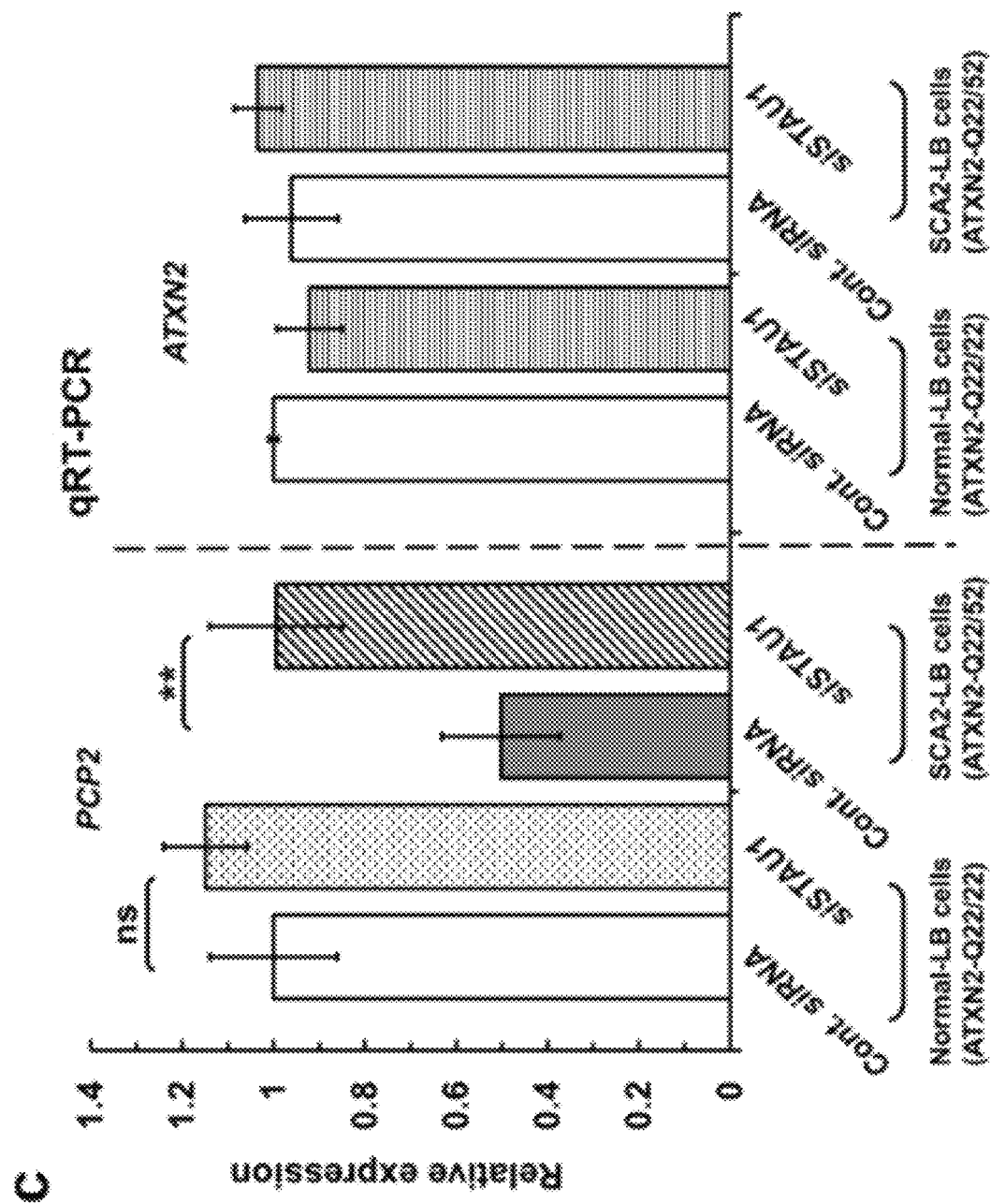
FIG. 18C is a graph illustrating Staufen1 depletion was associated with increased PCP2 transcript levels in SCA2-LBCs and where matched cultures were used for qRT-PCR analyses to measure PCP2 transcript levels. PCP2 mRNA was unresponsive to Staufen1 knockdown in normal LBCs. Staufen1 silencing did not alter ATXN2 transcript steady-state levels in normal and SCA2-LBCs. β-actin and GAPDH RNA were used as internal controls for western blot and qRTPCR analyses, respectively. Abundances relative to actin determined densitometrically. The results from three independent experiments are shown. Data are means±SD, **$P<0.01$, Student t-test.
Figure 19A:
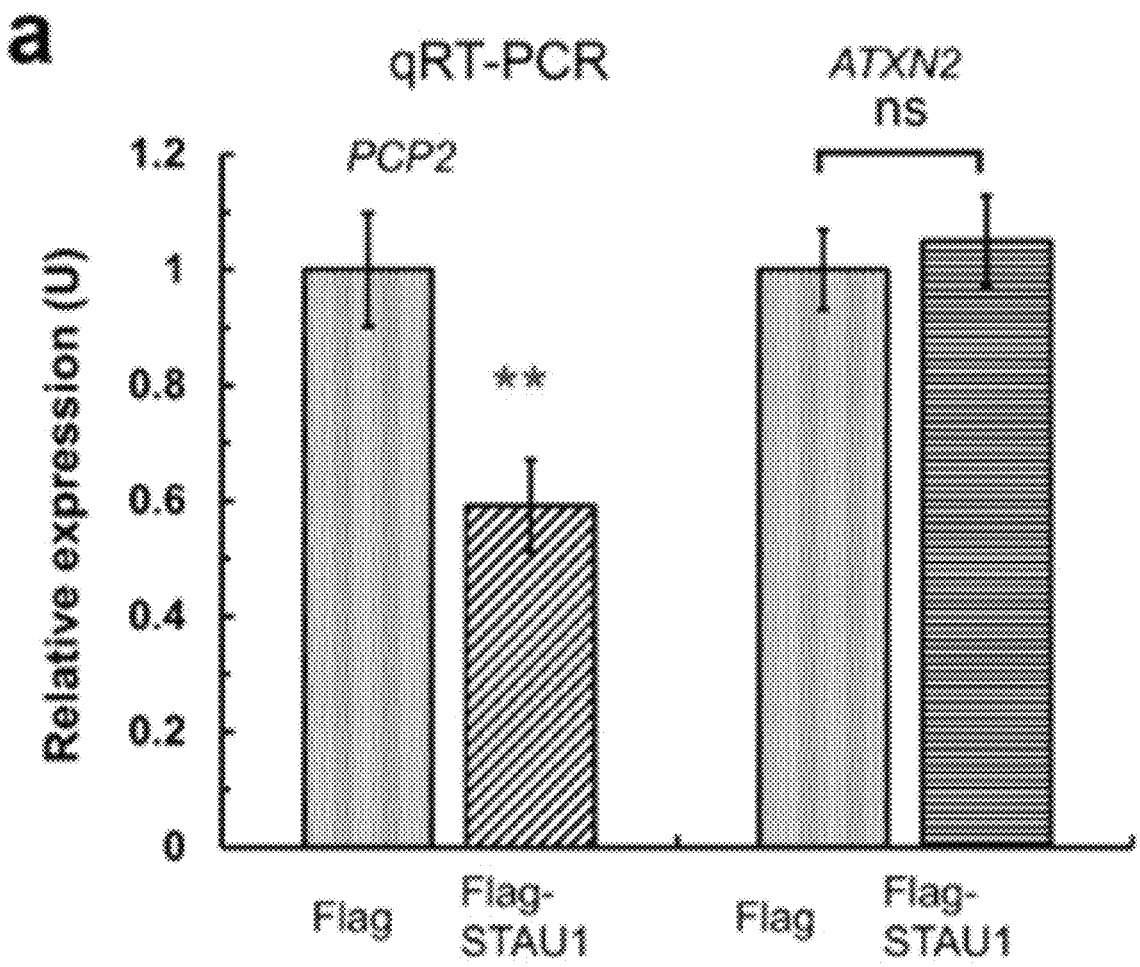
FIG. 19A is a graph illustrating Staufen1 overexpression reduced PCP2 mRNA abundance. Total RNA was isolated from the one aliquot of harvested SH-SY5Y cells (FIG. 15C) overexpressing Flag-tagged Staufen1 and subjected to qRT-PCR analyses. Cells overexpressing Staufen1 have decreased mRNAs for PCP2 but not ATXN2 compared with controls. Gene expression levels were normalized to GAPDH.
Figure 19B:
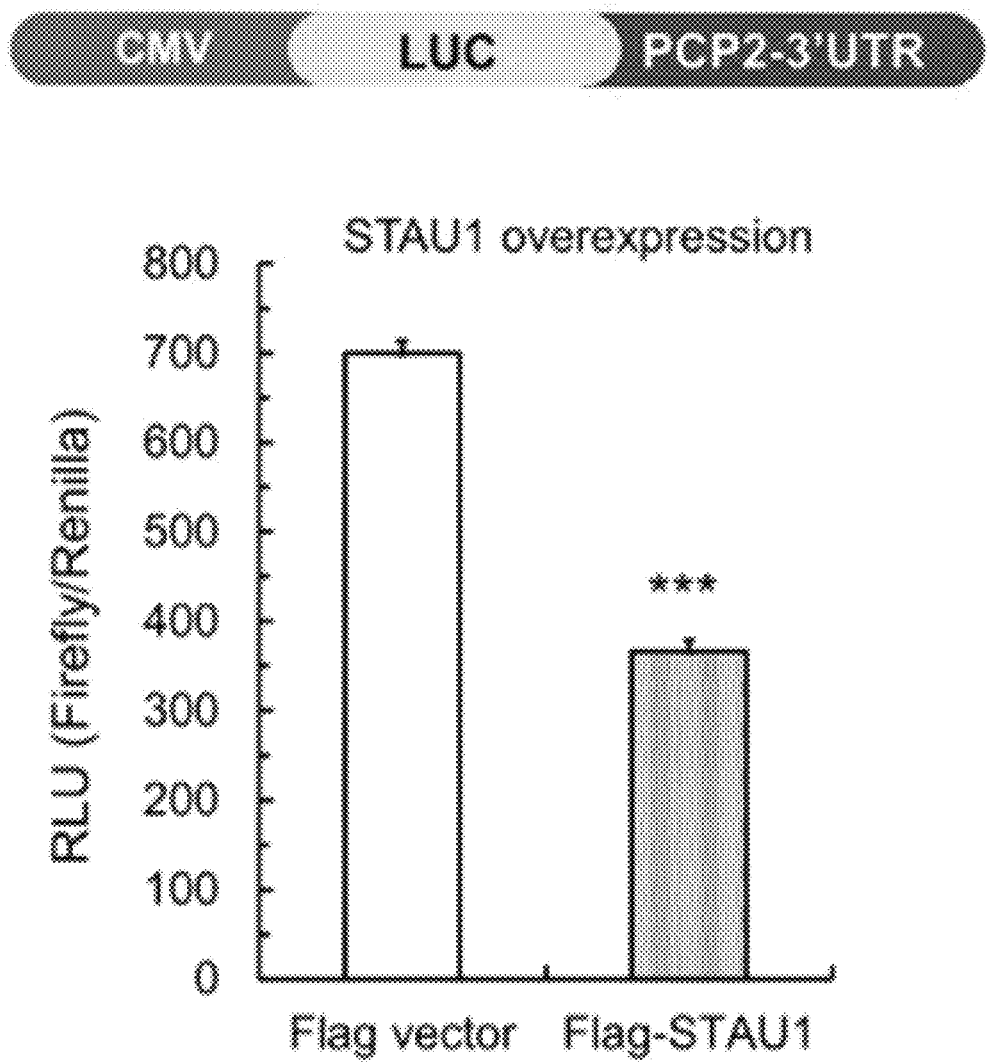
FIG. 19B is a graph of the co-transfection of Flagtagged STAU1 with luciferase-PCP2-3'UTR and Renilla luciferase expression plasmids in SHSY5Y cells demonstrating reduction of luciferase activity and where the 3'UTR of PCP2 was cloned downstream of luciferase expression plasmid. Luciferase expression was normalized with Renilla luciferase expression to control transfection equalities. Data are means±SD, $P<0.01$, *$P<0.001$, Student t-test.
Figure 20:
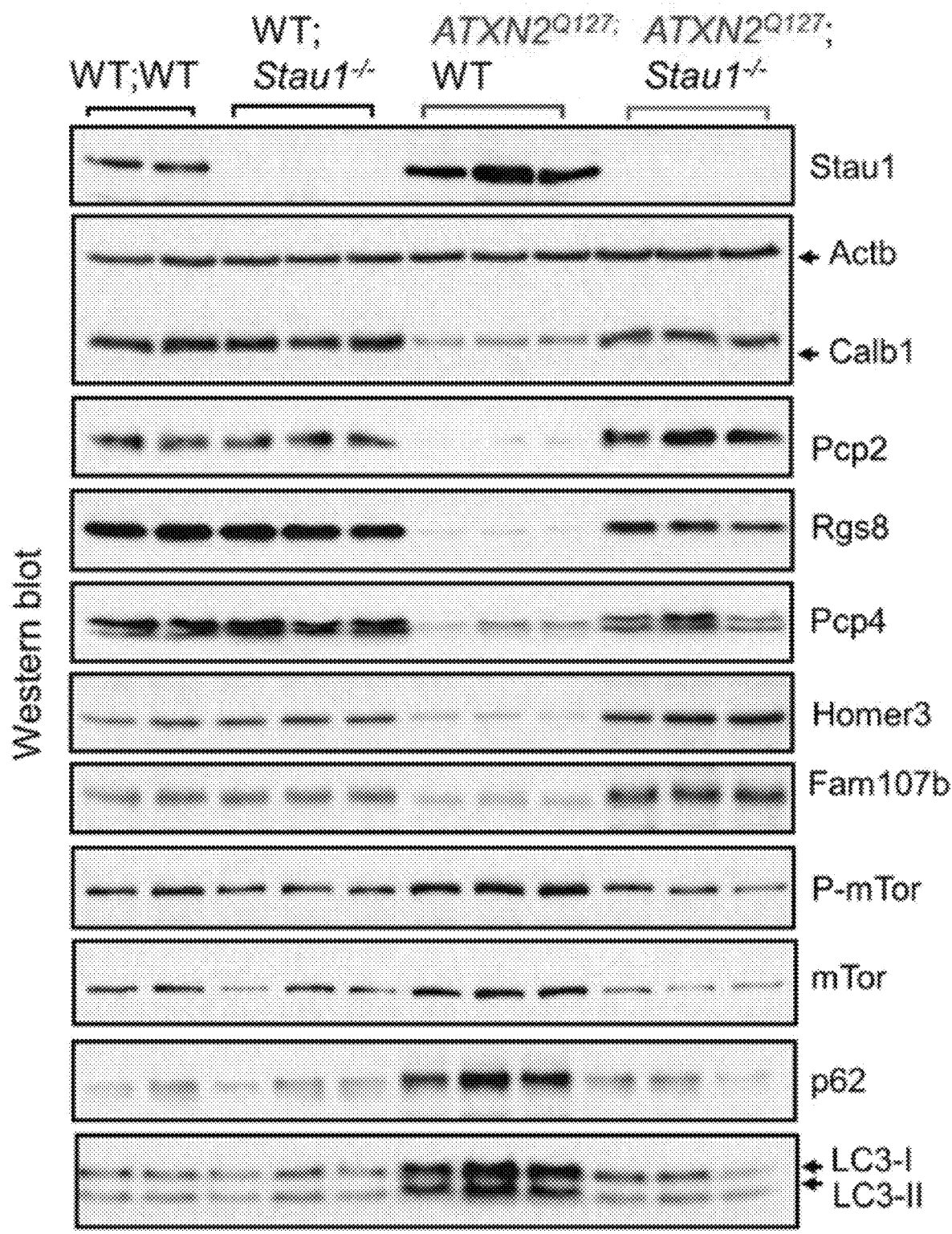
FIG. 20 is a Western blotting analysis of cerebellar extracts from crossed ATXN2Q127; Stau1−/− at 18 weeks of age showing restoration of Calb1, Pcp2, Pcp4, Rgs8, Homer3, Fam107b and autophagic pathway proteins. Each lane represents cerebellar extract from an individual mouse. β-actin was used as loading control and the blots are from three replicate blots. Quantitative analysis of western blots shown in FIGS. 16E-16F.

To test targeting Stau1 in vivo, we used a well characterized model of cerebellar neurodegeneration expressing mutant ATXN2$^{Q127}$ in PCs. ATXN2$^{Q127}$ mice develop progressive behavioral and proteomic deficits with an onset at 8 weeks. We crossed these mice with a previously generated mouse line deficient for one Stau1 allele. Reducing Stau1 dosage by 50% led to a significant improvement of motor dysfunction of ATXN2$^{Q127}$ mice as measured by performance on the accelerating rotarod (FIG. 16C). Although Stau1 reduction was present in the germline, thus prior to symptom onset, the effect on motor performance was only discernible after 8 weeks. This may suggest that Staufen1 reduction may exert its major effect in neurons experiencing chronic stress. Significant and progressive decreases in key Purkinje cell mRNAs and even greater decreases in the respective encoded proteins (Calb1, Pcp2, Pcp4, Rgs8, Homer3 and Fam107b) have been described in ATXN2Q$^{127}$ mice. Reduction of Stau1 expression by 50% in vivo significantly increased levels of these six proteins towards normalization. Upon complete genetic ablation of Stau1 in ATXN2$^{Q127}$ mice, the levels of these proteins returned to normal (FIGS. 16D-16F and FIG. 20).

It is noteworthy that—similar to our in vitro studies—STAU1 ablation in vivo had only minimal effects in wild-type animals. The levels of protein significantly impacted by absence of STAU1 in mutant transgenic animals remained unchanged in wild-type animals. The same was true for markers of autophagy (FIGS. 16D-16F and FIG. 20). This suggests that STAU1 serves as a sensor of cellular stress and once engaged, shows rapid amplification of the signal via reciprocal effects on mTOR and autophagy. In the absence of stress, changes of STAU1 levels appear to have relatively minor effects at least within the parameters measured in this study.

It should be understood that the above-described methods are only illustrative of some embodiments of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that variations including, may be made without departing from the principles and concepts set forth herein.

What is claimed is:

1. A method of minimizing dysregulation of Staufen1-mediated RNA metabolism in a target cell, comprising:
    introducing an amount of a Staufen1-regulating agent to the target cell that is sufficient to minimize said dysregulation, wherein the Staufen1-regulating agent is a member selected from the group consisting of an antisense oligonucleotide (ASO), a small interfering RNA (siRNA), a small molecule, a micro RNA (miRNA), a ribozyme, or a combination thereof, and
    wherein minimizing dysregulation of Staufen1-mediated RNA metabolism includes reducing Staufen1 expression, reducing Staufen1 activity, reducing mutant ATXN2 expression, reducing mTOR expression, reducing or blocking Staufen1 interaction with mRNAs resulting in altered mRNA expression or abundance, or a combination thereof,
    wherein the Staufen1-regulating agent comprises a nucleotide sequence that is at least 85% homologous to and having the same number of nucleotides as SEQ ID NO: 1, SEQ ID NO: 2, or a combination thereof.

2. The method of claim 1, wherein introducing comprises introducing the Staufen1-regulating agent to the target cell with a non-viral vector.

3. The method of claim 1, wherein introducing comprises introducing the Staufen1-regulating agent to the target cell with a viral vector.

4. The method of claim 1, wherein introducing comprises introducing the Staufen1-regulating agent without a delivery vector.

5. The method of claim 1, wherein the amount of Staufen 1-regulating agent increases PCP2 mRNA levels in the target cell, CALB1 mRNA levels in the target cell, or both as compared to said levels prior to or without introducing the Staufen1-regulating agent.

6. The method of claim 1, wherein the amount of Staufen 1-regulating agent reduces Staufen1 levels in the target cell by at least 50% as compared to Staufen1 levels in the targets cell prior to or without introduction of the Staufen1-regulating agent.

7. The method of claim 1, wherein the amount of Staufen 1-regulating agent reduces mutant ATXN2 levels in target cells by at least 50% as compared to mutant ATXN2 levels in targets cells prior to or without administration of the Staufen1-regulating agent.

* * * * *